US011911532B2

(12) United States Patent
Shandas et al.

(10) Patent No.: US 11,911,532 B2
(45) Date of Patent: Feb. 27, 2024

(54) REVERSE THERMAL GELS AND THEIR USE AS VASCULAR EMBOLIC REPAIR AGENTS

(71) Applicant: The Regents Of The University Of Colorado, A Body Corporate, Denver, CO (US)

(72) Inventors: Robin Shandas, Boulder, CO (US); Steven Lewis, Denver, CO (US); Daewon Park, Englewood, CO (US); Omid Jazaeri, Denver, CO (US); Steven Lammers, Lafayette, CO (US); James Bardill, Aurora, CO (US); Brisa Pena-Castellanos, Aurora, CO (US)

(73) Assignee: The Regents Of The University of Colorado, A Body Corporate, Denver, CO (US)

( * ) Notice: Subject to any disclaimer, the term of this patent is extended or adjusted under 35 U.S.C. 154(b) by 470 days.

(21) Appl. No.: 16/498,595

(22) PCT Filed: Mar. 29, 2018

(86) PCT No.: PCT/US2018/025059
§ 371 (c)(1),
(2) Date: Sep. 27, 2019

(87) PCT Pub. No.: WO2018/183624
PCT Pub. Date: Oct. 4, 2018

(65) Prior Publication Data
US 2020/0246502 A1 Aug. 6, 2020

Related U.S. Application Data

(60) Provisional application No. 62/513,248, filed on May 31, 2017, provisional application No. 62/478,457, filed on Mar. 29, 2017.

(51) Int. Cl.
*A61L 24/04* (2006.01)
*A61L 24/00* (2006.01)
*C08G 81/02* (2006.01)
*C08J 3/075* (2006.01)

(52) U.S. Cl.
CPC .......... *A61L 24/043* (2013.01); *A61L 24/001* (2013.01); *C08G 81/027* (2013.01); *C08J 3/075* (2013.01); *A61L 2400/06* (2013.01); *A61L 2430/36* (2013.01)

(58) Field of Classification Search
CPC .......... C08G 65/33324; C08G 59/1494; C08G 65/3322; C08G 65/33368; C08G 81/027; C08G 81/024; C08J 2333/26; C08J 3/075; A61L 24/06; A61L 24/043; A61L 24/001; A61L 2430/36; A61L 2400/06
See application file for complete search history.

(56) References Cited

U.S. PATENT DOCUMENTS

| | | | |
|---|---|---|---|
| 4,334,024 A | 6/1982 | Johal | |
| 5,525,334 A | 6/1996 | Ito et al. | |
| 5,695,480 A | 12/1997 | Evans et al. | |
| 5,830,178 A | 11/1998 | Jones et al. | |
| 6,004,573 A | 12/1999 | Rathi et al. | |
| 6,201,065 B1 | 3/2001 | Pathak et al. | |
| 6,201,072 B1 | 3/2001 | Rathi et al. | |
| 6,203,779 B1 | 3/2001 | Ricci et al. | |
| 6,303,100 B1 | 10/2001 | Ricci et al. | |
| 6,342,202 B1 | 1/2002 | Evans et al. | |
| 6,475,466 B1 | 11/2002 | Ricci et al. | |
| 6,726,654 B2 | 4/2004 | Rosenman | |
| 6,841,617 B2 | 1/2005 | Jeong et al. | |
| 6,852,122 B2 | 2/2005 | Rush | |
| 6,979,464 B2 | 12/2005 | Gutowska | |
| 7,008,628 B2 | 3/2006 | Ron et al. | |
| 7,018,645 B1 | 3/2006 | Piao et al. | |
| 7,160,931 B2 | 1/2007 | Cheng et al. | |
| 7,193,007 B2 | 3/2007 | Cheng et al. | |
| 7,204,997 B2 | 4/2007 | Bromberg et al. | |
| 7,250,177 B2 | 7/2007 | Pathak et al. | |
| 7,303,575 B2 | 12/2007 | Ogle | |
| 7,425,322 B2 | 9/2008 | Cohn et al. | |
| 7,485,317 B1 | 2/2009 | Murayama et al. | |

(Continued)

FOREIGN PATENT DOCUMENTS

CA 2519946 9/2011
WO WO 2013/153550 10/2013
(Continued)

OTHER PUBLICATIONS

Over Lee et al. (Journal of Biomaterials Science 22 (2011) 2357-2367 IDS) (Year: 2011).*
Aggarwal et al. (2011) "Abdominal aortic aneurysm: A comprehensive review," Exp. Clin. Cardiol. 16(1):11-15.
Al-Shammari et al. (2011) "The effect of polymer concentration and temperature on the rheological behavior of metallocene linear low density polyethylene (mLLDPE) solutions," J. King Saud Univ.—Eng. Sci. 23(1):9-14.

(Continued)

*Primary Examiner* — Anna R Falkowitz
(74) *Attorney, Agent, or Firm* — Leydig, Voit & Mayer, Ltd.

(57) ABSTRACT

Provided herein is a class of reversible thermal gel polymers, formulations thereof, methods for using, and methods for making said reversible thermal gel polymers. Reversible thermal gel polymers and formulations are provided having versatile chemical, physical, mechanical and/or optical properties beneficial for a range of applications including medical treatment. In some embodiments, the architecture and composition of the polymer allows for tunable selection of one or more physical properties supporting a particular application.

19 Claims, 32 Drawing Sheets

(56) References Cited

U.S. PATENT DOCUMENTS

| | | | |
|---|---|---|---|
| 7,604,620 | B2 | 10/2009 | Epstein et al. |
| 7,648,713 | B2 | 1/2010 | Sawhney |
| 7,649,023 | B2 | 1/2010 | Shih et al. |
| 7,666,220 | B2 | 2/2010 | Evans et al. |
| 7,700,086 | B2 | 4/2010 | Schwarz |
| 7,708,979 | B2 | 5/2010 | Lowman et al. |
| 7,744,913 | B2 | 6/2010 | Noyes |
| 7,786,220 | B2 | 8/2010 | Lee et al. |
| 8,048,086 | B2 | 11/2011 | Lee-sepsick et al. |
| 8,048,145 | B2 | 11/2011 | Evans et al. |
| 8,105,622 | B2 | 1/2012 | Sawhney |
| 8,177,950 | B2 | 5/2012 | Thompson et al. |
| 8,246,990 | B2 | 8/2012 | Gemert et al. |
| 8,257,723 | B2 | 9/2012 | Noyes |
| 8,299,178 | B2 | 10/2012 | Hsiue et al. |
| 8,377,418 | B2 | 2/2013 | Auzely-velty et al. |
| 8,383,158 | B2 | 2/2013 | Michal et al. |
| 8,491,623 | B2 | 7/2013 | Vogel et al. |
| 8,512,757 | B2 | 8/2013 | Yang et al. |
| 8,541,013 | B2 | 9/2013 | Yang et al. |
| 8,586,087 | B2 | 11/2013 | Lee et al. |
| 8,628,789 | B2 | 1/2014 | Baughman et al. |
| 8,642,666 | B2 | 2/2014 | Shih et al. |
| 8,691,245 | B2 | 4/2014 | Bischof |
| 8,801,768 | B2 | 8/2014 | Karwa et al. |
| 8,821,849 | B2 | 9/2014 | Schwarz |
| 8,821,899 | B2 | 9/2014 | Peppas et al. |
| 8,870,941 | B2 | 10/2014 | Evans et al. |
| 8,889,791 | B2 | 11/2014 | Guan et al. |
| 8,900,556 | B2 | 12/2014 | Oxman et al. |
| 8,906,084 | B2 | 12/2014 | Evans et al. |
| 8,926,682 | B2 | 1/2015 | Herbowy et al. |
| 8,945,199 | B2 | 2/2015 | Ganpath et al. |
| 9,011,927 | B2 | 4/2015 | Mitra et al. |
| 9,040,074 | B2 | 5/2015 | Holzer et al. |
| 9,044,580 | B2 | 6/2015 | Freyman et al. |
| 9,050,091 | B2 | 6/2015 | Kassab et al. |
| 9,132,199 | B2 | 9/2015 | Friberg et al. |
| 9,155,722 | B2 | 10/2015 | Fowers et al. |
| 9,216,076 | B2 | 12/2015 | Mitra et al. |
| 9,289,536 | B2 | 3/2016 | Bankert et al. |
| 9,700,628 | B1 | 7/2017 | Park et al. |
| 9,949,484 | B2 | 4/2018 | Park |
| 9,949,928 | B2 | 4/2018 | Park et al. |
| 9,999,224 | B2 | 6/2018 | Park et al. |
| 10,251,955 | B1 | 4/2019 | Park et al. |
| 2002/0169473 | A1 | 11/2002 | Sepetka et al. |
| 2005/0152941 | A1* | 7/2005 | Hunter ............... A61L 27/3641 |
| | | | 623/8 |
| 2011/0087207 | A1 | 4/2011 | Vogel et al. |
| 2012/0265287 | A1 | 10/2012 | Sharma et al. |
| 2013/0331929 | A1 | 12/2013 | Mitra et al. |
| 2014/0052168 | A1 | 2/2014 | Sawhney |
| 2014/0135811 | A1 | 5/2014 | Divino et al. |
| 2014/0277074 | A1 | 9/2014 | Kaplan et al. |
| 2015/0010471 | A1 | 1/2015 | Schwarz et al. |
| 2015/0045872 | A1 | 2/2015 | Cully et al. |
| 2016/0030051 | A1 | 2/2016 | Bankert et al. |
| 2016/0030165 | A1 | 2/2016 | Mitra et al. |
| 2016/0051264 | A1 | 2/2016 | Freyman et al. |
| 2016/0051469 | A1* | 2/2016 | Park ..................... A61K 9/0051 |
| | | | 424/501 |
| 2016/0082115 | A1 | 3/2016 | Friberg et al. |
| 2016/0366890 | A1* | 12/2016 | Park ..................... A01N 47/34 |

FOREIGN PATENT DOCUMENTS

| | | | | |
|---|---|---|---|---|
| WO | WO 2015/106149 | * | 7/2015 | ............. A01N 47/28 |
| WO | WO 2018/183624 | | 10/2018 | |

OTHER PUBLICATIONS

Asouhidou et al. (2010) "Desaturation during Onyx embolization," Br J Anaesth. Sep. 2010: 105(3)385-386.

Baum et al. (2002) "Treatment of type 2 endoleaks after endovascular repair of abdominal aortic aneurysms : Comparison of transarterial and translumbar techniques," J. Vasc. Surg. 35(1):23-29.

Bockler et al. (2015) "Multicenter Nellix EndoVascular Aneurysm Sealing system experience in aneurysm sac sealing," J. Vasc. Surg. 62(2):290-298.

Constantin et al. (2011) "Lower critical solution temperature versus volume phase transition temperature in thermoresponsive drug delivery systems," Express Polym. Lett. 5(10):839-848.

Criado (2011) "The EVAR Landscape in 2011," Endovascular Today, Mar. 2011, pp. 40-44, 58.

Department of Health and Human Services, Food and Drug Administration "Use of International Standard ISO 10993-1 , 'Biological evaluation of medical devices—Part 1 : Evaluation and testing within a risk management process'; Guidance for Industry and Food and Drug Administration Staff," (Jun. 2016) Federal Register 39269 81(116) Notices, 3 pp.

Gaharwar et al. (2014) "Shear-Thinning Nanocomposite Hydrogels for the Treatment of Hemorrhage," ACS Nano. 8(10):9833-9842.

Gianturco et al. (1975) "Mechanical devices for arterial occlusion," Am. J. Roentgenol. Radium Ther. Nucl. Med. 124(3):428-435.

International Search Report and Written Opinion, dated May 30, 2018, corresponding to International Application No. PCT/US2018/025059, from which the present application claims priority, 11 pp.

Jackson et al. (2009) "Devices Used for Endovascular Aneurysm Repair: Past, Present, and Future," Semin. Intervent. Radiol. 26(1):39-43.

Johnsen et al. (2010) "Atherosclerosis in Abdominal Aortic Aneurysms: A Causal Event or a Process Running in Parallel? The Tromsø Study," Arteriosclerosis, Thrombosis, and Vascular Biology 30(6):1263-1268.

Kallmes et al. (2002) "New Expandable Hydrogel-Platinum Coil Hybrid Device for Aneurysm Embolization," Am. J. Neuroradiol. 23(9):1580-1588.

Kocer et al. (publicly available Jan. 2016) "Preliminary experience with precipitating hydrophobic injectable liquid in brain arteriovenous malformations," Diagn. Interv. Radiol. (Mar. 2016) 22(2):184-189.

LV et al. (2009) "Complications Related to Percutaneous Transarterial Embolization of Intracranial Dural Arteriovenous Fistulas in 40 Patients," Am. J. Neuroradiol. 30(3):462-468.

Lyu et al. (2009) "Degradability of Polymers for Implantable Biomedical Devices," Int. J. Mol. Sci. 10(9):4033-4065.

Mora et al. (2015) "Maximum Diameter of Native Abdominal Aortic Aneurysm Measured by Angio-Computed Tomography: Reproducibility and Lack of Consensus Impacts on Clinical Decisions," Aorta (Stamford) 3(2):47-55.

Nawaz et al. (2010) "Investigating the compatibility of polymers in common solvent," J. Chil. Chem. Soc. 55(1):90-93.

Nguyen et al. (2012) "Incompressible Non-Newtonian Fluid Flows," Chapter 3 in Continuum Mechanics: Progress in Fundamentals and Engineering Applications, pp. 47-72.

Nobbmann et al. (2007) "Dynamic light scattering as a relative tool for assessing the molecular integrity and stability of monoclonal antibodies," Biotechnol. Genet. Eng. Rev. 24(1):117-128.

Pena et al. (2015) "A heparin-mimicking reverse thermal gel for controlled delivery of positively charged proteins," J. Biomed. Mater. Res. A. 103(6):2102-2108.

Simon et al. (2011) "Hydrophilic Coatings: Considerations for Product Development," [Online]. Available: https://www.mddionline.com/materials/hydrophilic-coatings-considerations-product-development, 11 pp.

Tawil et al. (2011) "Case Report: Acute Respiratory Distress Syndrome after Onyx Embolization of Arteriovenous Malformation," Critical Care Research and Practice 2011, Article ID 918185, 5 pp.

Vaidya et al. (2008) "An overview of embolic agents," Semin. Intervent. Radiol. 25(3):204-215.

Zhao et al. (2013) "Temperature-Sensitive poly(N-Isopropylacrylamide-Co-Butyl Methylacrylate) Nanogel as an Embolic Agent: Distribution, Durability of Vascular Occlusion, and Inflammatory Reactions in the Renal Artery of Rabbits," Am. J. Neuroradiol. 34(1):169-176.

Aggarwal et al. (2011) "Abdominal aortic aneurysm: A comprehensive review," Exp Clin Cardiol vol. 16 No. 1, 11-15.

(56) References Cited

OTHER PUBLICATIONS

Avery et al. (Nov. 2016) "An injectable shear-thinning biomaterial for endovascular embolization," Sci. Transl. Med. 8(365):365ra156 LP-365ra156.
Baum et al. (2002) "Treatment of type 2 endoleaks after endovascular repair of abdominal aortic aneurysms: Comparison of transarterial and translumbar techniques," Journal of Vascular Surgery 35, 1, 23-29.
Becker et al. (2002) "Flow properties of liquid calcium alginate polymer injected through medical microcatheters for endovascular embolization," J. Biomed. Mater. Res. 61(4):533-540.
Becker et al. (2007) "Preliminary investigation of calcium alginate gel as a biocompatible material for endovascular aneurysm embolization in vivo," Neurosurgery 60(6):1119-1128.
Brennecka et al. (2013) "In vivo embolization of lateral wall aneurysms in canines using the liquid-to-solid gelling PPODA-QT polymer system: 6-month pilot study," J. Neurosurg. 119: Issue 1 (Jul. 2013): 228-238.
Christenson et al. (2004) "Oxidative mechanisms of poly(carbonate urethane) and poly(ether urethane) biodegradation: in vivo and in vitro correlations.," J. Biomed. Mater. Res. A 70(2):245-255.
Eberhardt et al. (2014) "Treatment of type I endoleaks using transcatheter embolization with onyx," J. Endovasc. Ther. 21(1)162-171.
Engelmann et al. (2013) "Thrombosis as an intravascular effector of innate immunity," Nat. Rev. Immunol. 13(1):34-45.
Ganz et al. (2001) "Surgical dislocation of the adult hip: A technique with full access to the femoral head and acetabulum without the risk of avascular necrosis," J Bone Joint Surg [Br] 83-B:1119-1124.
Jeong et al. (2002) "Thermosensitive sol-gel reversible hydrogels," Advanced Drug Delivery Reviews 54, 37-51.
KENT (2014) "Clinical Practice. Abdominal Aortic Aneurysms," N. Engl. J. Med. 371(22):2101-2108.
Lee et al. (2001) "Novel Thermoreversible Gelation of Biodegradable PLGA-*block*-PEO-*block*-PLGA Triblock Copolymers in Aqueous Solution," Macromolecular Rapid Communications 22(8):587-592.
Lee et al. (2011) "Synthesis and Characterization of Thermo-Sensitive Radio-Opaque Poly(N-isopropylacrylamide-co-PEG-2-iodobenzoate)," J. Biomater. Sci. Polym. Ed. 22(17):2357-2367.
Massis et al. (2012) "Treatment of Type II Endoleaks With Ethylene-Vinyl-Alcohol Copolymer (Onyx)," Vasc. Endovascular Surg. 46(3):251-257.
Mei-Dan et al. (Mar. 2018) "Hip Distraction Without a Perineal Post: A Prospective Study of 1000 Hip Arthroscopy Cases," The American Journal of Sports Medicine 46(3):632-641.
Momeni et al. (publicly available Dec. 2015) "Developing an in situ forming polyphosphate coacervate as a new liquid embolic agent: From experimental design to pilot animal study," Acta Biomater. (Mar. 2016) 32:286-297.
Müller-Wille et al. (2013) "Transarterial Embolization of Type II Endoleaks after EVAR : The Role of Ethylene Vinyl Alcohol Copolymer (Onyx )," Cardiovasc Intervent Radiol. 36(5):1288-1295.
Nevala et al. (2010) "Type II endoleak after endovascular repair of abdominal aortic aneurysm: effectiveness of embolization," Cardiovasc. Intervent. Radiol. 33(2):278-284.
Ogura et al. (2007) "Preparation and Solution Behavior of a Thermoresponsive Diblock Copolymer of Poly(ethyl glycidyl ether) and Poly(ethylene oxide)," Langmuir. 23(18):9429-9434.
Oh et al. (2008) "Secondary Structure Effect of Polypeptide on Reverse Thermal Gelation and Degradation of L/DL-Poly(alanine)-Poloxamer-L/DL-Poly(alanine) Copolymers," Macromolecules 41(21):8204-8209.
Pande et al. (2008) "Abdominal Aortic Aneurysm : Populations at Risk and How to Screen," J. Vasc. Interv. Radiol. 19(6 Suppl):S2-S8.
Park et al. (2011) "A functionalizable reverse thermal gel based on a polyurethane/PEG block copolymer," Biomaterials 32(3):777-786.
Peng et al. (2013) "Injectable and biodegradable thermosensitive hydrogels loaded with PHBHHx nanoparticles for the sustained and controlled release of insulin," Acta Biomater. 9(2):5063-5069.
Plunkett et al. (2006) "PNIPAM chain collapse depends on the molecular weight and grafting density," Langmuir. 22(9):4259-4266.
Pollak et al. (2001) "The Use of Cyanoacrylate Adhesives in Peripheral Embolization," J. Vasc. Interv. Radiol. 12(8):907-913.
Poursaid et al. (publicly available Feb. 2016) "Polymeric materials for embolic and chemoembolic applications," J. Control Release. (Oct. 2016) 240:414-433.
Qin et al. (publicly available Jun. 2015) "Phytantriol based liquid crystal provide sustained release of anticancer drug as a novel embolic agent.," Drug Dev. Ind. Pharm. (2016) 42(2): 307-316.
Sakalihasan et al. (2005) "Abdominal aortic aneurysm," The Lancet 365(9470): 1577-1589.
Schatz et al. (2003) "Static light scattering studies on chitosan solutions: From macromolecular chains to colloidal dispersions," Langmuir. 19(23)9896-9903.
Schubert et al. (1995) "Oxidative biodegradation mechanisms of biaxially strained poly(etherurethane urea) elastomers," J. Biomed. Mater. Res. 29(3):337-347.
Schubert et al. (1997) "Role of oxygen in biodegradation of poly(etherurethane urea) elastomers," J. Biomed. Mat. Res. 34(4):519-530.
Shachaf et al. (2010) "The biocompatibility of PluronicF127 fibrinogen-based hydrogels," Biomaterials 31(10):2836-2847.
Shenoi et al. (2013) "Biodegradable polyglycerols with randomly distributed ketal groups as multi-functional drug delivery systems," Biomaterials 34, 6068-6081.
Stavropoulos et al. (2005) "Embolization of type 2 endoleaks after endovascular repair of abdominal aortic aneurysms with use of cyanoacrylate with or without coils," J Vasc Interv Radiol. 16(6):857-861.
Vaidya et al. (2008) "An Overview of Embolic Agents," Semin Intervent Radiol 25:204-215.
Vernon et al. (2005) "Gel strength and solution viscosity of temperature-sensitive, in-situ-gelling polymers for endovascular embolization," J. Biomater. Sci. Polym. Ed. 16(9):1153-1166.
Vrachliotis et al. (2007) "Infections After Endovascular Coil Embolization," J. Endovasc. Ther. 14(6):805-806.
Zhang et al. (2004) "Synthesis and characterization of partially biodegradable, temperature and pH sensitive Dex-MA/PNIPAAm hydrogels," Biomaterials 25(19):4719-4730.
Zhang et al. (2005) "Specific Ion Effects on the Water Solubility of Macromolecules: PNIPAM and the Hofmeister Series," J. Am. Chem. Socc. 127, 14505-14510.
Zhao et al. (2011) "Permanent and Peripheral Embolization : Temperature-Sensitive p(N-Isopropylacrylamide-co-butyl Methylacrylate) Nanogel as a Novel Blood-Vessel-Embolic Material in the Interventional Therapy of Liver Tumors," Adv. Funct. Mater. 21(11):2035-2042.
Zhou et al. (1995) "Light-scattering studies of poly(N-isopropylacrylamide) in tetrahydrofuran and aqueous solution," Polymer (Guildf). 36(7):1341-1346.

* cited by examiner

Complex Shape
 Straight Shape
 Flat Spiral Shape
 C-Shape

PEGSA synthesis

PNIPAm synthesis

REVERSE THERMAL GELS AND THEIR USE AS VASCULAR EMBOLIC REPAIR AGENTS

CROSS-REFERENCE TO RELATED APPLICATIONS

This application is a U.S. National Stage Application under 35 U.S.C. § 371 of International Application No. PCT/US2018/025059, filed Mar. 29, 2018, which claims the benefit of and priority to U.S. provisional patent app. Nos. 62/478,457 filed Mar. 29, 2017 and 62/513,248 filed May 31, 2017, each of which is incorporated by reference herein in its entirety, except to the extent inconsistent herewith.

STATEMENT REGARDING FEDERALLY SPONSORED RESEARCH OR DEVELOPMENT

Not applicable

BACKGROUND OF INVENTION

Stimuli-responsive polymers are a class of materials having properties that change according to their environment. Environmental factors that may induce property change in stimuli-responsive polymers include, for example, temperature, humidity, pH, and the wavelength and/or intensity of light irradiation. Due to their diverse and responsive properties, these materials are finding increasingly important roles in a broad range of applications, including drug delivery, tissue engineering, biosensors, diagnostics, microelectrochemical systems, coatings, textiles, and cosmetics.

A particularly useful sub-class of stimuli-responsive polymers is that of reversible thermal gels (RTGs), which reversibly exhibit abrupt change in solubility as the environment temperature crosses a threshold called the low critical solution temperature (LCST). At temperatures below the low critical solution temperature (LCST), RTGs are in a free-flowing liquid state. At temperature above the LCST, RTGs are in a non-flowing solid-gel state. In contrast, many conventional polymers exhibit a continuous, not abrupt, transition from a solid glassy state to a viscous rubbery state with increasing temperature. RTGs are polymers composed of multiple chemical constituents each having different properties. RTGs may be branched, di-block, or multi-block copolymers. Providing a combination of hydrophobic, hydrophilic, and thermally-responsive constituents, for example, allows RTGs to be adapted to diverse application requirements. RTGs may be synthesized to further include other polymer blocks for additional functionality, such as protein targeting and radiopacity. The specific chemical composition of the RTG influences its range of material properties, which include the LCST, molecular weight, viscosity, tensile strength, and biocompatibility.

Biological applications are one particularly interesting and beneficial set of applications for RTGs, including treatment of medical conditions. For example, endoleaks (types I through V) are a class of complications associated with the treatment of abdominal aortic aneurysm, a potentially-fatal condition in which the abdominal aortic vessel is enlarged by more than 1.5 times the normal vessel diameter. Rupture of the abdominal aortic aneurysm leads to over 13,000 deaths in the United States annually. Abdominal aortic aneurysm is treated by a technique called endovascular aortic repair, in which a stent-graft is placed at the aneurysm restore normal blood flow in the region. A type II endoleak, accounting for 80% of endoleak cases, is one complication in which the aneurysm continues to enlarge due to retrograde blood flow. One treatment for type II endoleaks is endovascular embolization using a targeted injection of an embolic agent to block and prevent blood flow into the aneurysm sac.

A variety of polymers have been studied or proposed as embolic agents in treatment of type II endoleaks. Non-RTG polymers for embolization include, for example, those that solidify upon interaction with a separately injected agent or upon exposure to the pH of the body [see K. Massis, W. G. Carson III, A. Rozas, V. Patel, and B. Zwiebel, Endovasc. Tech., vol. 46, no. 3, pp. 251-257, 2015; A. Poursaid, M. M. Jensen, E. Huo, and H. Ghandehari, J. Control. Release, 2016; C. Brennecka, M. Preul, T. Becker, B. Vernon, J. Neurosurg., vol. 119, no. July, pp. 228-238, 2013; S. Stavropoulos, J. Vasc. Interv. Radiol., vol. 16, no. 6, 2005]. Disadvantages and challenges associated with polymer materials for embolization include toxicity (e.g., due to use of dimethyl sulfoxide), high viscosity, fast polymerization leading to catheter occlusion, migration within the body, and complicated preparation and administration [see K. Eberhardt, M. Sadeghi-Azandaryani, S. Worlicek, T. Koeppel, M. F. Reiser, and M. Treitl, J. Endovasc. Ther., vol. 21, no. 1, pp. 162-71, 2014].

There is interest in developing RTGs for embolization, such as treatment of type II endoleaks. For example, Lee, et al. reports an RTG polymer consisting of poly(n-isopropylacrylamide-co-polyethylene glycol-acrylate) for embolization [see B. Lee, C. Leon, R. McLemore, J. Macias, and B. Vernon, J. Biomater. Sci. Polym. Ed., vol. 22, no. 17, pp. 2357-2367, 2011]. In another example, U.S. Patent Application No. 2015/0010471 reports polyethylene oxide-polypropylene oxide-polyethylene oxide RTG polymers for temporary embolization procedures. In another example, U.S. Pat. No. 7,708,979 reports poly(n-isopropyl acrylamide) RTG polymers for biomaterial applications.

It will be apparent from the foregoing that development of RTG polymers exhibiting advantageous physical, chemical and optical properties is needed for a range of applications, including treatment of medical conditions.

SUMMARY OF THE INVENTION

Provided herein is a class of reversible thermal gel polymers, formulations thereof, methods for using, and methods for making said reversible thermal gel polymers. Reversible thermal gel polymers and formulations are provided having versatile chemical, physical, mechanical and/or optical properties beneficial for a range of applications including medical treatment. In some embodiments, the architecture and composition of the polymer allows for tunable selection of one or more physical properties supporting a particular application. The reversible thermal gel polymers of certain embodiments, for example, are characterized by a reversible rapid transition between a free-flowing liquid state and non-flowing solid-gel state as the environment temperature crosses a threshold called the low critical solution temperature (LCST), for example, a LCST achieved upon providing the reversible thermal gel polymer in an in vivo environment. The invention also provides polymer formulations comprising reversible thermal gel polymers exhibiting useful chemical and physical properties including viscosities, compressive strengths and/or tensile strain-to-failure, for example, allowing useful administration via a catheter, microcatheter or other lumen device. In certain embodiments, the polymers and formulations thereof, provide a combination of properties, such as a viscosity and LCST useful for clinical medical treatments, for example, treatment relating to embolization of type II endoleaks.

The reversible thermal gel polymers of certain embodiments comprise a repeating chemical structure. The repeating chemical structure of the polymer comprises at least two chemically different blocks, each block comprising repeating units. The different blocks are directly or indirectly covalently linked. At least a portion of the repeating units comprise a hydrophilic chemical group and at least a portion of the repeating units comprise a thermosensitive chemical group. The reversible thermal gel polymer may further comprise hydrophobic chemical groups. Reversible thermal gel polymers of some embodiments are characterized by low viscosities and a low critical solution temperature in the range of 32° C. to 37° C.

Further provided herein are formulations including a solvent and a reversible thermal gel polymer, the reversible gel polymer including repeating units containing hydrophilic groups and repeating units containing thermosensitive groups, which at least two repeating polymer blocks directly or indirectly covalently linked. The solvent may be, for example, a saline solution, enabling application of said polymer formulations for treatment of medical complications and disorders. Also provided herein are methods of using said polymers comprise forming a polymer formulation and administrating the polymer formulation to a target medium of a subject. Examples of target media comprising mammalian blood vessel, organ, or tissue. Additionally provided herein are methods of making said reversible thermal gel polymers.

In an aspect, a reversible thermal gel polymer has the formula (FX1):

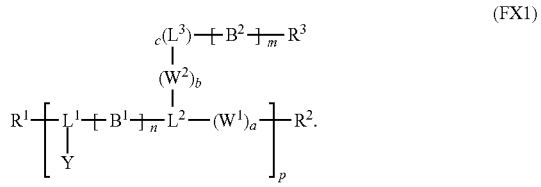

(FX1)

In an embodiment of this aspect:
$B^1$ is

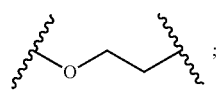 [SMILES: *CCO*]

;

$B^2$ is

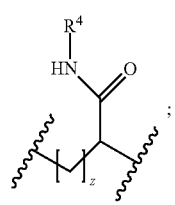

;

Y is selected from the group consisting of —OH, a radiopaque group, and a targeting ligand;

each of $L^1$ and $L^2$ is independently selected from the group consisting of $C_qH_{2q-1}$, $C_qH_{2q-1}X$, and $(C_rH_{r+2})X$;
X is O or S;
$L^3$, if present, is selected from the group consisting of a single bond, —$(CH_2)_q$—, —$(HCCH)_q$—, —$(CH_2CH_2X)_q$—, —$(CHXH)_q$—, —X—, —$NR^5$—, —CX—, —CXX—, —XCX—, —$XCX(CH_2)_qCXX$—, —$CXNR^5$—, —$NR^5CX$—, —$XCXNR^5$—, —$NR^5CXX$—, —$CX(CH_2)_qCR^5CN$—, —$(CH_2)_qX(CH_2)_r$—, —$(CH_2)_qXX(CH_2)_r$—, —$(CH_2)_qNR^5(CH_2)_r$—, —$(CH_2)_qCX(CH_2)_r$—, —$(CH_2)_qCXX(CH_2)_r$—, —$(CH_2)_qCXNR^5(CH_2)_r$—, —$(CH_2)_qNR^5CX(CH_2)_r$—, —$(CH_2)_qXCXNR^5(CH_2)_r$—, and —$(CH_2)_qNR^5CXNR^6(CH_2)_r$—;
each of $W^1$ and $W^2$, if present, is independently selected from the group consisting of a single bond, —$(CH_2)_q$—, —$(HCCH)_q$—, —$(CH_2CH_2X)_q$—, —$(CHXH)_q$—, —X—, —CXX—, —XCX, —CX—, —$XCX(CH_2)_qCXX$—, and —$NR^1$—;
each of $R^1$, $R^2$, $R^3$, and $R^4$ is independently selected from the group consisting of hydrogen, halide, and $C_1$-$C_5$ alkyl;
each of a, b, and c is independently 0 or 1;
each of q and r is an integer independently selected from the range of 1 to 10;
z is an integer selected from the range of 0 to 4;
m is an integer selected from the range of 1 to 10,000;
n is an integer selected from the range of 1 to 1,000;
p is an integer selected from the range of 1 to 1,000; and
each of $R^5$, $R^6$ and $R^{11}$ is independently selected from the group consisting of hydrogen, $C_1$-$C_{10}$ alkyl, $C_5$-$C_{10}$ aryl and $C_5$-$C_{10}$ heteroaryl.

In an embodiment, for example, the reversible thermal gel polymer has the formula (FX2):

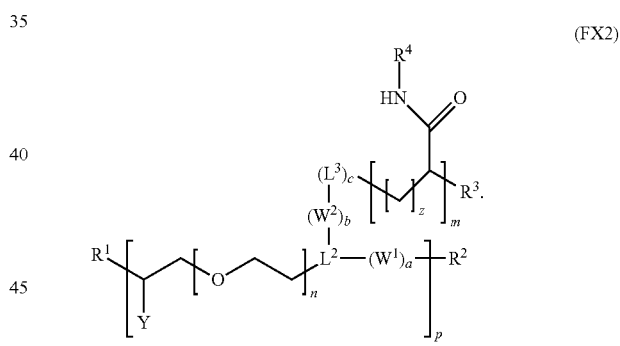

(FX2)

In an embodiment, for example, the reversible thermal gel polymer has the formula (FX3):

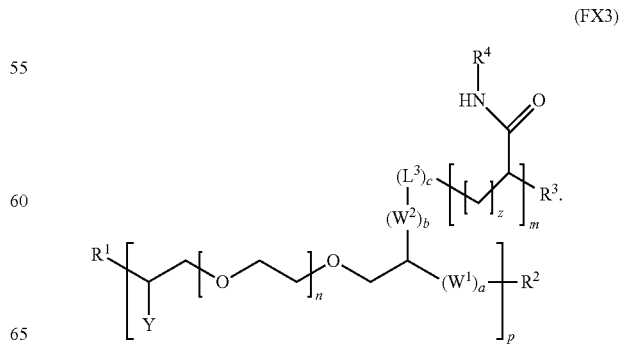

(FX3)

In an embodiment, for example, the reversible thermal gel polymer has the formula (FX4):

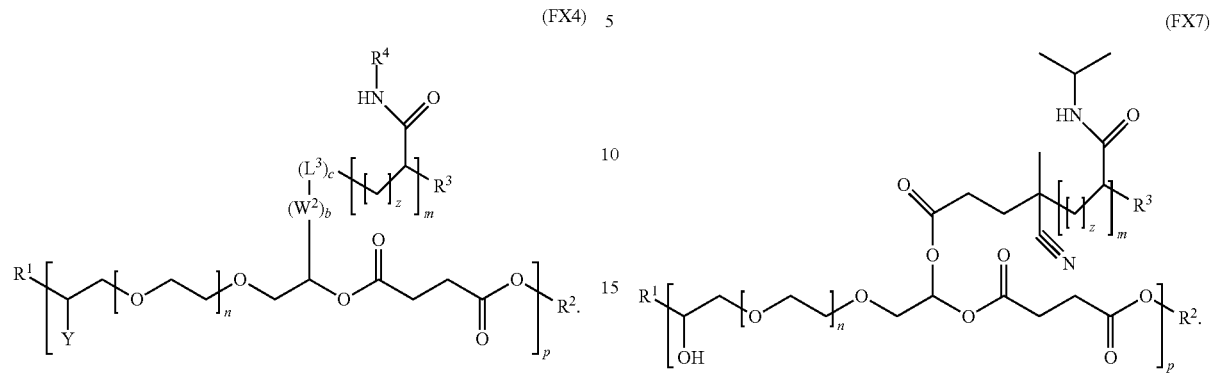

(FX4)

In an embodiment, for example, the reversible thermal gel polymer has the formula (FX5):

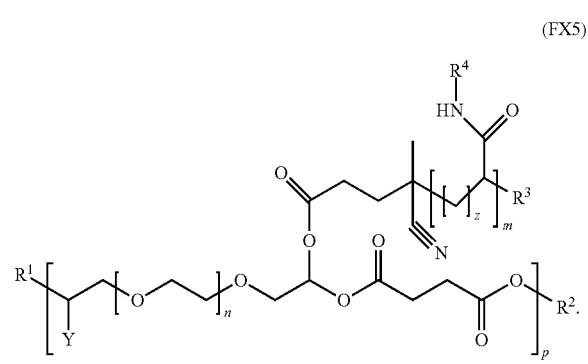

(FX5)

In an embodiment, for example, the reversible thermal gel polymer has the formula (FX6):

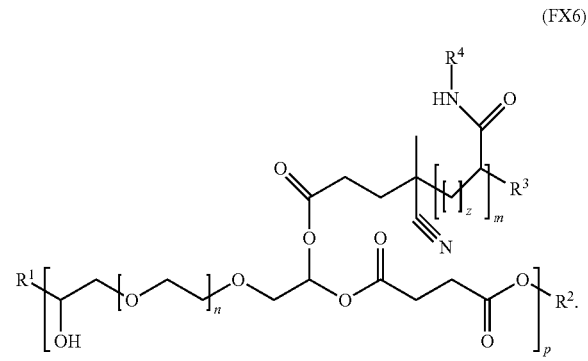

(FX6)

In an embodiment, for example, the reversible thermal gel polymer has the formula (FX7):

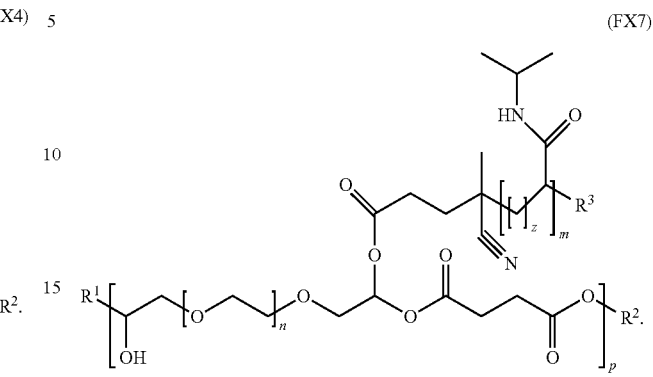

(FX7)

Reversible thermal gel polymers of the invention may optionally include a range of radiopaque groups useful for visualization and imaging in diverse clinical settings. In an embodiment, for example, the radiopaque group of reversible thermal gel polymer is a halogen substituted $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, $C_3$-$C_{10}$ arylene, $C_3$-$C_{10}$ heteroarylene, $C_2$-$C_{10}$ alkenylene, $C_3$-$C_{10}$ cycloalkenylene, or $C_2$-$C_{10}$ alkynylene, wherein the radiopaque group comprises at least one, and optional 2-5, halo groups. In an example of this embodiment, the radiopaque group is a bromide or chloride group, such as iodobenzoyl chloride.

Reversible thermal gel polymers of the invention may optionally include a range of targeting groups including groups derived from biomolecules. In an embodiment, for example, the targeting ligand of reversible thermal gel polymer is a group derived from an aptamer, a polypeptide, a protein, an oligonucleotide, a carbohydrate, a saccharide, an antibody, or any fragments thereof.

Reversible thermal gel polymers of the invention exhibit physical properties useful for a range of applications. In an embodiment, for example, the reversible thermal gel polymer is characterized by a weight-averaged molecular weight selected from the range of 10,000 to 500,000 kDa. In an embodiment, for example, the reversible thermal gel polymer is characterized by a low critical solution temperature achievable in an in vivo environment. In an embodiment, for example, the low critical solution temperature of the polymer is selected from the range of 35.5° C. to 43.3° C. In an embodiment, for example, the low critical solution temperature of the polymer is selected from the range of 32° C. to 43.3° C. In an embodiment, for example, the reversible thermal gel polymer is characterized by a low critical solution temperature selected from the range of 32° C. to 37° C. In an embodiment, for example, the low critical solution temperature of the polymer is selected from the range of 34° C. to 35.2° C. In an embodiment, for example, the reversible thermal gel polymer is characterized by a polydispersity index less than or equal to 4.0. In an embodiment, for example, the reversible thermal gel polymer, when in solid form, is characterized by a compressive strength selected from the range of 300 kPa to 10 MPa. In an embodiment, for example, the reversible thermal gel polymer, when in solid form, is characterized by a tensile strain-to-failure selected from the range of 150% to 200%.

In another aspect, the invention provides reversible thermal gel polymer formulations providing advantageous physical and chemical properties. In an embodiment, for example, a reversible thermal gel polymer formulation comprises: reversible thermal gel polymers, wherein each of the polymers independently comprise: a first polymer block comprising first repeating units, wherein each of the first repeating units of the first polymer block independently comprise a hydrophilic group; and a second polymer block comprising second repeating units, wherein each of the second repeating units of the second polymer block independently comprise a thermosensitive group; wherein the first polymer block and the second polymer block are directly or indirectly covalently linked. In an aspect, the reversible thermal gel polymer formulation further comprises a solvent. In an aspect, said reversible thermal gel polymers are dissolved in said solvent and are characterized by a concentration in the solvent selected from the range of 2% to 50% w/v, optionally 5% to 50% w/v, optionally 10% to 50% w/v, or optionally 20% to 40% w/v. In a further embodiment of this aspect, the polymer formulation is characterized by a viscosity less than or equal to 1,500 cP, optionally less than or equal to 1,000 cP.

In an embodiment, for example, each of the reversible thermal gel polymers of the polymer formulation is independently characterized by the formula (FX1):

$$(FX1)$$

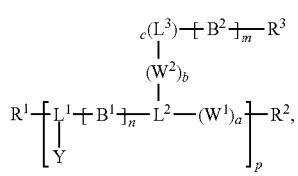

wherein:
$B^1$ is

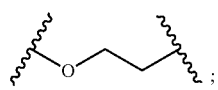 [SMILES: *CCO*]

$B^2$ is z

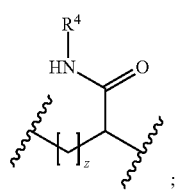

Y is selected from the group consisting of —OH, a radiopaque group, and a targeting ligand;
each of $L^1$ and $L^2$ is independently selected from the group consisting of $C_qH_{2q-1}$, $C_qH_{2q-1}X$, and $(C_rH_{r+2})X$;
X is O or S;
$L^3$, if present, is selected from the group consisting of a single bond, —$(CH_2)_q$—, —$(HCCH)_q$—, —$CH_2CH_2X)_q$—, —$(CHXH)_q$—, —X—, —CX—, —CXX—, —XCX—, —XCX$(CH_2)_q$CXX—, —CXNR$^5$—, —NR$^5$CX—, —XCXNR$^5$—, —NR$^5$CXX—, —CX$(CH_2)_q$CR$^5$CN—, —$(CH_2)_qX(CH_2)_r$—, —$(CH_2)_qXX$ $(CH_2)_r$—, —$(CH_2)_qNR^5(CH_2)_r$—, —$(CH_2)_qCX(CH_2)_r$—, —$(CH_2)_qCXX(CH_2)_r$—, —$(CH_2)_qCXNR^5(CH_2)_r$—, —$(CH_2)_qNR^5CX(CH_2)_r$—, —$(CH_2)_qXCXNR^5(CH_2)_r$—, and —$(CH_2)_qNR^5CXNR^6(CH_2)_r$—;
each of $W^1$ and $W^2$, if present, is independently selected from the group consisting of a single bond, —$(CH_2)_q$—, —$(HCCH)_q$—, —$(CH_2CH_2X)_q$—, —$(CHXH)_q$—, —X—, —CXX—, —XCX, —CX—, —XCX$(CH_2)_q$CXX—, and —NR$^{11}$—;
each of $R^1$, $R^2$, $R^3$, and $R^4$ is independently selected from the group consisting of hydrogen, halide, and $C_1$-$C_5$ alkyl;
each of a, b, and c is independently 0 or 1;
each of q and r is an integer independently selected from the range of 1 to 10;
z is an integer selected from the range of 0 to 4;
m is an integer selected from the range of 1 to 10,000;
n is an integer selected from the range of 1 to 1,000;
p is an integer selected from the range of 1 to 1,000; and
each of $R^5$, $R^6$ and $R^{11}$ is independently selected from the group consisting of hydrogen, $C_1$-$C_{10}$ alkyl, $C_5$-$C_{10}$ aryl and $C_5$-$C_{10}$ heteroaryl.

In an embodiment, for example, each of the reversible thermal gel polymers of the polymer formulation is independently characterized by the formula (FX7):

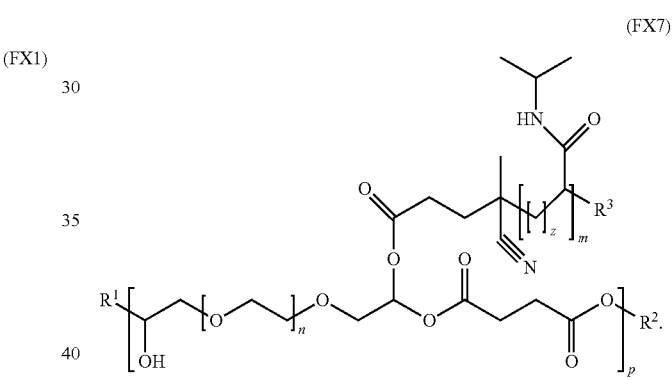

In an embodiment, for example, the reversible thermal gel polymers of the polymer formulation are characterized by a weight-averaged molecular weight selected from the range of 10,000 to 500,000 kDa. In an embodiment, for example, the reversible thermal gel polymers of the polymer formulation are characterized by a polydispersity index selected over the range of 1.0 to 4.0. In an embodiment, for example, the reversible thermal gel polymers of the polymer formulation are characterized by a low critical solution temperature selected from the range of 32° C. to 37° C. 1 In an embodiment, for example, the reversible thermal gel polymers of the polymer formulation are characterized by the low critical solution temperature selected from the range of 34° C. to 35.2° C.

In an embodiment, for example, the reversible thermal gel polymers, when in solid form, of the polymer formulation are characterized by a compressive strength selected from the range of 300 kPa to 10 MPa. In an embodiment, for example, the reversible thermal gel polymers, when in solid form, of the polymer formulation are characterized by a tensile strain-to-failure selected from the range of 150% to 200%.

Polymer formulations of the invention may include a range of components useful for certain applications. In an embodiment, for example, the solvent of the polymer formulation is water, saline, or phosphate-buffered saline. In an embodiment, for example, the polymer formulation further comprises at least one contrasting agent. In an embodiment, for example, the polymer formulation further comprises thrombin. In an embodiment, for example, the polymer formulation further comprises collagen. In an embodiment, for example, the polymer formulation further comprises a co-solvent. In an embodiment, for example, the polymer formulation further comprises whole blood and/or a blood product. In an embodiment, for example, the polymer formulation comprises one or more prothrombotic agents. In an embodiment, for example, the polymer formulation comprises one or more prothrombotic agents selected from the group consisting of collagen, microfiber(s), whole blood, blood product(s), thrombin, and any combination thereof. In an embodiment, for example, the polymer formula further comprises one or more dissolved gases. In an embodiment, for example, the polymer formula further comprises one or more pressurized dissolved gases. In an embodiment, for example, the polymer formulation further comprises polymer microfibers suspended therein. In an embodiment, for example, the polymer formulation further comprises a hemostatic agent. In an embodiment, for example, the polymer formulation further comprises heparin.

In an embodiment, for example, the polymer formulation is characterized by a viscosity selected from the range of 1 cP to 1,500 cP, optionally 500 cP to 1,000 cP. In an embodiment, for example, the polymer formulation is characterized by a concentration of the polymer in the solution greater than or equal to 15% w/v, optionally greater than or equal to 25% w/v, In an embodiment, for example, the polymer formulation is characterized by an injection force selected from the range of 1 N to 160 N, when the polymer formulation is injected through a 2 French microcatheter. In an embodiment, for example, the polymer formulation is characterized by being capable of being injected from a catheter that has a diameter selected from the range of 1 to 8 French.

In an embodiment, for example, the reversible thermal gel polymers of the polymer formulation, upon contacting a target medium, form a gel. In an embodiment, for example, the gel, upon contacting a target medium, comprises a pattern, the pattern comprising one or more of straight noodles, helixes, coils, microparticles, and nanoparticles. In an embodiment, for example, the target medium is an in vivo medium. In an embodiment, for example, the target medium is a tissue or biofluid of an animal. In an embodiment, for example, the target medium is within a human subject. In an embodiment, for example, the gel, upon contacting a target medium, characterized by a space-filling irregular shape that is free of pattern and/or capable of being shaped by external forces. In an embodiment, for example, the gel, upon contacting a target medium, is characterized by a space-filling irregular shape, wherein the shape is amorphous (or free of pattern) and/or capable of being shaped by an external force. In an embodiment, for example, the gel, upon contacting a target medium, forms a space-filling gel, wherein the space-filling gel is capable of being shaped by an external force.

In an embodiment, for example, the polymer formulation is used to embolize the left atrial appendage either alone or in tandem with another medical implant device. In an embodiment, for example, the polymer formulation is used as a topical wound dressing. In an embodiment, for example, the polymer formulation is used as a barrier between medical devices and internal tissues. In an embodiment, for example, the polymer formulation is used as a space filler for cosmetic surgery. In an embodiment, for example, the polymer formulation is used to occlude peripheral veins or arteries. In an embodiment, for example, the polymer formulation is used to embolize arteriovenous malformations.

In an embodiment, for example, the polymer formulation is characterized by a maximum volumetric shrinkage selected from the range of 5% to 52%.

In another aspect, the invention provides methods of using reversible thermal gel polymer formulations supporting a wide range of applications including clinical therapeutic applications. In an embodiment, a method of using reversible thermal gel polymers comprises: (a) dissolving the reversible thermal gel polymers in a solvent to form a reversible thermal gel polymer formulation, wherein each of the reversible thermal gel polymer independently comprises: a first polymer block comprising first repeating units, wherein each of the first repeating units of the first polymer block independently comprise a hydrophilic group; and a second polymer block comprising second repeating units, wherein each of the second repeating units of the second polymer block independently comprise a thermosensitive group; wherein the first polymer block and the second polymer block are directly or indirectly covalently linked; wherein said reversible thermal gel polymers are dissolved in said solvent and have a concentration in the solvent selected from the range of 2% to 50% w/v, optionally 5% to 50% w/v, optionally 10% to 50% w/v, or optionally 20% to 40% w/v; and wherein the polymer formulation is characterized by a viscosity less than or equal to 1,500 cP; and (b) administering the polymer formulation to a target medium of the subject.

In an embodiment of the method of using, for example, the solvent is a sterile saline solution. In an embodiment of the method of using, for example, the concentration of the polymers in the polymer formulation is equal to or greater than 15% w/v. In an embodiment of the method of using, for example, the subject is a human or an animal other than a human. In an embodiment of the method of using, for example, the method further comprises connecting the syringe to a catheter, the catheter being connected to a vascular system of the subject. In an embodiment of the method of using, for example, the step of injecting comprises flowing the polymer through the catheter. In an embodiment of the method of using, for example, the target medium is an aneurysm. In an embodiment of the method of using, for example, the step of dispersing is performed at a temperature below 35° C. In an embodiment of the method of using, for example, prior to the step of injecting, the polymer formulation is stored at a temperature below 35° C. The target medium may be a target vessel.

In an embodiment of the method of using, for example, the step of injecting is performed such that the flow of polymer formulation through the catheter is continuous and at a rate greater than 0 mL per minute and less than or equal to 1 mL per minute. In an embodiment of the method of using, for example, the step of injecting comprises overfilling the target medium or vessel by 50% of the target medium or vessel volume.

In an embodiment of the method of using, for example, each of the polymers independently is characterized by formula (FX1):

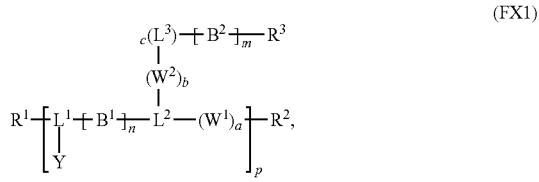
(FX1)

wherein:

$B^1$ is

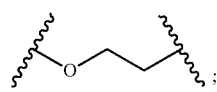
;

$B^2$ is z

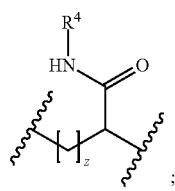
;

Y is selected from the group consisting of —OH, a radiopaque group, and a targeting ligand;
each of $L^1$ and $L^2$ is independently selected from the group consisting of $C_qH_{2q-1}$, $C_qH_{2q-1}X$, and $(C_rH_{r+2})X$;
X is O or S;
$L^3$, if present, is selected from the group consisting of a single bond, —$(CH_2)_q$—, —$(HCCH)_q$—, —$(CH_2CH_2X)_q$—, —$(CHXH)_q$—, —X—, —$NR^5$—, —CX—, —CXX—, —XCX—, —$XCX(CH_2)_qCXX$—, —$CXNR^5$—, —$NR^5CX$—, —$XCXNR^5$—, —$NR^5CXX$—, —$CX(CH_2)_qCR^5CN$—, —$(CH_2)_qX(CH_2)_r$—, —$(CH_2)_qXX(CH_2)_r$—, —$(CH_2)_qNR^5(CH_2)_r$—, —$(CH_2)_qCX(CH_2)_r$—, —$(CH_2)_qCXX(CH_2)_r$—, —$(CH_2)_qCXNR^5(CH_2)_r$—, —$(CH_2)_qNR^5CX(CH_2)_r$—, —$(CH_2)_qXCXNR^5(CH_2)_r$—, and —$(CH_2)_qNR^5CXNR^6(CH_2)_r$—;
each of $W^1$ and $W^2$, if present, is independently selected from the group consisting of a single bond, —$(CH_2)_q$—, —$(HCCH)_q$—, —$(CH_2CH_2X)_q$—, —$(CHXH)_q$—, —X—, —CXX—, —XCX, —CX—, —$XCX(CH_2)_qCXX$—, and —$NR^{11}$—;
each of $R^1$, $R^2$, $R^3$, and $R^4$ is independently selected from the group consisting of hydrogen, halide, and $C_1$-$C_5$ alkyl;
each of a, b, and c is independently 0 or 1;
each of q and r is an integer independently selected from the range of 1 to 10;
z is an integer selected from the range of 0 to 4;
m is an integer selected from the range of 1 to 10,000;
n is an integer selected from the range of 1 to 1,000;
p is an integer selected from the range of 1 to 1,000; and
each of $R^5$, $R^6$ and $R^{11}$ is independently selected from the group consisting of hydrogen, $C_1$-$C_{10}$ alkyl, $C_5$-$C_{10}$ aryl and $C_5$-$C_{10}$ heteroaryl.

In an embodiment, for example, the method of using the polymer formulation comprises embolizing the left atrial appendage alone or in tandem with another medical implant device. In an embodiment, for example, the method of using the polymer formulation comprises forming a topical wound dressing. In an embodiment, for example, the method of using the polymer formulation comprises forming a barrier between a medical device and an internal tissue. In an embodiment, for example, the method of using the polymer formulation comprises forming a space filler for cosmetic surgery. In an embodiment, for example, the method of using the polymer formulation comprises occluding a peripheral vein or an artery. In an embodiment, for example, the method of using the polymer formulation comprises embolizing an arteriovenous malformation.

In another aspect, the invention provides methods of making reversible thermal gel polymers having a wide range of compositions and molecular architectures. In an embodiment, a method of synthesizing a reversible thermal gel polymer comprises:

(a) polymerizing compound A with compound B, in the presence of a catalyst, to form polymer C, wherein:

compound A has the formula (FX8):

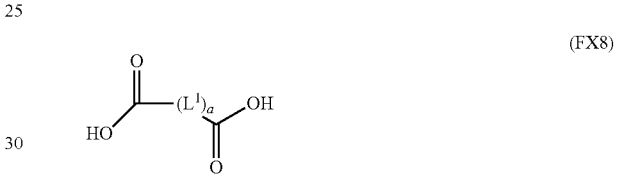
(FX8)

compound B has the formula (FX9):

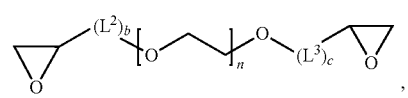
(FX9)

polymer C has the formula (FX10):

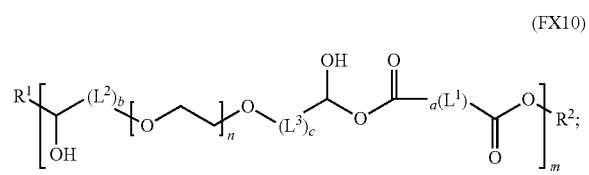
(FX10)

(b) polymerizing compound D in the presence of compound E to form polymer F, wherein:

compound D has the formula (FX11):

(FX11)

compound E has the formula (FX12):

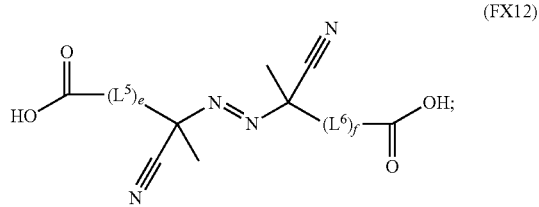
(FX12)

and polymer F has the formula (FX13) or (FX14):

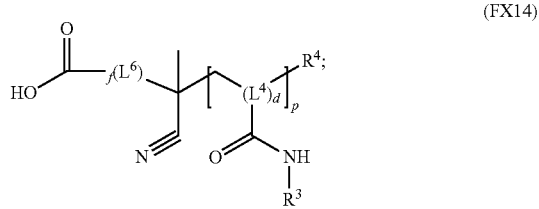
(FX13)

(FX14)

and (c) conjugating polymer F to polymer C to form the reversible thermal gel polymer, wherein:
the reversible thermal gel polymer has the formula (FX15) or (FX16):

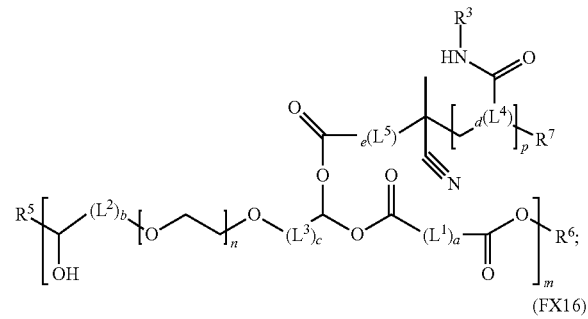
(FX15)

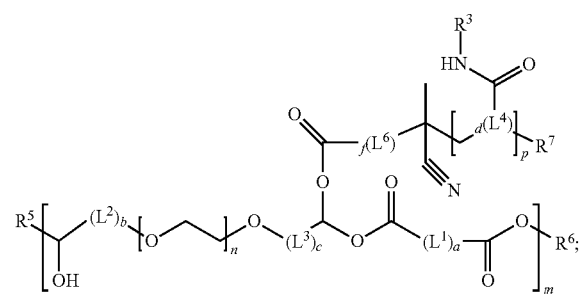
(FX16)

and
wherein:
m is an integer selected from the range of 1 to 1,000;
n is an integer selected from the range of 1 to 1,000;
p is an integer selected from the range of 1 to 10,000;
each of $L^1$, $L^2$, $L^3$, $L^4$, $L^5$, and $L^6$ is independently selected from the group consisting of —$(CH_2)_g$—, —$(HCCH)_g$—, —$(CH_2CH_2X)_g$—, —$(CHXH)_g$—, —X—, —CX—, —CXX—, —XCX—, —XCX$(CH_2)_q$CXX—, and —$NR^8$—;
X is O or S;
each of $R^1$, $R^2$, $R^3$, $R^4$, $R^5$, $R^6$, $R^7$, and $R^8$ is independently selected from the group consisting of hydrogen, halide, and $C_1$-$C_5$ alkyl; and
each of a, b, c, d, e, f, and g is an integer independently selected from the range of 0 to 4.

In an embodiment of the method of synthesizing, for example, the method further comprises conjugating a contrast agent or targeting group to the reversible thermal gel polymer. In an embodiment of the method of synthesizing, for example, the catalyst is triphenylphosphine. In an embodiment of the method of synthesizing, for example, step (c) is performed in the presence of dicyclohexylcarbodiimide and 4-(dimethylamino)pyridine. In an embodiment of the method of synthesizing, for example, step (c) further comprises a ratio of polymer C to polymer F selected from the range of 2:1 to 20:1. In an embodiment of the method of synthesizing, for example, step (a) is performed at 80 to 120° C. for 24 to 28 hours. In an embodiment of the method of synthesizing, for example, step (b) is performed at 50 to 90° C. for 1 to 5 hours. In an embodiment of the method of synthesizing, for example, step (c) is performed at 35 to 75° C. for 12 to 48 hours.]

In another aspect, the invention provides a reverse thermal gel block copolymer prepared by a method comprising:
(a) polymerization of compound A with compound B, in the presence of a catalyst, to form polymer C, wherein:
compound A has the formula (FX8):

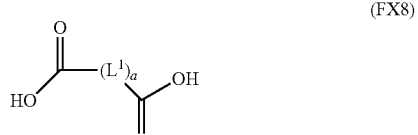
(FX8)

compound B has the formula (FX9):

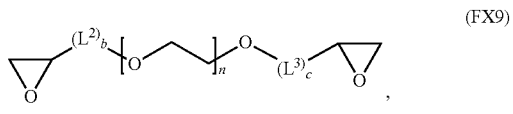
(FX9)

and
polymer C has the formula (FX10):

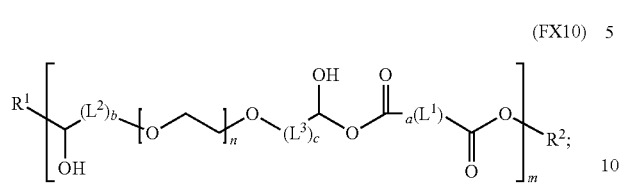
(FX10)

(b) polymerization of compound D in the presence of compound E to form polymer F, wherein:
compound D has the formula (FX11):

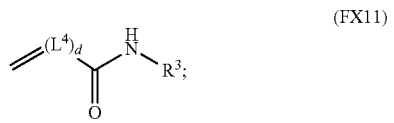
(FX11)

compound E has the formula (FX12):

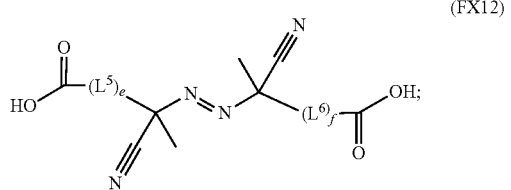
(FX12)

and polymer F has the formula (FX13) or (FX14):

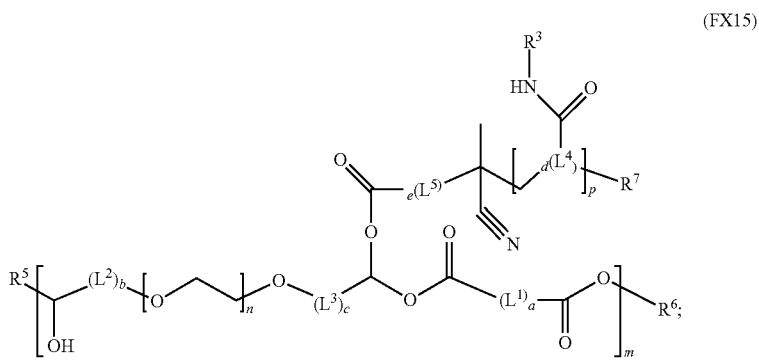

and (c) conjugation of polymer F to polymer C to form the reversible thermal gel polymer, wherein:

the reversible thermal gel polymer has the formula (FX15) or (FX16):

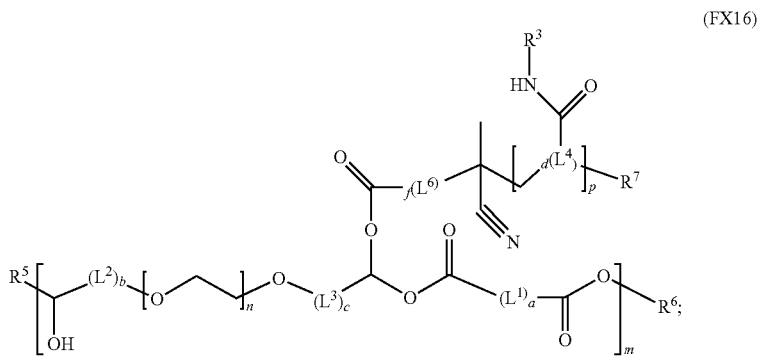

and
wherein:

m is an integer selected from the range of 1 to 1,000;
n is an integer selected from the range of 1 to 1,000;
p is an integer selected from the range of 1 to 10,000;
each of $L^1$, $L^2$, L, $L^4$, $L^5$, and $L^6$ is independently selected from the group consisting of —$(CH_2)_g$—, —$(HCCH)_g$—, —$(CH_2CH_2X)_g$—, —$(CHXH)_g$—, —X—, —CX—, —CXX—, —XCX—, —$XCX(CH_2)_qCXX$—, and —$NR^8$—;
X is O or S;
each of $R^1$, $R^2$, $R^3$, $R^4$, $R^5$, $R^6$, $R^7$, and $R^8$ is independently selected from the group consisting of hydrogen, halide, and $C_1$-$C_5$ alkyl; and
each of a, b, c, d, e, f, and g is an integer independently selected from the range of 0 to 4.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

STATEMENTS REGARDING CHEMICAL COMPOUNDS AND NOMENCLATURE

Figure 1:
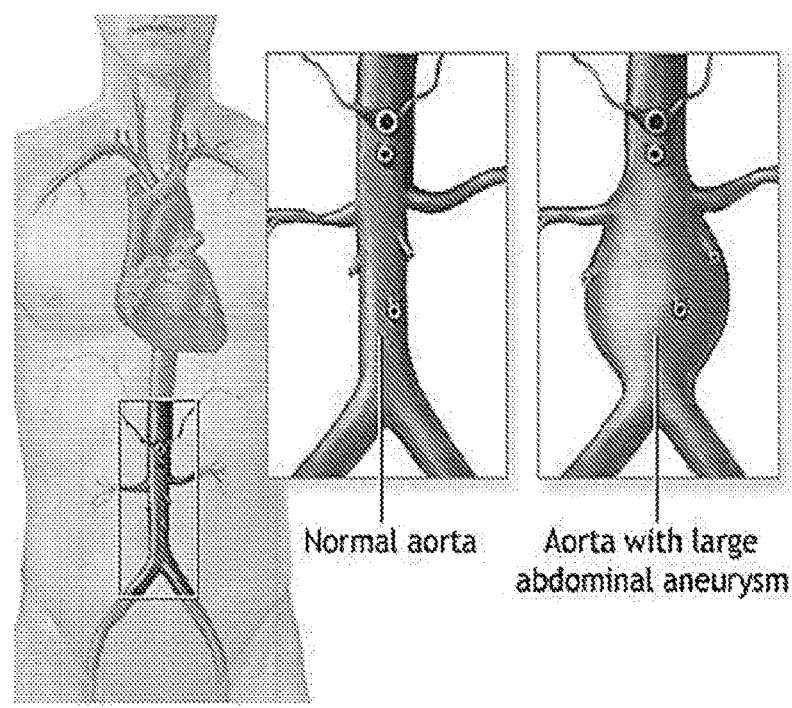
FIG. 1. Comparison of normal abdominal aorta with aortic aneurism [14].
Figure 2:
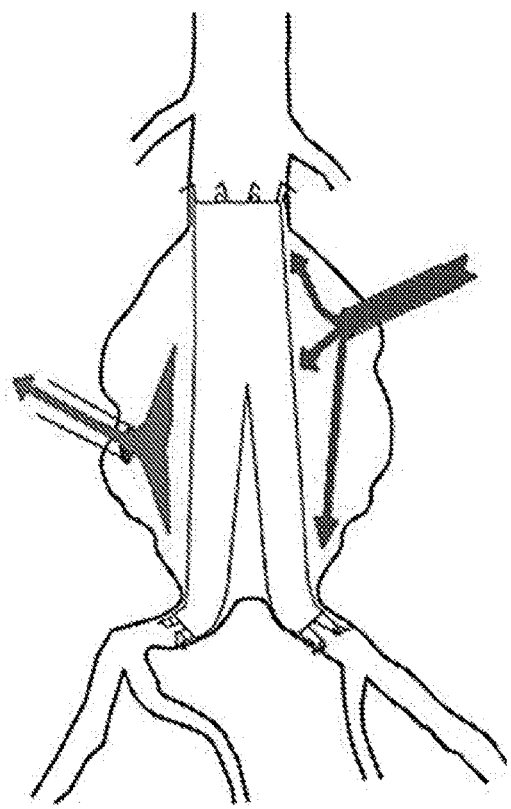
FIG. 2. Type II endoleak after EVAR [23]. If inflow occurs at a higher rate than outflow, continued enlargement of excluded aneurysm sac may occur.
Figure 3:
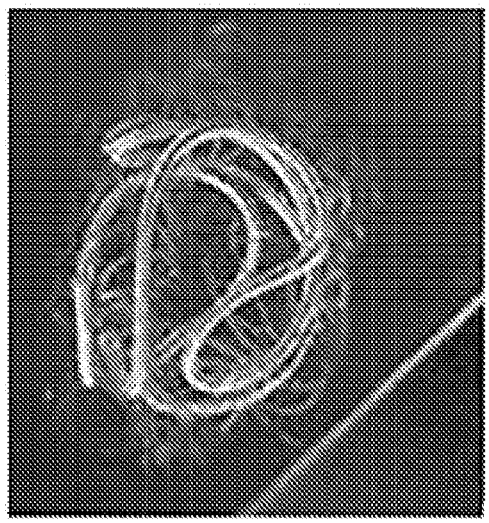
FIG. 3. Typical coil configurations include complex, straight, flat spiral and C-shaped. Note the fibrous attachments, which help increase thrombogenicity. Courtesy of Vaidya, et al. [1].
Figure 3:
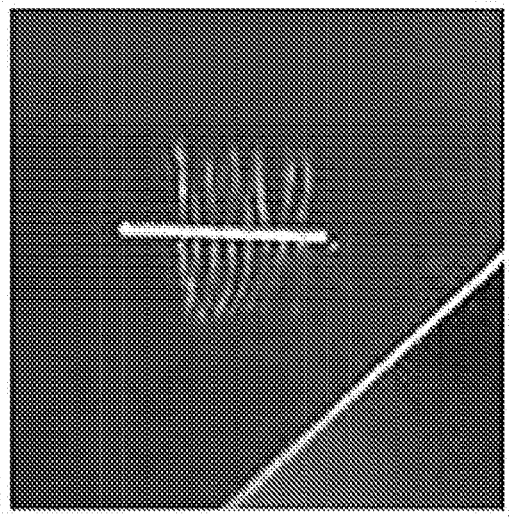
Figure 3:
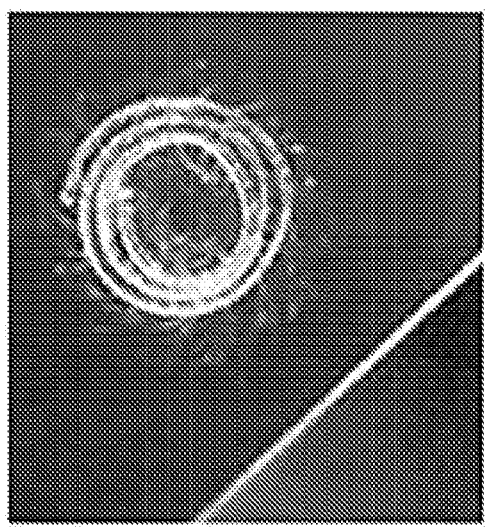
Figure 3:
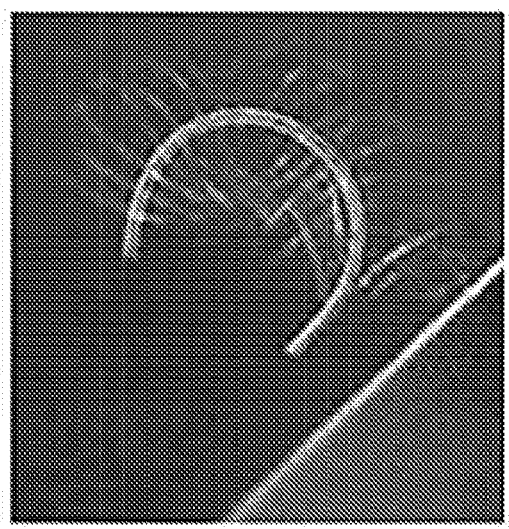

In general, the terms and phrases used herein have their art-recognized meaning, which can be found by reference to standard texts, journal references and contexts known to those skilled in the art. The following definitions are provided to clarify their specific use in the context of the invention.

In an embodiment, a composition or compound of the invention is isolated or purified. In an embodiment, an isolated or purified compound is at least partially isolated or purified as would be understood in the art. In an embodiment, the composition or compound of the invention has a chemical purity of at least 95%, optionally for some applications at least 99%, optionally for some applications at least 99.9%, optionally for some applications at least 99.99%, and optionally for some applications at least 99.999% pure.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 5,000 Da, in some embodiments greater than or equal to 20,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, alternating, segmented, grafted, tapered and other architectures. Useful polymers include organic polymers that may be in amorphous, semi-amorphous, crystalline or semi-crystalline states.

As used herein "hydrophilic" refers to molecules and/or components (e.g., functional groups, blocks of block polymers, etc.) of molecules having at least one hydrophilic group, and hydrophobic refers to molecules and/or components (e.g., functional groups of polymers, and blocks of block copolymers etc.) of molecules having at least one hydrophobic group. Hydrophilic molecules or components thereof tend to have ionic and/or polar groups, and hydrophobic molecules or components thereof tend to have non-ionic and/or nonpolar groups. Hydrophilic molecules or components thereof tend to participate in stabilizing interactions with an aqueous solution, including hydrogen bonding and dipole-dipole interactions. Hydrophobic molecules or components tend not to participate in stabilizing interactions with an aqueous solution and, thus often cluster together in an aqueous solution to achieve a more stable thermodynamic state.

An "oligomer" refers to a molecule composed of repeating structural units connected by covalent chemical bonds often characterized by a number of repeating units less than that of a polymer (e.g., equal to or less than 3 repeating units) and a lower molecular weights (e.g. less than or equal to 1,000 Da) than polymers. Oligomers may be the polymerization product of one or more monomer precursors.

"Block copolymers" are a type of copolymer comprising blocks or spatially segregated domains, wherein different domains comprise different polymerized monomers, for example, including at least two chemically distinguishable blocks. Block copolymers may further comprise one or more other structural domains, such as hydrophobic groups, hydrophilic groups, thermosensitive groups, etc. In a block copolymer, adjacent blocks are constitutionally different, i.e. adjacent blocks comprise constitutional units derived from different species of monomer or from the same species of monomer but with a different composition or sequence distribution of constitutional units.

"Diblock copolymer" refers to block copolymer having two different polymer blocks. "Triblock copolymer" refers to a block copolymer having three different polymer blocks, including compositions in which two non-adjacent blocks are the same or similar. "Pentablock" copolymer refers to a copolymer having five different polymer including compositions in which two or more non-adjacent blocks are the same or similar.

"Polymer backbone group" refers to groups that are covalently linked to make up a backbone of a polymer, such as a block copolymer. Polymer backbone groups may be linked to side chain groups, such as polymer side chain groups. Polymer backbones may terminate in a range of backbone terminating groups including hydrogen, $C_1$-$C_{10}$ alkyl, $C_3$-$C_{10}$ cycloalkyl, $C_1$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$SOR^{34}$, —$OSR^{35}$, —$SO_2R^{36}$, —$OR^{37}$, —$SR^{38}$, —$NR^{39}R^{40}$, —$NR^{41}COR^{42}$, $C_1$-$C_{10}$ alkyl halide, phosphonate, phosphonic acid, silane, siloxane, acrylate, or catechol; wherein each of $R^{30}$-$R^{42}$ is independently hydrogen, $C_1$-$C_{10}$ alkyl or $C_5$-$C_{10}$ aryl.

"Polymer side chain group" refers to a group covalently linked to a polymer backbone group that comprises a polymer side chain, optionally imparting steric properties to the polymer. In an embodiment, for example, a polymer side chain group is characterized by a plurality of repeating units having the same, or similar, chemical composition. A polymer side chain group may be directly or indirectly linked to the polymer back bone groups. In some embodiments, polymer side chain groups provide steric bulk and/or interactions that result in an extended polymer backbone and/or a rigid polymer backbone. Some polymer side chain groups useful in the present compositions include unsubstituted or substituted polyisocyanate group, polymethacrylate group, polyacrylate group, polymethacrylamide group, polyacrylamide group, polyquinoxaline group, polyguanidine group, polysilane group, polyacetylene group, polyamino acid group, polypeptide group, polychloral group, polylactide group, polystyrene group, polyacrylate group, poly tert-butyl acrylate group, polymethyl methacrylate group, polysiloxane group, polydimethylsiloxane group, poly n-butyl acrylate group, polyethylene glycol group, polyethylene oxide group, polyethylene group, polypropylene group, polytetrafluoroethylene group, and polyvinyl chloride group. Some polymer side chain groups useful in the present compositions comprise repeating units obtained via anionic polymerization, cationic polymerization, free radical polymerization, group transfer polymerization, or ring-opening polymerization. A polymer side chain may terminate in a wide range of polymer side chain terminating groups including hydrogen, $C_1$-$C_{10}$ alkyl, $C_3$-$C_{10}$ cycloalkyl, $C_1$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$SOR^{34}$, —$OSR^{35}$, —$SO_2R^{36}$, —$OR^{37}$, —$SR^{38}$, —$NR^{39}R^{40}$, —$NR^{41}COR^{42}$, $C_1$-$C_{10}$ alkyl halide, phosphonate, phosphonic acid, silane, siloxane acrylate, or catechol; wherein each of $R^{30}$-$R^{42}$ is independently hydrogen or $C_1$-$C_5$ alkyl.

Unless otherwise specified, the term "molecular weight" refers to an average molecular weight. Unless otherwise specified, the term "average molecular weight," refers to number-average molecular weight. Number average molecular weight is defined as the total weight of a sample volume divided by the number of molecules within the sample. As is customary and well known in the art, peak average molecular weight and weight average molecular weight may also be used to characterize the molecular weight of the distribution of polymers within a sample.

The term "weight-average molecular weight" ($M_w$) refers to the average molecular weight defined as the sum of the products of the molecular weight of each polymer molecule ($M_i$) multiplied by its weight fraction ($w_i$): $M_w = \Sigma w_i M_i$. As is customary and well known in the art, peak average molecular weight and number average molecular weight may also be used to characterize the molecular weight of the distribution of polymers within a sample.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "substituted" refers to a compound wherein a hydrogen is replaced by another functional group, including, but not limited to: a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate (ROP(=O)(OH)$_2$), an azo (RNNR'), a cyanate (ROCN), an amine (e.g., primary, secondary, or tertiary), an imine (RC(=NH)R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. In some embodiments, the term substituted refers to a compound wherein more than one hydrogen is replaced by another functional group, such as a halogen group.

As is customary and well known in the art, hydrogen atoms in chemical formulas are not always explicitly shown, for example, hydrogen atoms bonded to the carbon atoms of aromatic, heteroaromatic, and alicyclic rings are not always explicitly shown in chemical formulas. The structures provided herein, for example in the context of the description of chemical formulas and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups (e.g. $L^1$-$L^6$).

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as linking and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups, for example, as one or more linking groups (e.g. $L^1$-$L^6$).

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups (e.g. $L^1$-$L^6$).

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups (e.g. $L^1$-$L^6$).

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups (e.g. $L^1$-$L^6$).

As used herein, the terms "cycloalkenylene" and "cycloalkenylene group" are used synonymously and refer to a divalent group derived from a cycloalkenyl group as defined herein. The invention includes compounds having one or more cycloalkenylene groups. Cycloalkenylene groups in some compounds function as linking and/or spacer groups. Compounds of the invention include substituted and/or unsubstituted $C_3$-$C_{20}$ cycloalkenylene, $C_3$-$C_{10}$ cycloalkenylene and $C_3$-$C_5$ cycloalkenylene groups, for example, as one or more linking groups (e.g. $L^1$-$L^6$).

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups (e.g. $L^1$-$L^6$).

As used herein, the term "halo" refers to a halo group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

As used herein, the term "targeting group" or "targeting ligand" refers to a group capable of providing molecular recognition and/or tissue specific targeting functionality. Targeting groups useful in the invention include an aptamer, a polypeptide, a protein, a oligonucleotide, a carbohydrate, an antibody or other biomolecule, or fragments or fusions thereof.

As used herein, the term "radiopaque group" refers to the relative inability of electromagnetic waves, such as X-rays, to pass through the chemical group or compound. The presence of a radiopaque group allows the molecule to appear opaque/white in a radiographic image. In an embodiment, a radiopaque group is a singly or multiply halogen substituted compound selected from the group consisting of $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, $C_3$-$C_{10}$ arylene, $C_3$-$C_{10}$ heteroarylene, $C_2$-$C_{10}$ alkenylene, $C_3$-$C_{10}$ cycloalkenylene, $C_2$-$C_{10}$ alkynylene, and any combination thereof. In an embodiment, the halogen substituted compound has a pendant halide or a pendant amine group. For example, a radiopaque group is iodobenzoyl chloride.

As used herein, the term "polydispersity index" can be calculated as $M_w/M_n$, where $M_w$ is the weight-averaged molar mass and $M_n$ is the number-averaged molar mass of the polymer.

As used herein, "contrasting agent" refers to a substance or chemical group used to enhance the contrast of fluids within the body during medical imaging, such as to monitor the flow of a fluid injected into a vessel, including an aneurysm.

As used herein, the term "thermosensitive" refers to a temperature-responsive or thermoresponsive polymer that exhibits significant and, optionally discontinuous, change of their physical properties with temperature, such as a change in phase, or physical property.

As used herein, the term "low critical solution temperature" refers to the phase transition temperature at which the reversible thermal gel polymer transitions between a free-flowing liquid state and a non-flowing, semi-solid gel state.

As used herein, the term "% w/v" refers to a measurement of concentration wherein 1% w/v equates to 1 g of solute per a total volume of 100 mL of solution.

As used herein, the term "injection force" refers to force require to inject a polymer formulation through a syringe, wherein the syringe may be attached to a catheter.

As used herein, the term "French" refers to the unit of measure of the outer diameter of a catheter, wherein 1 French (Fr)=0.333 mm=0.013 in.

As used herein, the term "target medium" refers to the medium into which the polymer formulation is administered. Target medium may be an in vivo medium or an in vitro medium In an embodiment, for example, a target medium is a tissue and/or biofluid of a subject, such as a human or other animal. In an embodiment, for example, a target medium is a vasculature tissue, cardiac tissue, connective tissue, muscle tissue, nervous tissue, brain tissue or central nervous system tissue. In an embodiment, for example, a target medium is an organ or any portion thereof.

As used herein, the term "co-solvent" refers to a substance that can dissolve or disperse a polymer, wherein the volume of the co-solvent in the solution is less than that of the solvent.

As used herein, the term "maximum volumetric shrinkage" refers to the relative reduction in volume of the polymer after it is injected into a target medium or vessel, for example.

As used herein, the term "vascular system" refers to the network of blood vessels within the human or animal body.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids. Peptides are comprised of two or more amino-acid connected via peptide bonds.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Compositions of some embodiments of the invention comprise alkyl groups as terminating groups, such as polymer backbone terminating groups and/or polymer side chain terminating groups.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6- or 7-member aromatic rings, including heterocyclic aromatic rings. The term heteroaryl specifically refers to aryl groups having at least one 5-, 6- or 7-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As to any of the groups described herein which contain one or more substituents, it is understood that such groups do not contain any substitution or substitution patterns which are sterically impractical and/or synthetically non-feasible. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine;

pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

Many of the molecules disclosed herein contain one or more ionizable groups. Ionizable groups include groups from which a proton can be removed (e.g., —COOH) or added (e.g., amines) and groups that can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diastereomers, enantiomers, tautomers and mixtures enriched in one or more stereoisomer. The scope of the invention as described and claimed encompasses the racemic forms of the compounds as well as the individual enantiomers and non-racemic mixtures thereof.

As to any of the above groups which contain one or more substituents, it is understood that such groups do not contain any substitution or substitution patterns which are sterically impractical and/or synthetically non-feasible.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

Example 1: Optimization of a PEGSA-PNIPAm Reverse Thermal Gel for Treatment of Abdominal Aorta Type II Endoleaks Abstract:

Background: Type II endoleaks are complications associated with endovascular aortic repair that can have serious consequences if left untreated. Two commercially available varieties of liquid embolic agents used for type II endoleak repair are in situ polymerizing n-butyl cyanoacrylate (n-BCA) and precipitation polymerizing ethylene vinyl alcohol copolymer (Onyx). These products have significant drawbacks including systemic toxicity, migration of the embolic agent throughout the circulatory system and catheter entrapment during delivery [1]-[3]. Thermosensitive polymers such as reversible thermal gels (RTGs) hold promise as alternative embolic agents due to enhanced biocompatibility and the ability to be delivered as an aqueous solution via intravenous catheterization, forming a solid gel only upon reaching body temperature [4]. This study describes the characterization, modeling and optimization of a novel RTG liquid embolic material.

Methods: Analytical modeling of pressure drop across a catheter and heat transfer characteristics of the RTG during delivery was used to optimize the synthetic design of the polymer. Bulk polymer structural properties, RTG physical properties, cytotoxicity and degradation analysis were carried out to determine the critical properties and biocompatibility profile of the material. In vitro testing was conducted to assess the potential for microcatheter delivery and feasibility as an embolic agent.

Results: A 15% (w/v) concentration of RTG in phosphate-buffered saline was manually injectable through a 1.9 French microcatheter (155 cm length, 1 mL syringe, 1 mL/min flow rate). Reducing the molecular weight of the polymer also reduced the aqueous solution viscosity. Increasing the polymer concentration reduced the volumetric shrinkage. RTG extract was assessed using a calcein/ethidium live/dead cell viability assay and showed no significant decrease in cell viability compared to control media (human umbilical cord vein endothelial cells). Mass loss due to hydrolytic and oxidative degradation was observed to plateau after 6 days, and assessment of the degradation products showed no cytotoxicity compared to control media. Analytical model results of the injection forces required for delivery and heat transfer profile of the system correlated well with the experimental results.

Conclusion: Preliminary in vitro tests indicate this RTG material is a viable alternative to current liquid embolic agents on the market. Potential application areas include treatment of type II endoleaks, cerebral arteriovenous malformations and varicose veins.

Nomenclature:

| | | | |
|---|---|---|---|
| AAA | Abdominal aortic aneurysm | LCST | Low critical solution temperature |
| AVM | Arteriovenous malformation | NMR | Nuclear magnetic resonance |
| DSC | Differential scanning calorimetry | PEGSA | Poly(ethylene glycol) succinic acid |
| EVAR | Endovascular aortic repair | PNIPAm | Poly(N-isopropyl-acrylamide) |
| FTIR | Fourier transform infrared spectroscopy | PBS | Phosphate-buffered saline |
| GPC | Gel permeation chromatography | RTG | Reverse thermal gel |
| HUVEC | Human umbilical vein endothelial cell | | |

Introduction: An abdominal aortic aneurysm (AAA) is a life-threatening condition characterized by a localized enlargement of the abdominal aortic vessel of more than 1.5 times the normal vessel diameter. Aneurysm rupture results in more than 13,000 deaths in the United States annually [5]. When detected early, AAA can be treated using a minimally invasive technique called endovascular aortic repair (EVAR). In this procedure, a stent-graft deployed at the site of the aneurysm acts as a conduit to restore normal blood flow to the region, alleviating pressure on the aneurysm [5].

Type II endoleaks are complications associated with EVAR, where retrograde blood flow from aortic branch vessels results in sustained enlargement of the excluded aneurysm sac [6]. In cases where the risk of rupture persists due to an unresolved type II endoleak, transarterial or translumbar embolization using coils, glues or other embolic agents may be required to alleviate the condition.

Liquid embolic agents have attracted considerable attention for the treatment of vascular abnormalities. Two primary categories of commercially available liquid embolic agents are in situ polymerizing n-butyl cyanoacrylate (n-BCA) and precipitation polymerizing ethylene vinyl alcohol copolymer (Onyx). N-BCA is a liquid adhesive monomer that forms a rigid polymer matrix upon contact with ionic compounds, such as blood [7]. Onyx is composed of ethylene vinyl alcohol copolymer (EVOH) dissolved in dimethyl sulfoxide (DMSO). Upon delivery to the target vessel, DMSO diffuses into the bloodstream and EVOH solidifies in an outside-to-in fashion, creating a cast of the vessel region [1]. Unfortunately, these materials have significant drawbacks including systemic toxicity, migration of the embolic agent throughout the circulatory system, catheter adhesion and catheter entrapment during delivery [1]-[3]. Reverse thermal gels (RTGs) are a class of stimuli-responsive hydrogels composed of hydrophobic and hydrophilic copolymers [8]. These materials are water dispersible and undergo a fully reversible solution-to-gel phase transition in response to elevated temperatures [9]. RTGs hold promise as alternative embolic agents for vascular occlusion, treatment of type II endoleaks and other space-filling applications due to enhanced biocompatibility and ability to be delivered as an aqueous solution via intravenous catheterization.

The RTG developed for this example embodiment was composed of poly(ethylene glycol) diglycidyl ether, succinic acid and poly(N-isopropylacyrlamide) (PEGSA-PNIPAm). This report describes the development and optimization of this example RTG for embolic applications. The studies evaluate that PEGSA-PNIPAm, in an embodiment, dispersed in water at 15% (w/v) is delivered through a 3 French microcatheter (0.67 mm ID, 150 cm length), transitions to a gel between 32-37° C. and is non-cytotoxic.

FDA regulations and specific clinical applications often dictate key design criteria when developing novel medical devices or biomaterials. In the case of alleviating complications associated with AAA repair, traditional embolic materials are not without limitations. One way to address the problems of these current materials is through the development of customizable RTGs. The physical properties of these polymers are highly customizable and have the potential to advance the field of target embolization by offering enhanced biocompatibility, bioactivity, degradability, radiopacity and drug delivery capabilities [10]. Specifically, this study focused on optimizing a PEGSA-PNIPAm RTG for the treatment of type II endoleaks in patients with repaired AAA. Key aspects of the study included improving in vitro handling and delivery properties, maintaining biocompatibility and designing characterization studies that are compliant with FDA biocompatibility guidelines and ISO 10993-1.

AAA is a significant cardiovascular disease affecting more than 1.1 million individuals in the United States [11]. Aneurysm rupture has a high association of mortality and results in more than 13,000 deaths annually [5]. Approximately 45,000 repair procedures are performed each year, and it is estimated that endovascular repair accounted for 75% of all repair procedures [5], [12]. Roughly 20% of patients who have undergone endovascular repair experience type II endoleaks, meaning nearly 7,000 patients with type II endoleaks may require an additional embolization procedure annually [6]. Therefore, successful development of this RTG has the potential to reduce healthcare costs, improve quality of life and decrease mortality rates in patients who are candidates for this treatment.

Embodiments of the reverse thermal gel polymers described in this study have applications beyond the treatment of type II endoleaks. An example includes effective space filling or sealing of areas with blood leakage around the margins of the endovascular graft, such as in type I endoleaks. The RTG may also be effective in treating arteriovenous malformations (AVMs) and cerebral aneurysms. The reported incidence of cerebral aneurysms in the United States is approximately 30,000 cases annually [13]. In such applications with highly complex vessel architecture, optimization of the RTG for microcatheter delivery is key for achieving therapeutic results. Other peripheral vascular occlusion applications such as varicose vein treatment may benefit from the use of certain embodiments of the RTGs described herein. Eliminating the need for laser ablation and tumescent solutions would lower costs and reduce patient discomfort.

Background and Review of the Literature:

AAA and Type II Endoleaks:

The abdominal aorta is the primary artery that supplies oxygenated blood to the abdomen, pelvic region and legs. Anatomically, it is a continuation of the thoracic aorta, descends centrally through the retroperitoneum and bifurcates into the common iliac arteries downstream of the kidneys and upstream of the pelvis. AAA is characterized by an enlargement or focal dilation within the abdominal aorta equal to or greater than 1.5 times the proximal normal vessel diameter of 3 cm.

The disorder typically affects people between 65 and 85 years of age and is four times more prevalent in men than women [15]. In general, the threshold for open or endovascular repair is a vessel diameter greater than 5.5 cm in men and 5.0 cm in women [5]. The patient is usually asymptomatic until a leak or rupture occurs, upon which mortality is estimated between 59% and 83% if the patient is unable to reach the hospital and undergo emergency surgery [16]. Even if the patient does receive surgical treatment for a rupture, the likelihood of survival is between 50% and 70% [5]. The pathogenesis of AAA is not well understood, but multiple genetic and environmental factors including age, gender, smoking, family history and hemodynamic factors play a role in the development of AAA. Although some studies suggest that atherosclerosis may be a cause of AAA due to presence of plaque buildup in aneurysmal walls, more recent studies indicate that atherosclerosis may instead develop in parallel with arterial dilation [16], [17]. Due to poor understanding of AAA pathogenesis and the fact that rupture is so deadly, it is critical to develop techniques to diagnose and treat aneurysms before rupture occurs.

AAA can be detected via abdominal radiograph, ultrasound, computed tomography angiography (CTA), and MRI. CTA is widely considered the best imaging modality for diagnosis of AAA because it can accurately demonstrate the size and shape of the aneurysm and can be used to measure aneurysmal growth over time [18]. CTA is a valuable diagnostic tool when surgical treatment is being considered. The treatment of AAA involves either open surgical repair (OSR) or endovascular aortic repair (EVAR). The process of open surgery involves making a transverse incision in the abdomen. Once the abdominal cavity is open, the aorta is clamped on both sides of the aneurysm to maintain control of surrounding vessels and a synthetic graft is fixed in place by the surgeon, thereby reducing pressure on the aneurysm and allowing for reintroduction of normal blood flow to the area. PTFE, Dacron, and polyester are primary materials that make up synthetic open surgical repair grafts [19]. For patients who are not candidates for OSR, EVAR is a less invasive alternative, with a 30 day mortality rate of 1% compared with 4-5% for OSR. EVAR currently accounts for approximately 75% of all cases of surgical repair of AAA in the United States [5]. During the EVAR procedure a covered stent-graft is introduced percutaneously via the femoral artery and is anchored to normal sections of the aortic and iliac walls. The stent expands and acts as an artificial conduit within the vessel, excluding blood flow from the outer areas of the aneurysmal sac. EVAR stents are typically made of two or more conjoined stents made of nitinol or stainless steel surrounded by graft fabric composed of woven polyester or expanded PTFE [20]. Catheterization is used to deploy the stent-graft to the aneurysm.

Although short term mortality rates are reduced for patients having undergone EVAR compared to OSR, survivability rates after 1 to 3 years are roughly the same for each treatment strategy. Additionally, nearly 30% of patients required additional surgery 6 years after initial EVAR [5]. The most common complications requiring secondary intervention are endoleaks, which are characterized by persistent blood flow within the excluded aneurysm after EVAR treatment has been applied. Endoleaks have five different classifications, described in Table 1.

TABLE 1

Endoleak classifications [21]:
Types of Endoleaks

| Type I | Marginal leakage at the graft attachment site; either proximal or distal end |
| Type II | Retrograde blood flow into excluded aneurysm from one or more branch vessels |
| Type III | One or more defects in the graft causes leakage into the excluded aneurysm |
| Type IV | Graft porosity results in leakage through the graft |
| Type V | Continued expansion of the aneurysm without evidence of a leak upon imaging |

Type II endoleaks are the most frequent complications, comprising approximately 80% of endoleak cases. It is estimated that of all patients who have undergone EVAR, 19-22% experience type II endoleaks [6]. Type II endoleaks can be complex vascular structures with multiple inflow and outflow branch vessels extending from the aneurysm and often cause retrograde blood flow into the excluded aneurysmal sac. Although some type II endoleaks will thrombose and heal naturally, if persistent inflow and outflow vessels remain open, the aneurysm has the potential to remain active and increase in size, eventually requiring secondary intervention. Nevala et al. studied the effectiveness of treating type II endoleaks in 218 patients who had undergone EVAR within a 5 year period from 2000-2005 [22]. Out of this patient group, they found that 47 patients (22%) developed type II endoleaks during a 5 year follow-up period. Of those 47 patients, 14 had endoleaks severe enough to require secondary intervention. A wide variety of embolic materials were used for the procedures including Onyx liquid embolic, glue, gelatin, thrombin and coils. Interestingly, the procedure was deemed successful (prevention of continued enlargement of aneurysmal sac) in only 38% of these patients. Although a relatively small sample size, the results of this study suggest that currently available embolic materials are inadequate when secondary intervention is required to treat type II endoleaks.

Overview of Endovascular Embolization and Polymer-Based Embolic Materials:

Endovascular embolization is the deliberate occlusion of a vessel via introduction of either a natural or artificial particulate mass. The goal of the embolization procedure is to drastically reduce blood flow (or induce complete stasis) such that an intravascular thrombus, or clot, forms around the embolic material [24]. Platelets are recruited to the site where the embolic material has been deployed. Platelet adhesion and aggregation continues, increasing the size of the thrombus until the vessel is completely occluded.

Treatment of type II endoleaks is accomplished through target embolization of the vessel(s) causing the leak. Transarterial and translumbar embolization are the most common approaches for treating type II endoleaks. Transarterial embolization utilizes catheters to deliver embolic agents or coils to the vessels of interest to induce thrombosis [25]. Briefly, contrast angiography is used to localize both the inflow artery and outflow artery keeping the endoleak active. Next, a catheter is inserted into the femoral artery and advanced through proximal arteries to the active outflow vessel, at which point the embolic agent is deployed. If necessary, additional embolic material is delivered to the excluded aneurysm space between the vessel wall and the stent. Finally, the inflow artery is embolized. Contrast is injected throughout the procedure to confirm complete endoleak repair.

Translumbar embolization is a more direct approach where the surgeon inserts a 19-gauge 20 cm needle into the posterior thoracic region at the height of the endoleak, directly puncturing the aneurysm sac. The embolic material is then released and communication between the feeding vessels is eliminated [26].

Types of embolic materials include coils, glues, foams, particles, polymers and gels. The use of coils for embolization was first reported in 1975 for the treatment of AVM [27]. Coils are typically stainless steel or platinum and can be coated with a variety of fibrous materials such as nylon, polyester, Dacron or polymeric hydrogels [28]. The premise of embolic coils is to slow blood flow, induce chronic inflammatory response and cause eventual thrombosis of the aneurysm or target vessel. Disadvantages of the coil technique include the risk of migration, occlusion of non-target vessels, infection and vessel perforation [3].

NBCA is a commercially available mixture of liquid monomer N-butyl-2 cyanoacrylate, ethiodiol, (a delivery vehicle and polymerization suppressant) and contrast agent. When NBCA is delivered to an anionic environment such as blood, polymerization will occur [29]. NBCA has been used in cerebral and spinal AVMs and embolization of type II endoleaks after EVAR of AAA [30]. However, due to the fast polymerization time of NBCA, catheter entrapment and occlusion are common.

Radiopaque compounds are important for localizing the target vessels as well as the endoleak and for monitoring embolization during the procedure. Examples include iodinated compounds such as iohexol, and non-ionic compounds such as iopamidol (Isovue) and iodixanol (Visipaque). To date, few embolic materials have covalently bound radiopaque contrast agents [31]. The vast majority of materials require the contrast agent to be dispersed in solution prior to delivery. This increases the overall viscosity of the system and can make it difficult for the surgeon to deliver the material through a microcatheter. Additionally, contrast agents such as tantalum powder (Onyx) can obscure the tip of the catheter during the embolization procedure, leading to the potential embolization of non-target areas [32]. Furthermore, radiopaque contrast remains in the embolic material post-op and produces attenuation and beam-hardening artifacts on CTA that can interfere with the image quality and limit the diagnostic value of post-procedure images [32].

Onyx Liquid Embolic:

Onyx is a liquid embolic agent that has been used since 1990 and received FDA approval in 2005 for the treatment of cerebral AVMs [1]. It is composed of ethylene vinyl alcohol copolymer (EVOH) dissolved in dimethyl sulfoxide (DMSO) along with a contrast agent (micronized tantalum powder). Catheterization is used to deliver the material to the target vessel. Upon injection, the DMSO diffuses into the bloodstream, causing the EVOH to solidify and induce thrombosis. Onyx exhibits lava-like flow once injected into the vessel. In the treatment of AVM's, Onyx is injected upstream of the nidus, which allows the onyx to be carried downstream into the nidus and perfuse into the smaller vasculature as it solidifies. This procedure is often repeated multiple times to completely occlude all communicating vessel feeding the AVM.

Onyx has recently been described for the treatment of type II endoleaks in patients who have undergone an EVAR procedure for AAA [25]. Massis et al. studied the effectiveness of Onyx for treating type II endoleaks in 101 patients from 2006-2011. Either a transarterial or a translumbar approach was used depending on the location of the endoleak. In each case angiography was used to characterize the endoleak and determine the vessels involved. Subsequently, Onyx was delivered to the site via catheterization (transarterial approach) or needle injection (translumbar approach) with the goal of complete occlusion of the vessels involved. The results showed that 66% of patients were successfully embolized using the transarterial approach, meaning that delivery of Onyx to the intended target site was achieved. Upon 15 week follow-up, 74% saw stabilization or decreased size of the excluded aneurysm. The results of this study are significant because they show that Onyx, which is considered one of the better liquid embolics currently on the market, is reasonably effective in treating type II endoleaks and maintaining long-term stability of the aneurysm. However, this study does not address some of the disadvantages of this material with regard to acute toxicity.

Onyx is advantageous over other certain embolic agents because it more readily conforms to the space of the aneurysm or target vessel, it is non-adhesive allowing for a longer setting time, and the product comes in three different concentrations. This allows for a higher degree of versatility in controlling the viscosity based on the application and the target vessel size. Disadvantages of Onyx arise from the DMSO carrier, which can cause systemic toxicity, vasospasm and necrosis in high doses and has been shown to have action potential reducing effects [2]. Additional complications include acute respiratory distress syndrome, microcatheter gluing, and pulmonary and cardiac migration of Onyx [33], [34].

Upcoming Liquid Embolics:

The development of bioengineered "smart" materials has increased dramatically over the past decade. Consequently, a wide array of experimental liquid embolics have been reported in the literature in recent years. These can generally be broken down into three categories: in situ polymerizing, precipitation polymerizing, and temperature-sensitive hydrogels. Appendix 1 provides advantages, disadvantages, and an indication of the polymerization safety profile for several of these materials.

Experimental in situ polymerizing materials are mechanistically similar to NBCA, forming a rigid polymer matrix upon contact with blood, saline or other ionic substances. PPODA-QT is an thiol-acrylate-based system that forms a chemically crosslinked, non-degradable gel when combined with a contrast agent [10], [35]. The material is non-degradable, non-adhesive and the gelation time can be modulated. However, the high pH of the initiating solution can by cytotoxic, and further assessment of the degree of conversion and safety of the starting monomers is required.

Coacervates and liquid crystal polymers have also been proposed as experimental in situ polymerizing embolics. Coacervates form upon contact of aqueous solutions of polyphosphate and divalent cations ($Ba^{2+}$, $Ca^{2+}$, $Sr^{2+}$) [36]. They have been shown to be biocompatible, resorbable and inherently radiopaque. However, they require a dual-lumen catheter for injection. Liquid crystal phytantriol has been synthesized by Qin, et al. as a drug-eluting liquid embolic. They have shown successful delivery through 0.035" ID catheter, as well as 30 days of sustained in vitro drug release [37]. The disadvantage of this material is that it requires organic solvent for dispersion and delivery.

Similar to Onyx, several precipitating polymer embolics have been reported in the literature. Precipitating Hydrophobic Injectable Liquid (PHIL) has been approved for clinical use in Europe and is composed of poly(lactide-co-glycolide) and poly(hydroxyl ethyl methacrylate) dispersed in DMSO [10]. It has a conjugated radiopaque compound for visualization, and has been used for endovascular treatment of brain AVMs, showing good penetration, less reflux and faster polymerization time than Onyx [38]. Alginate is derived from natural polysaccharides and forms a biocompatible hydrogel upon exposure to $Ca^{2+}$ ions [10]. It is non-adhesive, water soluble and forms an immediate and stable gel upon injection. Although alginates typically have high viscosities, they display shear-thinning behavior and the viscosity can be adjusted based on alginate concentration in water [39]. Becker, et al. demonstrated successful filling of artificially created aneurysms in swine, with stability and healing for 90 days [40].

Temperature-sensitive hydrogels have attracted attention for favorable biocompatibility and the capacity for water dispersion rather than the need for organic solvents. These materials will be described in more detail below.

Nellix endovascular aneurysm sealing system attempts to block retrograde flow into the aneurysm by using polymer filled "endobags" that surround expandable stents and can be deployed to fill the entire aneurysm cavity [41]. This material is currently approved for investigational use and has been shown to be effective in treating patients with AAA.

Recently, Avery et al. demonstrated in vitro occlusion of artificial vessels, as well as murine and porcine endovascular occlusion using a shear-thinning biomaterial comprised of gelatin and silicate nanoplatelets, the latter of which have been shown to promote clotting [42], [43]. The material showed decreased viscosity under shear stress, modulus recovery after exposure to high strain and no catheter blockage during injection. It formed a complete vessel cast after injection, and no migration or fragmentation of the material was observed over a 15 minute period during porcine lumbar and internal iliac artery embolization. Disadvantages of the material include high initial viscosity, high injection force required to deliver the material through a 4 F catheter and significant reflux during injection.

Reverse Thermal Gels as Prospective Embolic Materials:

An alternative approach for the treatment of type II endoleaks is to use RTGs as the embolic agent. RTGs make up a subset of stimuli-responsive hydrogels which, unlike conventional polymers that transition from a rubbery to glassy state with decreasing temperature, undergo rapid changes in solubility upon heating, driving a transition from a free-flowing liquid state to a non-flowing, semi-solid gel state [44]. The temperature at which the gel state occurs is known as the low critical solution temperature (LCST). This process is fully reversible: as the temperature is reduced below the LCST, the material returns to its previous solution state. The synthetic composition of the RTG dictates where this phase transition will occur and physiologically relevant systems are specifically designed to gel at or slightly below body temperature. RTGs are advantageous because they can be injected through small needles or catheters at room temperature and will not gel until they are in vivo. Furthermore, they can be functionalized to enable conjugation of radiopaque compounds or biomolecules such as peptides and carbohydrates to promote positive cell-to-biomaterial interactions [9], [31].

Synthesis of RTGs:

RTGs include branched, di-block or multi-block copolymers containing hydrophobic, hydrophilic and thermally-responsive constituents. PNIPAm is an established and well understood amphipathic, thermo-responsive polymer that has been used in a variety of RTG materials [8], [31], [45]-[47]. It contains both amide (hydrophilic) and isopropyl (hydrophobic) groups and when dispersed in an aqueous solution exhibits abrupt inverse solubility at an LCST of 32° C. [48]. At temperatures below the LCST the material remains in a clear liquid state due to swelling of the polymer chains. Conversely, above the LCST, a thermoreversible phase separation occurs as the hydrophobic isopropyl groups self-assemble due to entropic changes in the system. When combined with other monomers such as N,N'-methylenebisacrylamide (MBAm), a thermally-responsive, covalently crosslinked hydrogel is formed that exhibits volume changes as external temperature rises above the LCST [46].

Other types of thermally sensitive polymers have been developed with the intent of being used as delivery systems. Much of these materials are based on block copolymer synthesis of hydrophobic and hydrophilic constituents. For example, poly(ethylene oxide)-poly(propylene oxide)-poly (ethylene oxide) (PEO-PPO-PEO, aka Pluronic), and poly (butylene oxide)-PEO-poly(butylene oxide) (PBO-PEO-PBO) are capable of undergoing a reversible sol-gel transition when heated or cooled above or below the LCST [49]. Biodegradable polymers including poly(lactic acid-co-glycolic acid) (PLGA) and polycaprolactone (PCL) can be combined with PEO to create a thermoreversible block copolymer capable of degrading over time in vivo [50]. The LCST of RTGs can be modulated based on the chain length of each block, the ratio of hydrophobic to hydrophilic components, and the concentration of the RTG in solution.

RTGs can be synthesized in a number of ways. Park et al. used an alcohol-isocyanate reaction to form a hydrophobic polyurethane intermediate polymer, followed by PEGylation of the intermediate to form the hydrophilic component and the resulting RTG block copolymer [9]. Ring-opening polymerizations are typically used for preparation of carboxy anhydrides or lactides with polyethylene glycol (PEG) [50]. For synthesis of RTGs containing PNIPAm, a thermal free-radical polymerization is used to form the PNIPAm polymer, which is subsequently carboxylated and added to an amine-containing copolymer [8]. Similarly, many naturally occurring polymers have been used in the design of thermally responsive materials. Chitosan, when combined with β-glycerophosphate disodium salt has been shown to exhibit gelation at 37° C. [51]. Additionally, secondary functionalization may also be incorporated into these RTG polymers, allowing for conjugation of specific biomolecules. Pena, et al. designed a heparin-mimicking RTG that contained negatively charged sulfonate groups which aided in therapeutic protein delivery while preserving bioactivity of those proteins.

A limited number of recent studies have explored the possibility of using in situ, thermally-gelling materials for embolic applications. In 2005 Vernon et al. investigated a variety of PNIPAm-co-acrylic acid polymers with LCSTs between 32° C. and 39° C. for use in brain AVMs [52]. His group examined the relationship between gel strength at body temperature to solution viscosity at room temperature using differential scanning calorimetry (DSC) and rheometry. They found that a lower molecular weight polymer resulted in a lower solution viscosity at room temperature compared to higher molecular weight variations. Furthermore, they demonstrated that the low molecular weight polymers also displayed clinically relevant gel strengths at body temperature. These findings are useful for designing robust materials that can be delivered through small bore catheters.

More recently, Lee et al. reported on the development of a radiopaque, thermosensitive PNIPAm-based polymer for embolization procedures [31]. The group synthesized a Poly(N-isopropylacrylamide-co-PEG-acrylate) polymer using thermal free-radical polymerization and conjugated iodobenzoyl chloride to hydroxyl end groups to enable radiopacity. They found that increasing the molar concentration of iodobenzoyl chloride (0%, 3% or 15%) reduced the LCST (32° C., 18° C., 5° C., respectively) but also enhanced the relative radiopacity. Overall, this study illustrated the potential of creating a radiopaque RTG material, but further investigation is needed to optimize the gel point while maintaining an appropriate concentration of radiopaque material.

Significance of the Research Study:

The need for safer, better performing and more reliable embolic materials for the treatment of type II endoleaks and other vascular conditions is evident from the literature. Reports of complications associated with Onyx such as systemic toxicity, vascular necrosis and acute respiratory distress syndrome are serious and warrant investigation of more biocompatible materials [2], [28], [29]. From a practical standpoint, Onyx and other experimental embolics require substantial preparation or mixing time prior to use, which can delay procedures and require patients to remain under anesthesia for longer than necessary. Furthermore, delivery of embolic materials through microcatheters to sites with complex, tortuous vasculature is challenging. Embolic agents that are relatively large in size or those that are prone to solidification prior to deployment are not appropriate for these applications. RTGs, however, have the potential to overcome these limitations. They are highly tunable, water-compatible polymers that can be designed with specific functionality, enabling the conjugation of biomolecules or radiopaque compounds. The thermal gelation process of RTGs makes them attractive alternatives to conventional embolic materials from a clinical standpoint because they can be delivered in liquid form using standard catheterization techniques and can be designed to form a semi-solid gel only upon reaching body temperature. In this example, principles of bioengineering are utilized to characterize, model and optimize certain embodiments of the RTGs described herein for the treatment of abdominal aorta type II endoleaks. This study evaluates that a PEGSA-PNIPAm RTG, in an embodiment, dispersed in water at 15% (w/v) can be delivered through a 3 French microcatheter (0.67 mm ID, 150 cm length), transitions to a gel between 32-37° C. and is non-cytotoxic.

Consideration of FDA Guidelines and RTG Applications in the Study Design:

With the a goal of bringing a new embolic material to market, it is important design a study to take into consideration not only the most appropriate applications for an RTG, but also the pertinent FDA biocompatibility guidelines for new materials. According to the FDA and International Standards Organization (ISO), for permanent blood contacting devices, comprehensive testing should be performed, including cytotoxicity, sensitization, hemocompatibility, pyrogenicity, implantation, genotoxicity, carcinogenicity, reproductive and developmental toxicity, and degradation assessments [53]. These endpoints should be addressed in upcoming studies, with existing data, or if the testing is not required, with an explanation of the rationale for why the test is not needed. In the case of this RTG, it will be desirable to target a 510 k application for peripheral vascular occlusion if it can be deemed substantially equivalent to an existing product (e.g. coils or Onyx).

Satisfying all of these biocompatibility endpoints is beyond the scope of this particular example; however, these FDA and ISO recommendations have guided the design for polymer characterization, cytotoxicity and degradation tests described in the upcoming sections. Furthermore, focusing on peripheral vascular occlusion applications helps to narrow the example scope and facilitate the optimization process of an RTG.

Materials and Methods:
Synthesis of PEGSA-PNIPAm:
Materials and Equipment:

Poly(ethylene glycol) diglycidyl ether (PEGDGE), succinic acid (SA), triphenylphosphine (TPP), N-isopropylacrylamide (NIPAm), 4,4'-Azobis(4-cyanovaleric acid) (ACVA), N,N'-Dicyclohexylcarbodiimide (DCC), 4-(Dimethylamino)pyridine (DMAP), tetrahydrofuran (THF, anhydrous), dimethylformamide (DMF, anhydrous), and dichloromethane (DCM, anhydrous) were purchased from Sigma-Aldrich. Anhydrous diethyl ether and mineral oil were purchased from Fisher Scientific. All materials were used as received.

The following glassware was used: Round-bottom flasks (100, 250, 500 ml), Erlenmeyer flasks (500 ml), crystalizing dish (500 ml), separatory funnel (50 ml), and beakers (50, 100, 250, 1000 ml).

The following equipment was used: Digital stirring hotplate (Corning), nitrogen (high purity), rotary evaporator (Heidolph), lyophilizer (Labconco), dialysis membrane (12-14 kDa MWCO), conical centrifuge tubes (15, 50 ml, Fisher Scientific), septum stoppers, stir bars, Pasteur pipettes and micropipettes (VWR).

Figure 5:
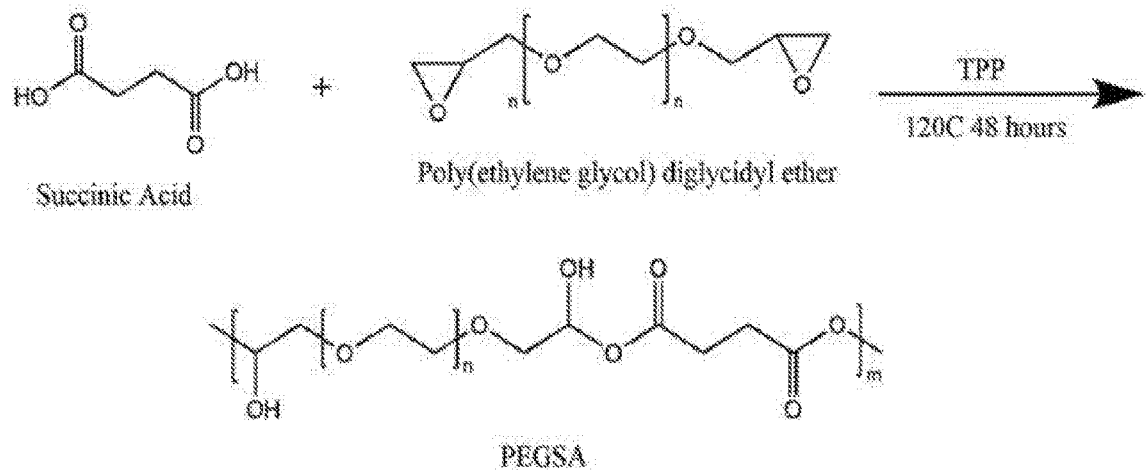
FIG. 5. Synthesis of PEGSA, PNIPAm and conjugation of PEGSA to PNIPAm.
Figure 5:
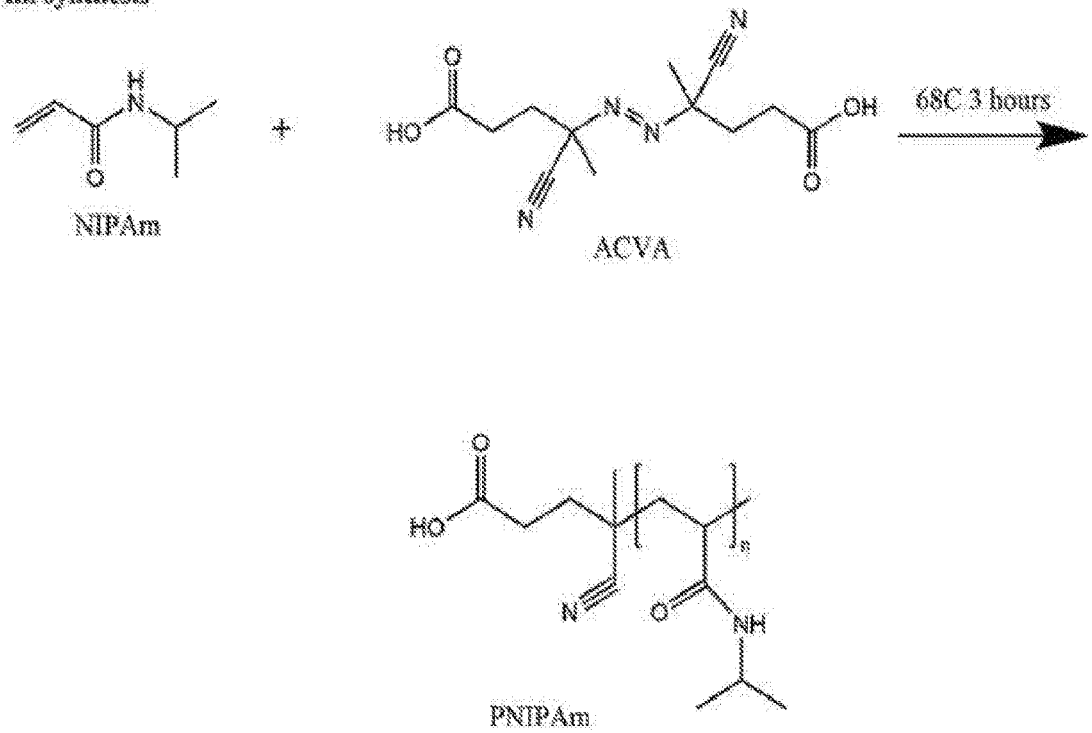
Figure 5:
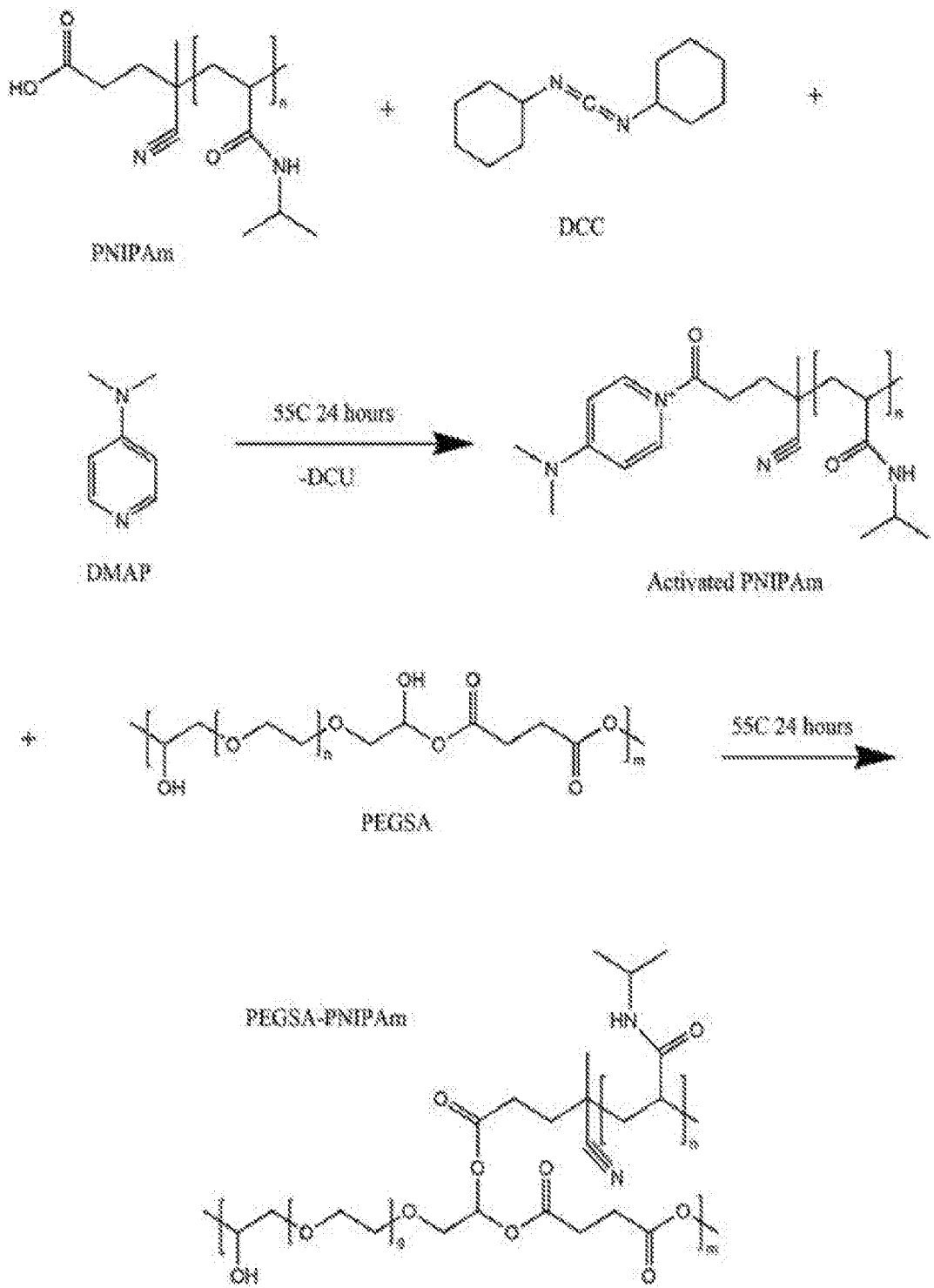
Figure 6:
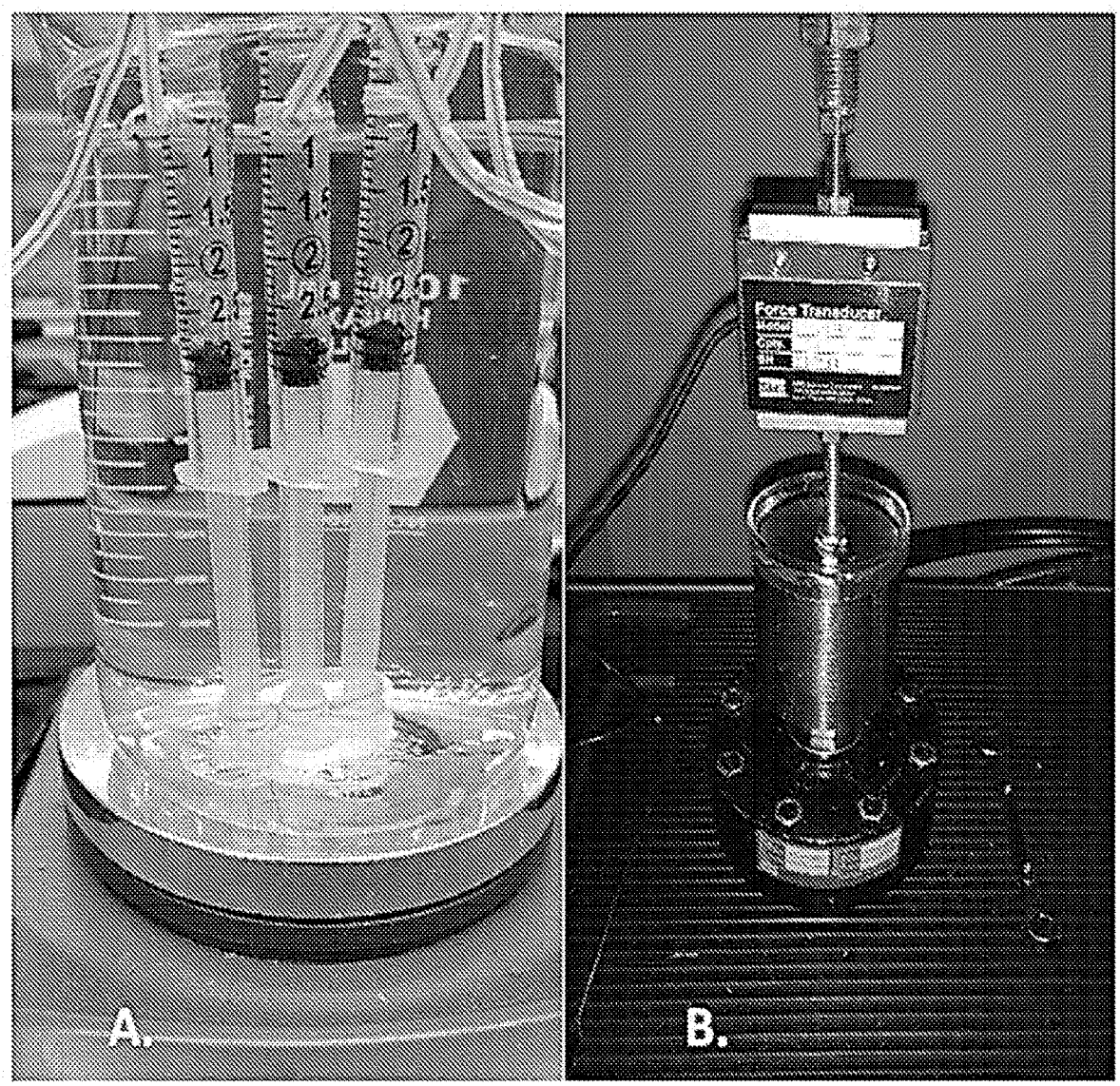
FIG. 6. A. Formation of gel cylinders using syringes. B. Mechanical testing setup for compressive modulus measurements.
Figure 7:
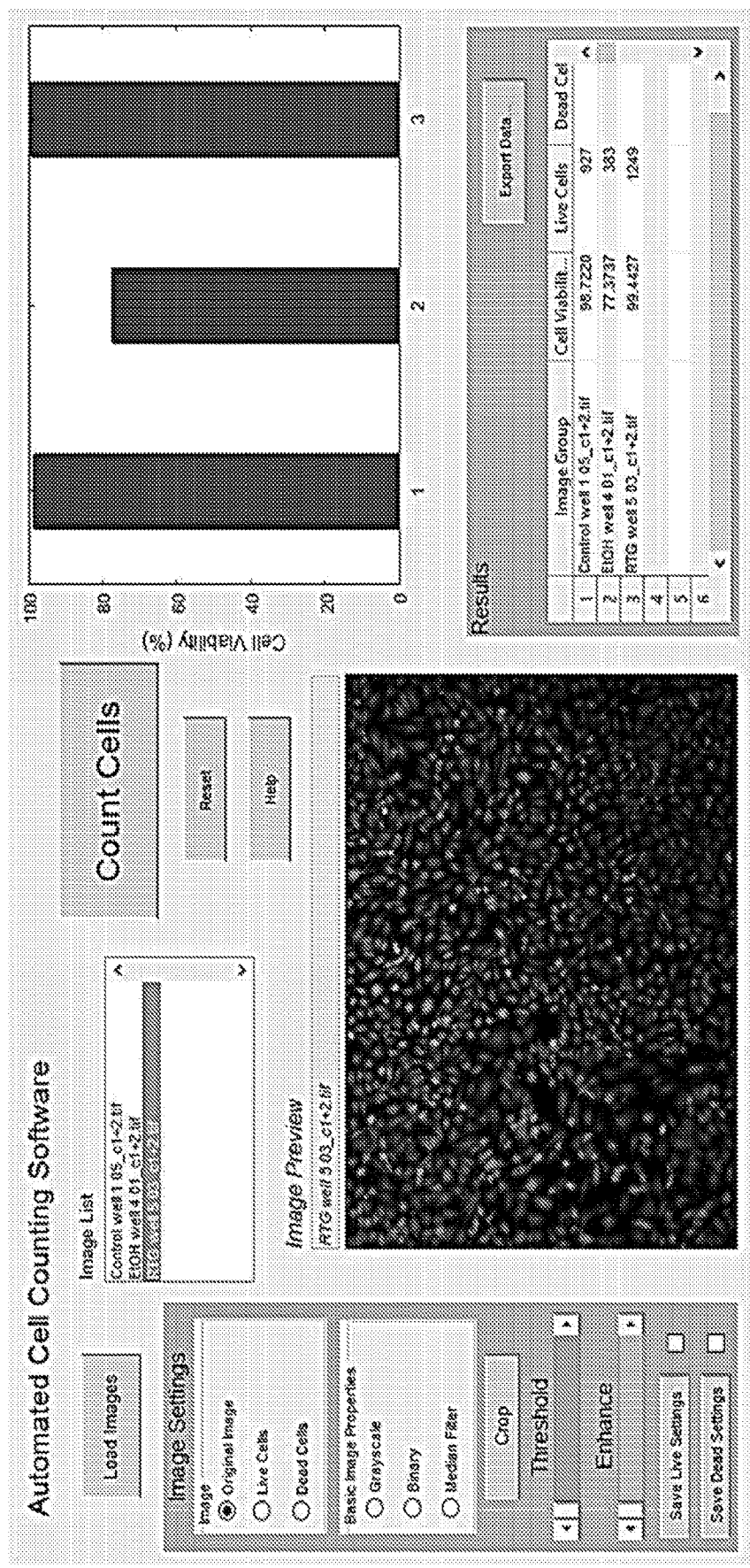
FIG. 7. Graphical user interface created using Matlab for analysis of fluorescence microscope live/dead images.

Synthesis Protocol:

Detailed synthesis steps are included in Example 2. FIG. 5 shows the structure and synthesis mechanism of an example PEGSA-PNIPAm, an embodiment of the reverse thermal gels described herein. Briefly, PEGSA is synthesized via anionic ring-opening polymerization of PEGDGE and SA using TPP as a catalyst [54]. Next, thermal free-radical polymerization is used to synthesize PNIPAm from NIPAm and ACVA. The terminal carboxylic acid from ACVA allows for conjugation with PEGSA. PNIPAm is conjugated to PEGSA using DCC and DMAP at a 4:1 ratio of PEGSA hydroxyls to PNIPAm (25% conjugation).

Preparation of RTG Solutions:

Dry PEGSA-PNIPAm polymer was dispersed in either milli-Q water or PBS at 15% (w/v). Typically, PEGSA-PNIPAm was isolated and dried in 50 ml conical centrifuge tubes. The dry weight of the polymer was obtained by subtracting the weight of the conical tube plus dry polymer from the initial empty weight of the conical tube. The resultant polymer weight was then divided by 15% to obtain the total solution volume. Subtracting the dry polymer weight from the total solution volume results in the total volume of water/PBS required to obtain a 15% (w/v) solution. Water or PBS was added directly to the conical tube containing the dry polymer using a 1000 µl micropipette. The tube was then refrigerated and shaken intermittently using a vortex mixer until the polymer was fully dissolved. Depending on the volume, concentration and frequency of mixing, the polymer required anywhere from 30 min to 12 hr to fully disperse.

In this example of an embodiment of the reverse thermal gels described herein, "PEGSA-PNIPAm" will be used to indicate the bulk dry polymer, and "RTG" will be used to designate the aqueous polymer formulation (e.g., 15% w/v) unless otherwise noted.

Sterilization of the RTG was required for cell culture studies. To perform the sterilization, PEGSA-PNIPAm was dissolved in water until a low viscosity was achieved. If the solution was too viscous, filtration became difficult. In the biosafety hood, a vacuum filtration setup with a 0.2 µm pore size connected to an autoclaved glass jar was used to filter the entirety of the solution. The solution was then transferred to sterile 50 ml conical tubes, frozen and lyophilized. After lyophilization, the material was dispersed in PBS at a 15% (w/v) concentration.

Characterization Techniques:
Material Characterization:

RTG Solution Viscosity—RTG viscosity was measured using a cone-and-plate digital viscometer (CAP2000+; Brookfield) at 20° C., 25 s runtime. Dry RTG polymer was dispersed in water at either 5, 10 or 15% (w/v) and each concentration was measured in triplicate. The effect of shear-rate dependence on the 15% (w/v) concentration was examined by varying the viscometer RPM 100-1000 RPM.

Gel Transition Temperature of RTG Solutions—Differential scanning calorimetry (DSC; Perkin Elmer) was used to measure the lower critical solution temperature (LCST) of the RTG (15% w/v in water). Approximately 20 mg of solution was added to DSC pans and tested in triplicate from 10 to 60° C. at a ramp rate of 10° C./min. The transition temperature was defined as the temperature where the peak maximum occurred on the plot of heat flow versus temperature [55].

Infrared Spectroscopy—Polymer samples were analyzed using Fourier transform infrared spectroscopy (FTIR; Nicolet 6700) in the region from 4000-400 $cm^{-1}$, using an optical velocity of 3.79, aperture of 10, with 32 averaged scans at a resolution of 4 $cm^{-1}$. Samples measurements were performed by placing a trace amount of solution on KBr salt plates. Dry polymer samples were dispersed in THF prior to being placed on the salt plates.

NMR—Polymer samples were further analyzed using proton nuclear magnetic resonance (NMR; Bruker Avance 500). To obtain the spectra, approximately 25 mg of material was dissolved in deuterated chloroform.

Molecular Weight Characterization—Triple detection gel permeation chromatography was used to obtain molecular weight measurements of PEGSA and PNIPAm (GPC; refractive index, viscometer, light scattering; Viscotek). Samples were prepared in THF at six concentrations ranging from 2.5-5 mg/ml. The GPC system was calibrated with a 65 kDa poly(methyl methacrylate) standard.

Static light scattering was used to determine the molecular weight of PEGSA-PNIPAm (Zetasizer Nano ZS90; Malvern). Polymer samples were dissolved in THF at concentrations of 0.5, 0.75, 1.0, 1.5, 2.0 and 2.5 mg/ml.

RTG Compressive Modulus—A mechanical testing system equipped with a 10 N load cell was used to measure the compressive modulus of the RTG at 37° C. (858 Mini Bionix; MTS Systems). A cylinder of gel was formed using a 3 ml syringe with a cut off tip. Approximately 0.5 ml of solution was loaded into the syringe. The syringe was then placed into a water bath at 37° C. After 1 min the gel cylinder was extruded from the syringe and transferred to a glass dish filled with 37° C. water. The dish was placed on a platen fixture on the mechanical testing system and the gel was compressed at a rate of 1 ml/min for a distance of 5 mm or until the material fractured. Load-extension data were collected and compressive modulus was calculated.

RTG Volume Shrinkage—In vitro volumetric shrinkage of the RTG was determined by measuring an approximately 10 mm cylindrical segment of RTG immediately after catheter delivery using precision calipers. The RTG was injected through a 6 Fr catheter into a glass petri dish containing water at 37° C. A spatula was used to cut the gel into roughly 10 mm segments. Measurements of the length and diameter of each segment were taken immediately upon injection and after 1, 3, 5, 10, 30 and 60 min, as well as after 6 and 24 hours. All measurements were conducted in triplicate. Percent volumetric shrinkage calculated and plotted as a function of time.

Cytotoxicity:

Human umbilical vein endothelial cells (HUVECs, passage 5, Lonza) were used to assess cytotoxicity of the RTG. Approximately 1 mL of gel was formed and added to 5 mL of HUVEC media (EBM-2 BulletKit, Lonza) and incubated for 24 hours. The extract media was added to plated HUVECs and incubated for an additional 24 hours. Full EBM-2 media and EBM-2 media plus 10% ethanol were used as controls. A live/dead assay was run (calcein/ ethidium homodimer, ThermoFisher) and cells were imaged using a fluorescent microscope (Zeiss; n=2 wells/treatment, 5 imaged regions per well). A detailed protocol is included as Example 4.

Quantification of Cell Viability Using Matlab:

Image analysis and cell counts were conducted using Matlab. A graphical user interface was created which allowed the user to import the image files, perform preprocessing steps to optimize the images, select a single cell region of interest, automatically determine the cell counts based on the single cell area and visualize the results graphically and numerically. Image processing included color channel isolation, top-hat filtering to correct for non-uniform illumination, image thresholding to remove non-cellular artifacts, and edge smoothing. The amount of processing steps required was dependent on image quality and cell clarity and was performed on a case-by-case basis. The percent cell viability was calculated for each image and Microsoft Excel was used to calculate the average and standard deviation for each group of images.

Hydrolytic and Oxidative Degradation:

Long-term stability of the RTG was evaluated using an accelerated hydrolytic and oxidative degradation test method. Briefly, 1 mL samples of 15% (w/v) RTG in milli-Q water were added to glass scintillation vials. The vials were heated in a 37° C. incubator to induce gelation. 10 mL of either 20% hydrogen peroxide in 0.1M cobalt chloride solution ($H_2O_2/CoCl_2$) or milli-Q water was then added to the vials. The mixtures were heated and agitated in a shaking incubator (37° C., 60 RPM, VWR Scientific Products) and removed after either 3, 6, 12, 18 or 24 days. Upon removal, the samples were washed, lyophilized, weighed and compared to the original polymer weights. FTIR, NMR and live/dead assays were conducted on the samples and extracts to assess for evidence of chemical changes and cytotoxicity. All samples for each time point were run in triplicate. The complete protocol is described in detail in Example 3.

Figure 8:
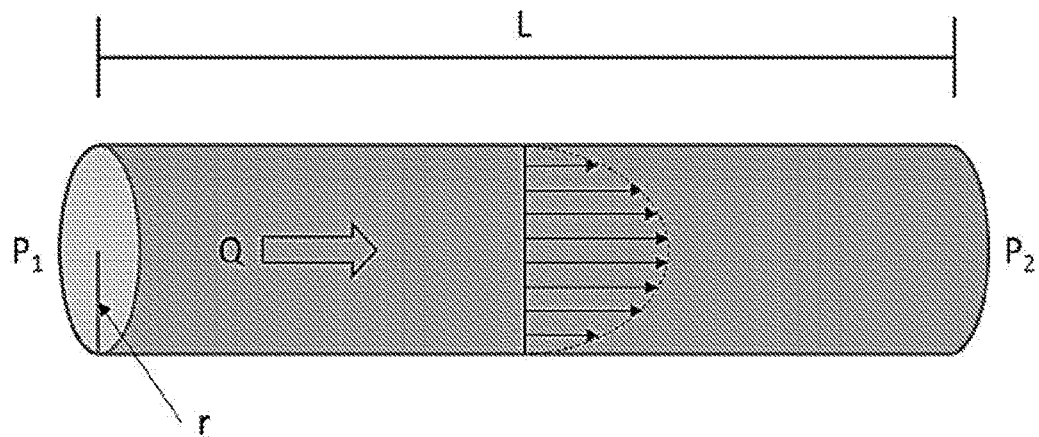
FIG. 8. Poiseuille's Law describing the pressure drop for fluid flow in a pipe.

Preliminary Modeling:

Catheter Pressure Drop:

To estimate the feasibility of delivering the RTG solution through a microcatheter, Poiseuille's Law (FIG. 8, Equation 3) was used to calculate the change in pressure across a given length of catheter L, with radius r, RTG flow rate Q and RTG viscosity p. Poiseuille's Law states that the pressure drop of a fluid flowing in a rigid pipe is directly proportional to the overall fluid resistance and the steady state fluid flow rate (Equation 1). The overall fluid resistance incorporates the viscous resistance and the combined geometric resistance. From Equation 2, it is shown that the overall fluid resistance is proportional to both the viscosity, p, and the pipe length, L, and inversely proportional to the pipe radius raised to the fourth power.

$$\Delta P = QR \quad (1)$$

$$R = \frac{8\mu L}{\pi r^4} \quad (2)$$

$$P_2 - P_1 = \frac{8\mu L Q}{\pi r^4} \quad (3)$$

Using the pressure drop results, the force required to inject the RTG through a syringe attached to the catheter can be estimated. If the outlet pressure, $P_2$, at the distal tip of the catheter is known (e.g. atmospheric pressure, average venous or arterial pressure) then the pressure, $P_1$, at the proximal end of the catheter can be determined from Equation 3. Given the syringe cross-sectional area, the force required to overcome this pressure and induce flow can be determined.

Figure 9:
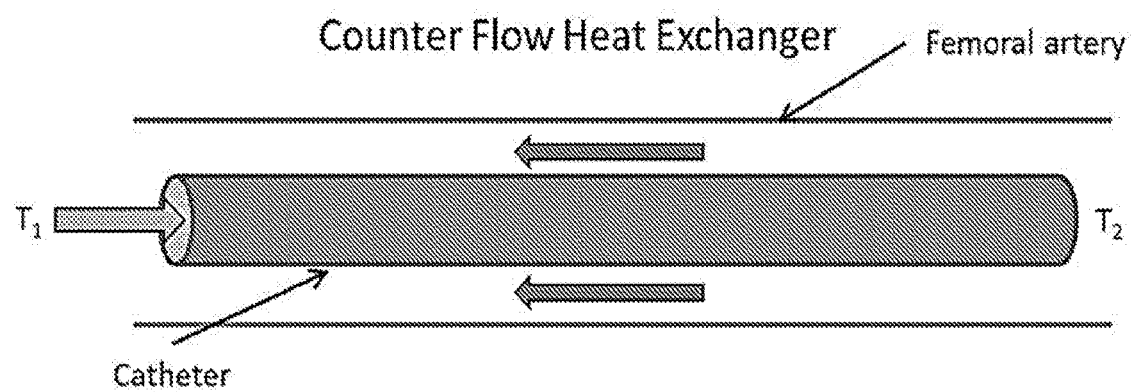
FIG. 9. Heat exchanger diagrams for determining RTG gelation time inside a catheter.
Figure 9:
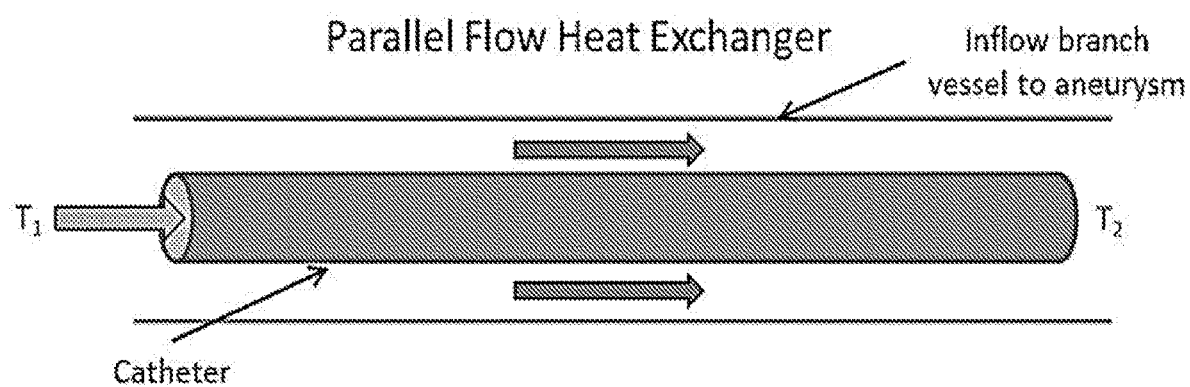
Figure 10:
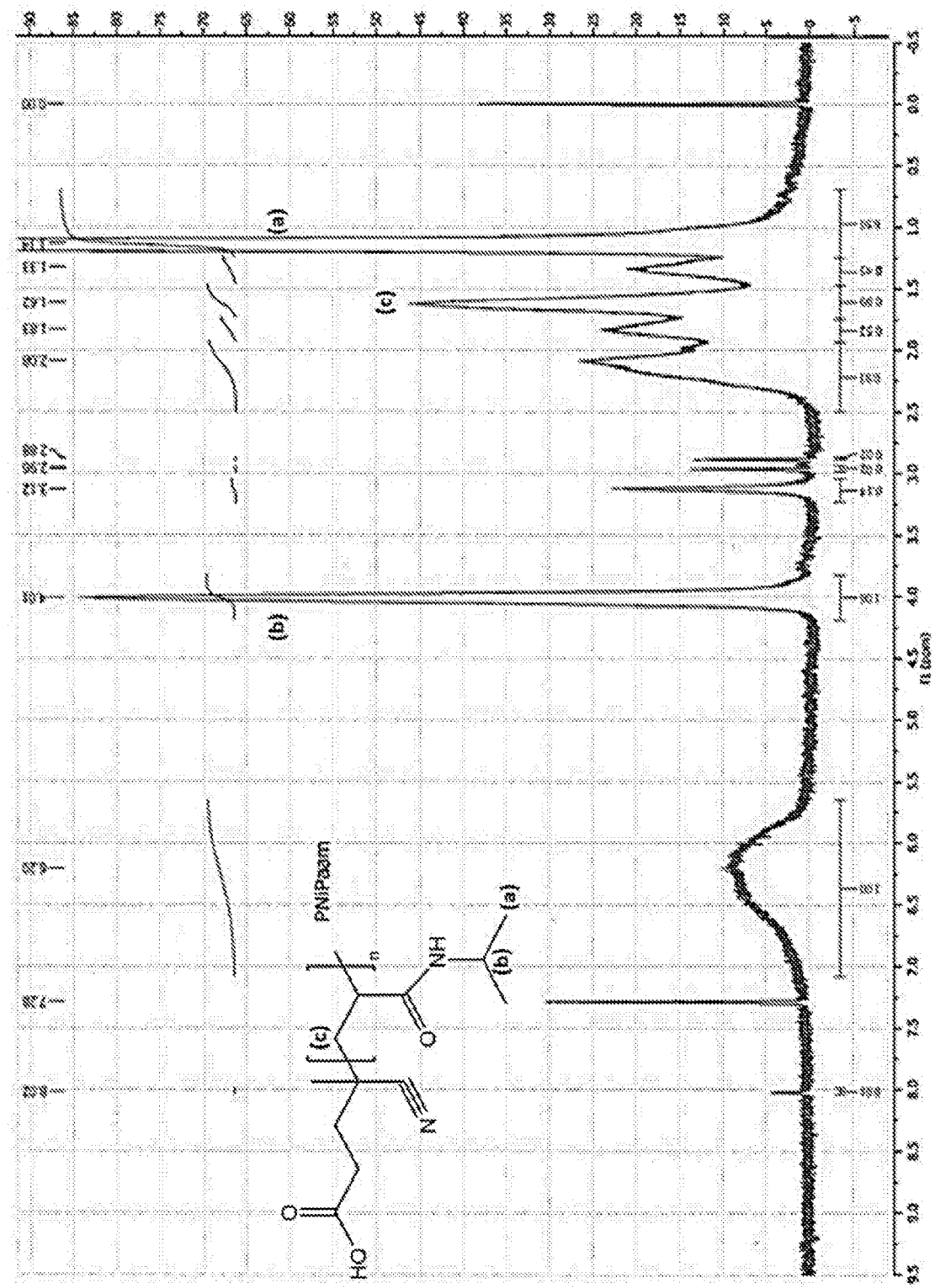
FIG. 10. NMR spectrum of PNIPAm shows the presence of methylene protons (a) and (b) at 1.14 and 4.01 ppm, and methyl protons (c) at 1.62 ppm.
Figure 11:
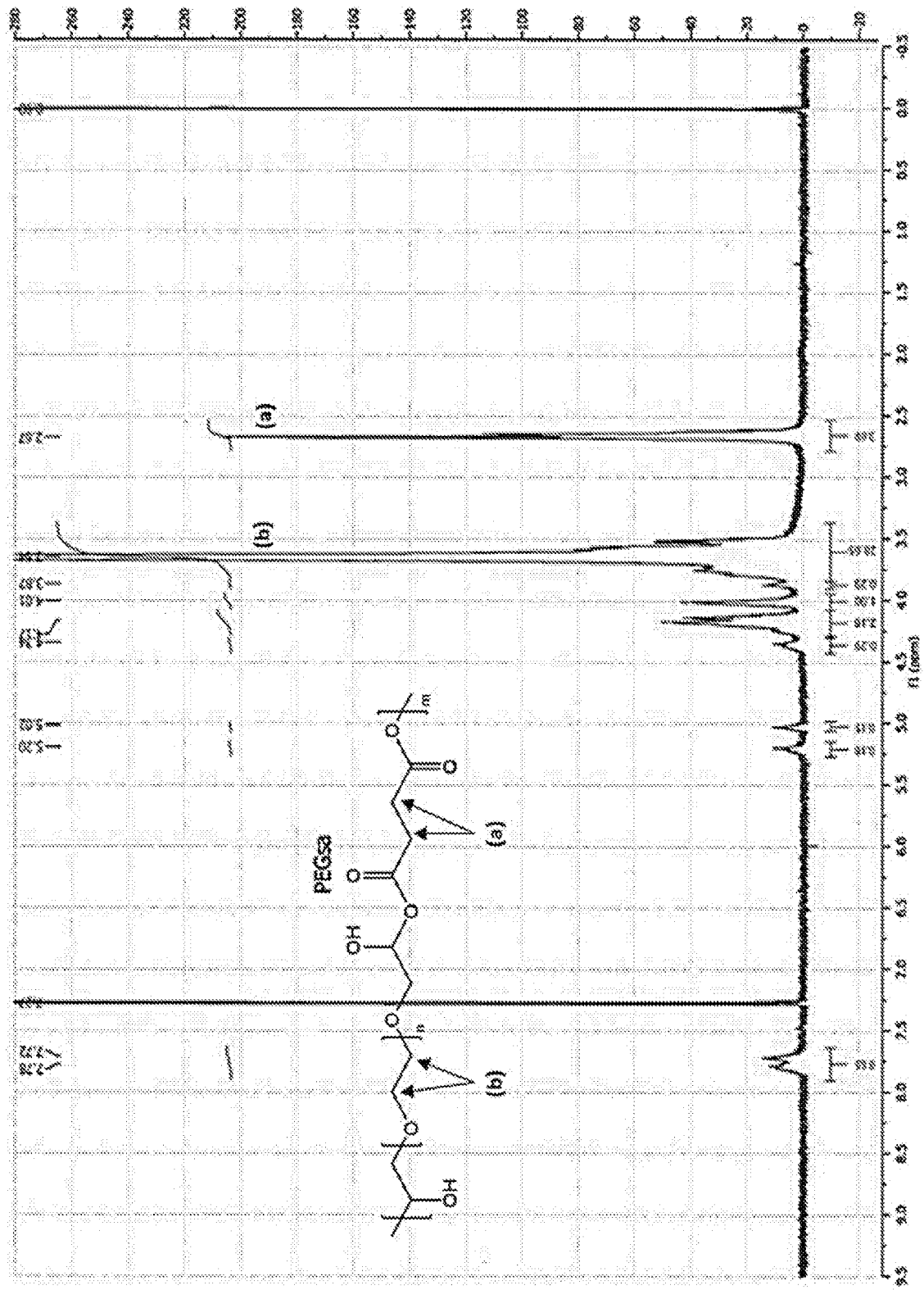
FIG. 11. NMR spectrum of PEGSA shows the presence of methylene protons from polyethylene glycol (a) at 2.67 ppm and succinic acid (b) at 3.64 ppm.
Figure 12:
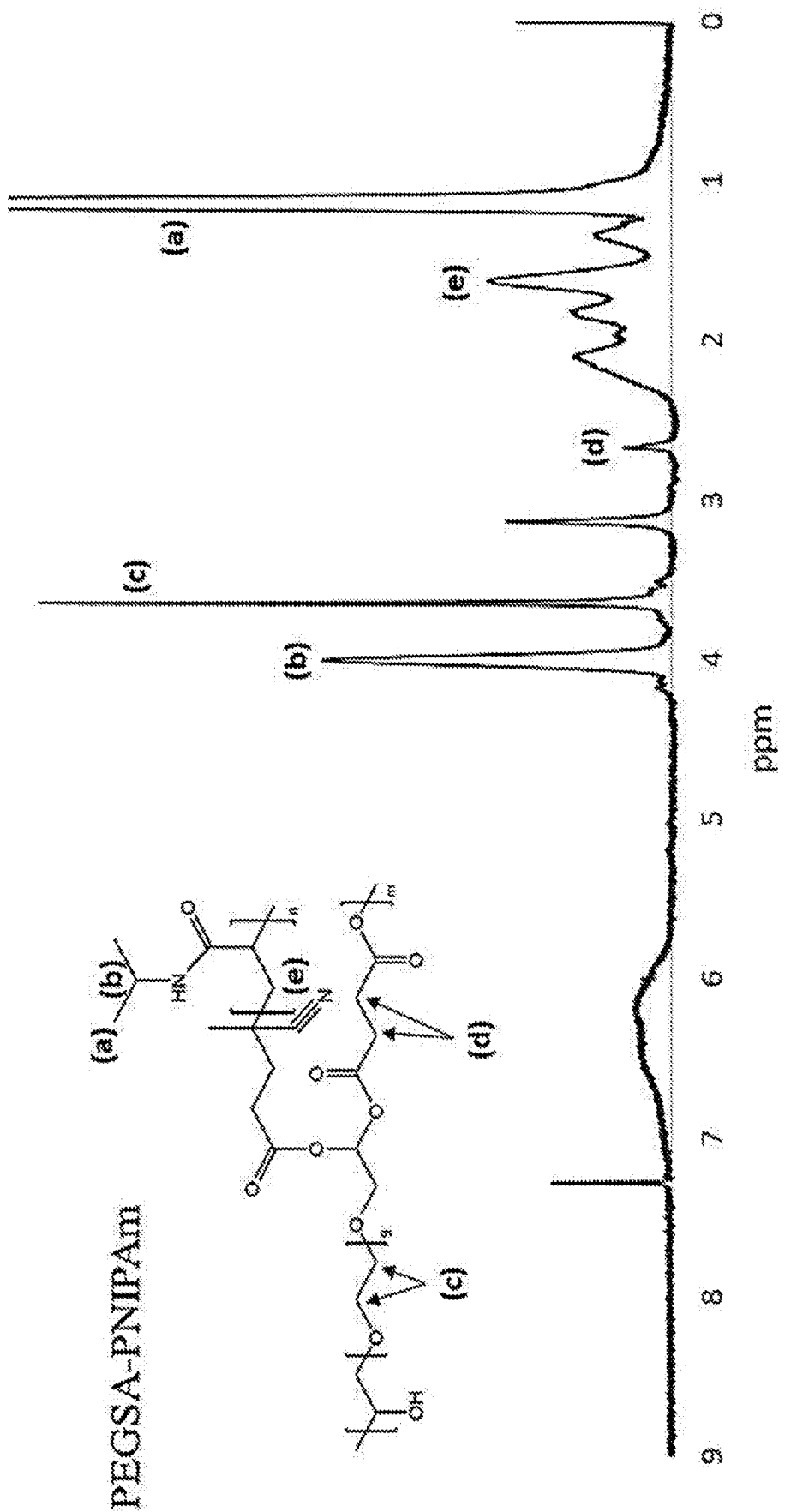
FIG. 12. NMR spectrum of PEGSA-PNIPAm. Conjugation was confirmed by the presence of methylene protons from PEGSA (c) at 3.65 ppm and (d) and 2.65 ppm, and methyl protons (a) at 1.14 ppm and methylene protons (b) at 4.01 from PNIPAm.
Figure 13:
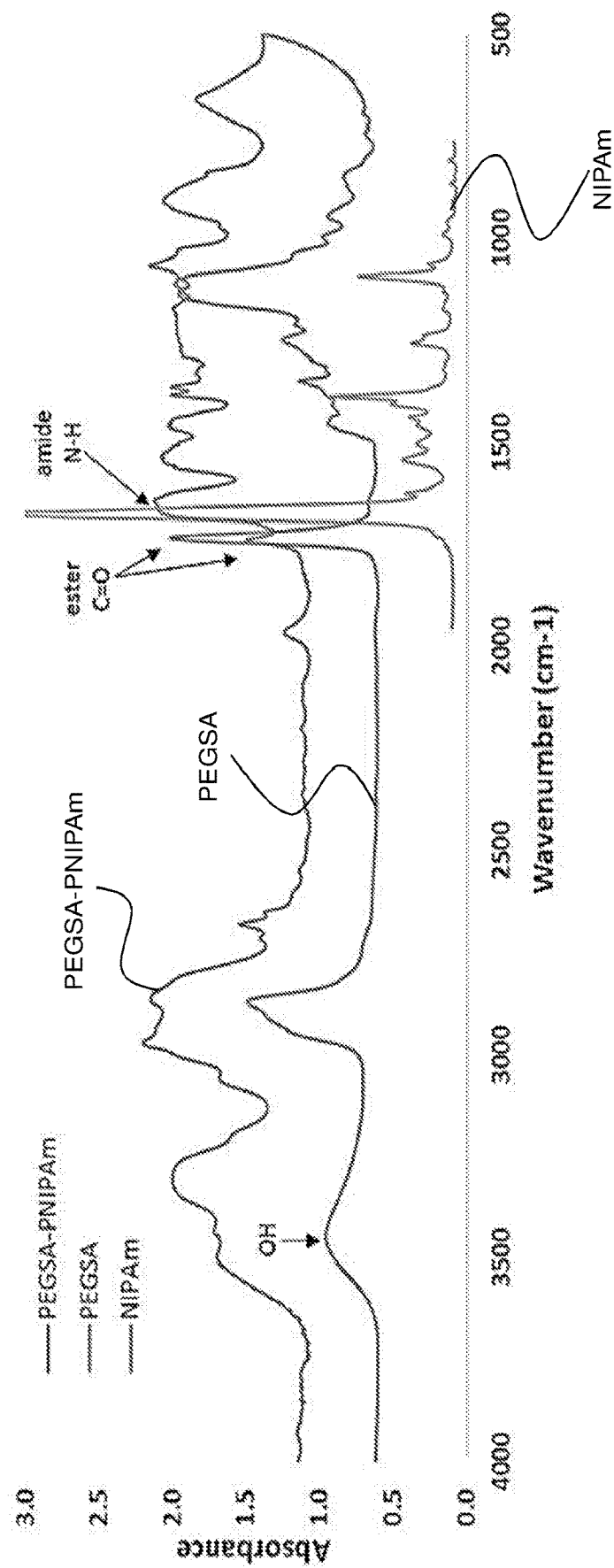
FIG. 13. FTIR spectra of PEGSA, NIPAm and PEGSA-PNIPAm. The ester carbonyl is present in PEGSA-PNIPAm, indicating successful conjugation.

Rate of Heat Transfer During Catheter Delivery:

The rate of heat transferred to the RTG during delivery in a blood vessel can be estimated by modeling the vessel-catheter system as a heat exchanger (FIG. 9). Blood flow in the vessel transfers heat across the surface of the catheter and heats the RTG. The blood flowrate, RTG flowrate, direction of flows and catheter material all have an effect on the temperature of the RTG as it moves through the catheter. Equation 4 can be used to determine the catheter outlet temperature as a function of catheter length, where q is the rate of heat transfer (W), U is the overall heat transfer coefficient (W/(m$^2$K)), A is the heat transfer surface area (m$^2$) and $T_{LM}$ is the log mean temperature difference (° K).

$$q = UAT_{LM} \quad (4)$$

The Number of Transfer Units (NTU) method was used in conjunction with Equation 4 to calculate the RTG outlet temperature, $T_2$ [56]. The model heat exchanger was divided into discrete lengths and the outlet temperature, $T_2$, was calculated. $T_2$ was then used as the inlet temperature, $T_1$, for the next segment and the calculations were repeated. This process was iterated over the full length of the catheter to determine the RTG temperature profile. Calculations were performed and plots were developed using Matlab.

Assumptions and Limitations of Models:

The catheter pressure drop model assumed steady-state, fully-developed laminar flow of an incompressible, Newtonian fluid. Entrance and exit effects are neglected, and a no-slip boundary condition is assumed between the interface between the inner wall of the catheter and the RTG. Poiseuille's Law is valid for straight pipes of uniform inner diameter, therefore, curvature of the catheter is neglected. The model assumes RTG flow in the catheter prior to gelation. The model is limited by the fact that the RTG solution was considered to be a Newtonian fluid. This is discussed in more detail with the viscosity results in the section on quantification of RTG solution viscosity, gel transition temperature, shrinkage and compressive modulus. If non-Newtonian flows were to be considered, the viscosity parameter would be modified based on the power-law model [57], [58].

The heat transfer model assumes the outer surface of the vessel is perfectly insulated and that heat transfer occurs only between the blood and the RTG solution; the mass flow rates, specific heats of the fluids and overall heat transfer coefficient, U, remain constant; and the temperatures of each fluid over a specific cross-sectional area is constant. This model is limited because it is describing steady-state heat transfer from a hot fluid to a cold fluid. In reality, the vessels are not perfectly insulated from the rest of the body, and the pulsatile nature of blood flow likely results in varying mass flow rates and thus non-uniform heat transfer across the catheter. Furthermore, the overall heat transfer coefficient can only be approximated due to the experimental nature of the RTG and proprietary catheter materials.

Optimization and In Vitro Testing:

Benchtop testing was conducted to assess in vitro performance of the RTG. Four factors were considered: (1) Overall injection of the RTG through catheters with an emphasis on microcatheter delivery, (2) delivery through simulated tortuous vasculature at body temperature, (3) space-filling/blocking capabilities of the RTG and (4) simulated delivery into model vessels under physiological pressures. A 15% (w/v) mixture of RTG in phosphate buffered saline (PBS) was prepared and added to a 1 mL disposable syringe. The syringe was connected to either an 8, 6, 5 or 1.9 French catheter (Cordis, Microlumen, Cook, and ev3 Echelon 14 catheters, respectively. Note: the French (F) catheter scale is a measurement of the outer diameter of the catheter. 1 F=0.333 mm=0.013 in.). At a minimum, the distal 30 cm of the catheter was placed in a 37° C. water bath and the RTG solution was extruded through the catheter into the water bath either by hand or using a syringe pump (1 mL/min flow rate, New Era Pump Systems Inc).

Data Analysis:

For all physical property tests (light scattering, viscosity, gel temperature, shrinkage and modulus) the data for each material was reported as the average of three runs and the error was reported as standard deviation. For comparative tests (cytotoxicity, degradation), a one-way Anova was used where $p<0.05$ was considered statistically significant. If statistically significant differences were found, a two-sample t-test was used to determine differences in means between the groups. $P<0.05$ was considered statistically significant.

Results:

RTG Characterization:

Bulk Polymer Structural Characterization Using FTIR, GPC, NMR and Static Light Scattering:

NMR and FTIR spectra of PEGSA, PNIPAm, and PEGSA-PNIPAm (FIGS. 10-13) were used to confirm the successful synthesis of PEGSA and the conjugation of PNIPAm to the available PEGSA hydroxyls.

GPC was used to determine the molecular weights of PEGSA and PNIPAm. For this example embodiment, PEGSA had an average molecular weight (MW) of 6.2 kDa and PNIPAm had a MW of 91 kDa. Since this PNPAm MW is substantially higher than the MW of 10 kDa used in the synthesis calculations (Example 2), it is estimated that the actual conjugation ratio is closer to one PNIPAm molecule per every 36 hydroxyl groups.

For this example embodiment, due to the highly branched nature of PEGSA-PNIPAm, it was difficult to achieve clear column separation on the GPC and as a result, the MW of PEGSA-PNIPAm was not successfully determined using this method. However, static light scattering has been used as technique for polymer MW determination [59], [60]. This technique is derived from the Rayleigh theory that using a given light source and wavelength, large molecules scatter more light than small molecules. The Rayleigh equation (Equation 5) calculates the MW of a polymer based on its concentration in a solvent of known refractive index. In Equation 5, $M_w$ is the molecular weight of the polymer, c is the sample concentration, K is the Debye constant based on the solvent refractive index and the refractive index increment of the polymer, and $\Delta R$ and $A_2$ are coefficients based on the scattering angle. Since PNIPAm is the primary weight fraction of the total polymer, in this example embodiment, the refractive index increment was assumed to be 0.107, based on literature values for PNIPAm [61].

$$\lim_{\theta \to 0} \frac{Kc}{\Delta R_\theta} = \frac{1}{M_w} + 2A_2 c \quad (5)$$

The results of the light scattering measurements indicated an average PEGSA-PNIPAm MW of 273±21 kDa, for this example embodiment.

Figure 14:
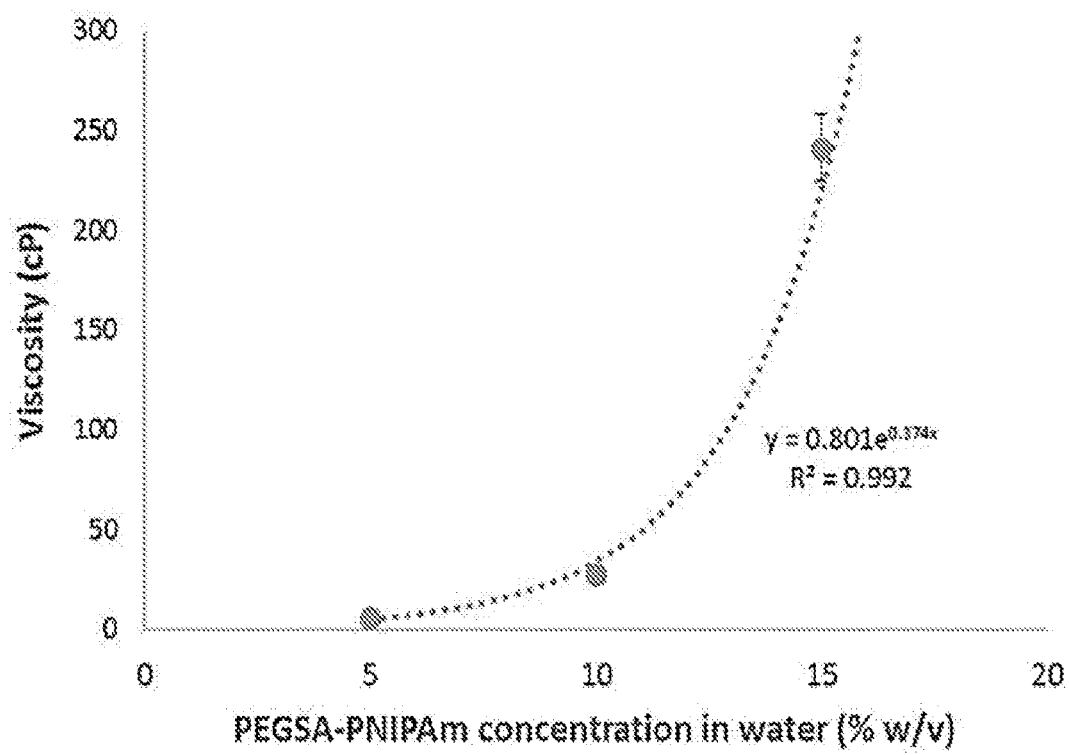
FIG. 14. RTG solution viscosity from 5-15% (w/v) showed an exponential increase in viscosity with increasing polymer concentration. Data represents three measurements at each concentration.

Quantification of RTG Solution Viscosity, Gel Transition Temperature, Shrinkage and Compressive Modulus:

For this example embodiment, the RTG solution viscosity is shown in FIG. 14. The data shows an exponential increase in viscosity with PEGSA-PNIPAm loading. This behavior is consistent with that seen in other systems containing linear or branched polymer solutions [62]. At the 15% concentration, the average viscosity was approximately 241.4±16.7 cP, whereas at the 10% concentration, the average viscosity was 27.7±2.1 cP. These results emphasize the importance of optimizing the polymer concentration when designing the material for microcatheter delivery applications.

For this example embodiment, the shear rate dependence of the RTG at the 15% concentration was examined by varying the shear rate on the viscometer from 133 to 13333 $s^{-1}$. No significant change in viscosity was observed at the different shear rates. This suggests that at concentrations at or below 15% (w/v), the material can be assumed to behave as a Newtonian fluid. However, it is expected that as both the concentration and the viscosity increase, a shear-rate dependence would become evident due to the increased interparticle polymer interactions [63].

Figure 15:
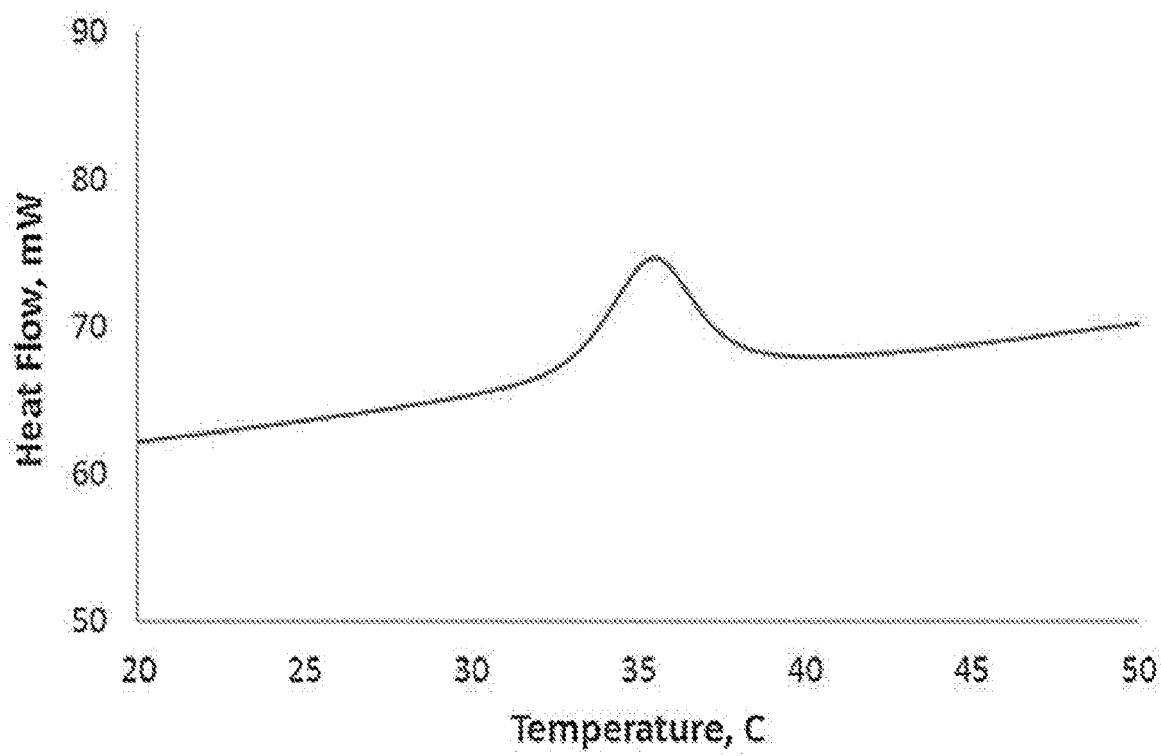
FIG. 15. A representative plot of heat flow versus temperature obtained by DSC. The peak at approximately 35° C. indicates the LCST.

The DSC results in FIG. 15 showed an average LCST of 34.6±0.6° C. for the RTG at the 15% (w/v) concentration, in this example embodiment.

Figure 16:
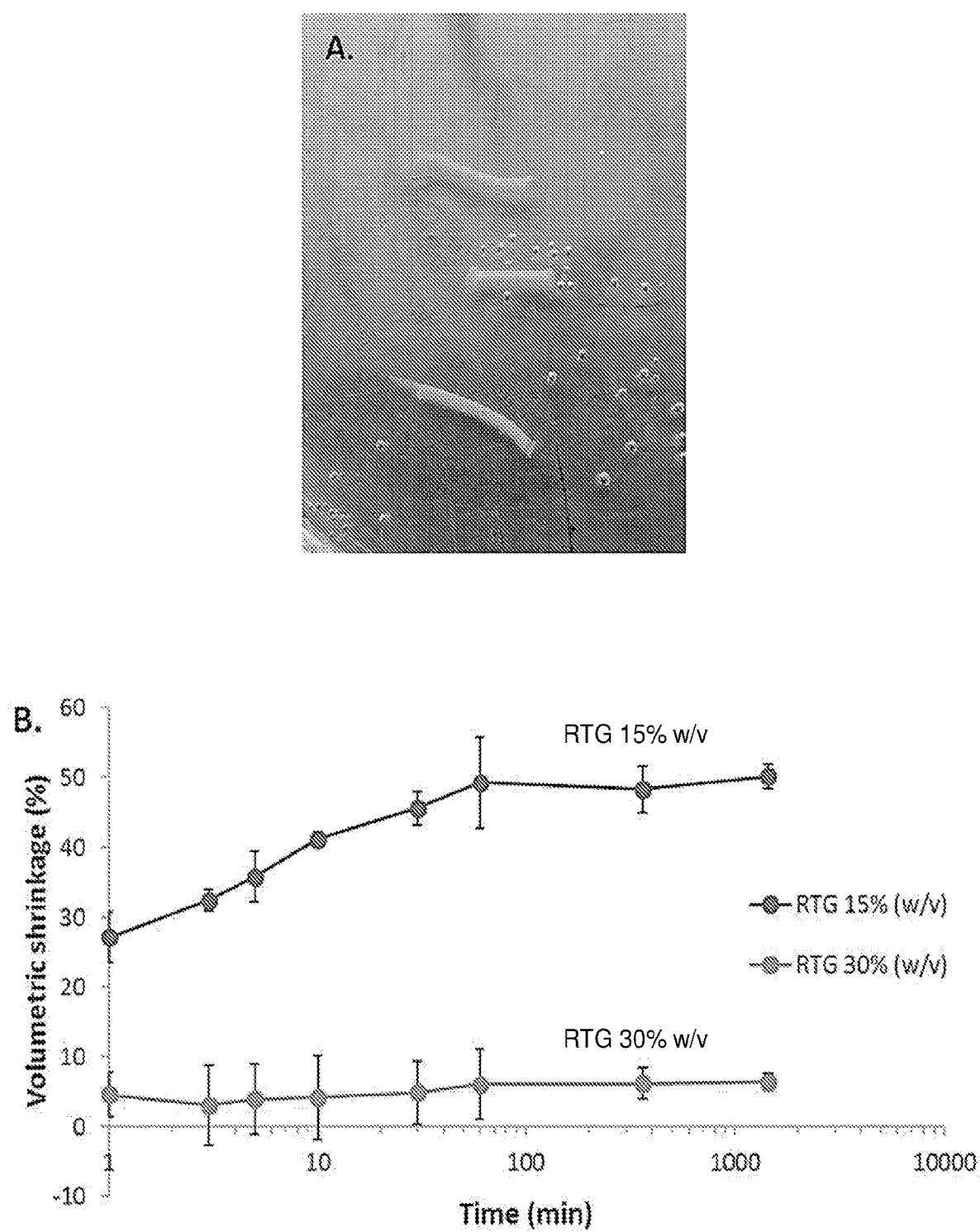
FIG. 16. Quantification of RTG shrinkage. A. 10-15 mm segments of RTG were extruded from a 6 F catheter into a 37° C. water bath. The length and diameter was measured using precision calipers. B. Plot of percent volumetric shrinkage versus time for RTG composed of either 15% or 30% PEGSA-PNIPAm. Measurements were taken at 1, 3, 5, 10, 30, 60 minutes, and at 6 and 24 hours. Data represents the average of three measurements at each concentration and the x-axis is shown on a log scale.

Quantifying the volumetric shrinkage of the RTG is an important aspect of characterizing the material and can provide insight into how much material must be delivered during an embolization procedure to avoid recanalization or migration of the material. However, quantifying the volume change directly in real-time is challenging because removing the gelled RTG from the 37° C. environment results in reconstitution to the solid state. As a result, dimensional measurements had to be taken with the gel samples in a glass dish containing water at 37° C. FIG. 16 A. shows an image of the 10-15 mm cylindrical RTG samples after extrusion from a 6 F catheter.

The plot in FIG. 16 B. shows the calculated volume change overtime of 15% RTG and 30% RTG, in this example embodiment. The maximum volumetric shrinkage for the 15% (w/v) RTG formulation was 50.2±1.8%, while the maximum volumetric shrinkage for the 30% (w/v) formulation was 6.4±1.2%. The largest relative volume change occurred between the initial measurement and the first minute. As the initial gel forms almost instantaneously upon exposure to the water, this high volume change after the first minute is likely due to the hydrophobic groups on the PNIPAm chains causing syneresis as they continue to aggregate together and drive out water from the center of the material [52].

The shrinkage in the 15% RTG formulation reached a plateau after about one hour, whereas the 30% formulation showed no significant differences in shrinkage after the first minute. The maximum reduction in diameter of the 15% RTG formulation was approximately 22%. This is an important consideration for applications where one string of RTG extruded from a catheter is used to block or clog a small downstream vessel. For example, if the intent is to block a 2 mm diameter vessel using the 15% RTG formulation, then the diameter of the RTG would need to be at least 2.55 mm in diameter to account for the radial shrinkage.

Figure 17:
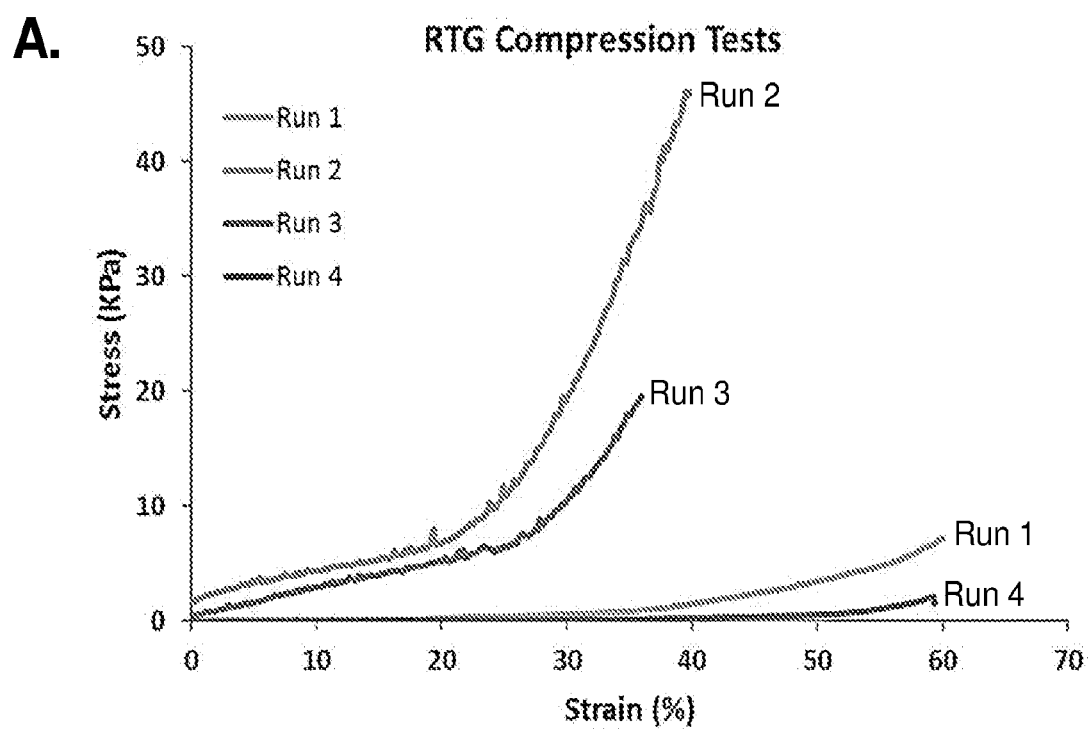
FIG. 17. A. Stress-strain data for cylindrical gelled RTG samples tested in compression. B. Cylindrical RTG test specimens prior to testing.
Figure 17:
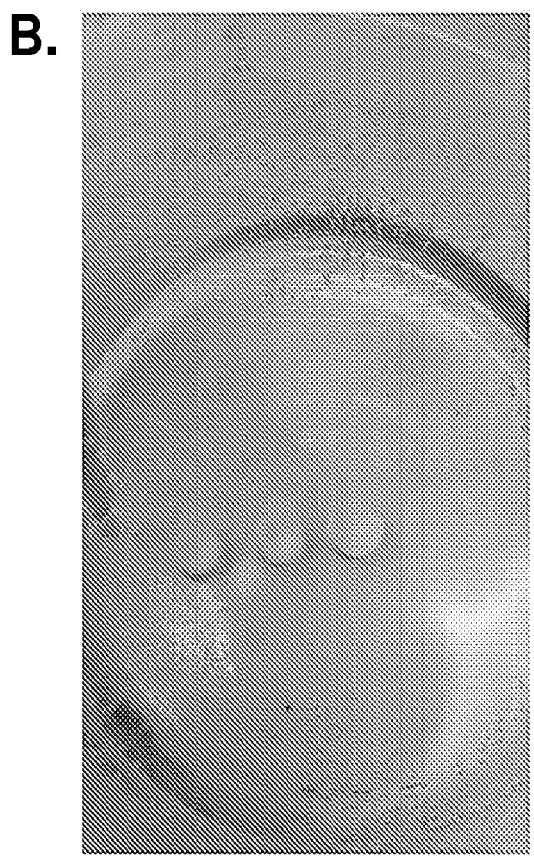

Compressive tests were performed on gelled RTG samples and the resulting stress-strain curves are plotted in FIG. 17, for this example embodiment. The calculated modulus was 0.53, 3.17, 3.33 and 0.30 MPa for runs 1-4, respectively. The high degree of variation in modulus is likely due to the samples beginning to reconstitute back into a liquid during the tests, as the water bath cooled below 37° C. To achieve more reliable data, the test setup needs to be modified in order to keep the water bath at a stable temperature during the duration of the tests. Alternatively, samples could be tested on a rheometer using a temperature sweep to probe the complex modulus of the material pre- and post-gelation.

Adjusting the Synthetic Procedure to Reduce RTG Solution Viscosity:

The prospect of delivering a 15% RTG solution through a microcatheter (with the viscosity shown in FIG. 14) will be discussed in the section on analytical model results; however, it was determined that it would have been difficult to accomplish by manual injection, in an embodiment. Consequently, adjustments were made to the PNIPAm synthetic procedure in an attempt to reduce the RTG solution viscosity, in an embodiment. Briefly, the solvent concentration for the PNIPAm synthesis was increased from 2:1 to 3:1 and the polymerization time was reduced from 4 hours to 3 hours at 70° C. The remainder of the procedure, including the synthesis and conjugation of PEGSA remained unchanged.

Figure 18:
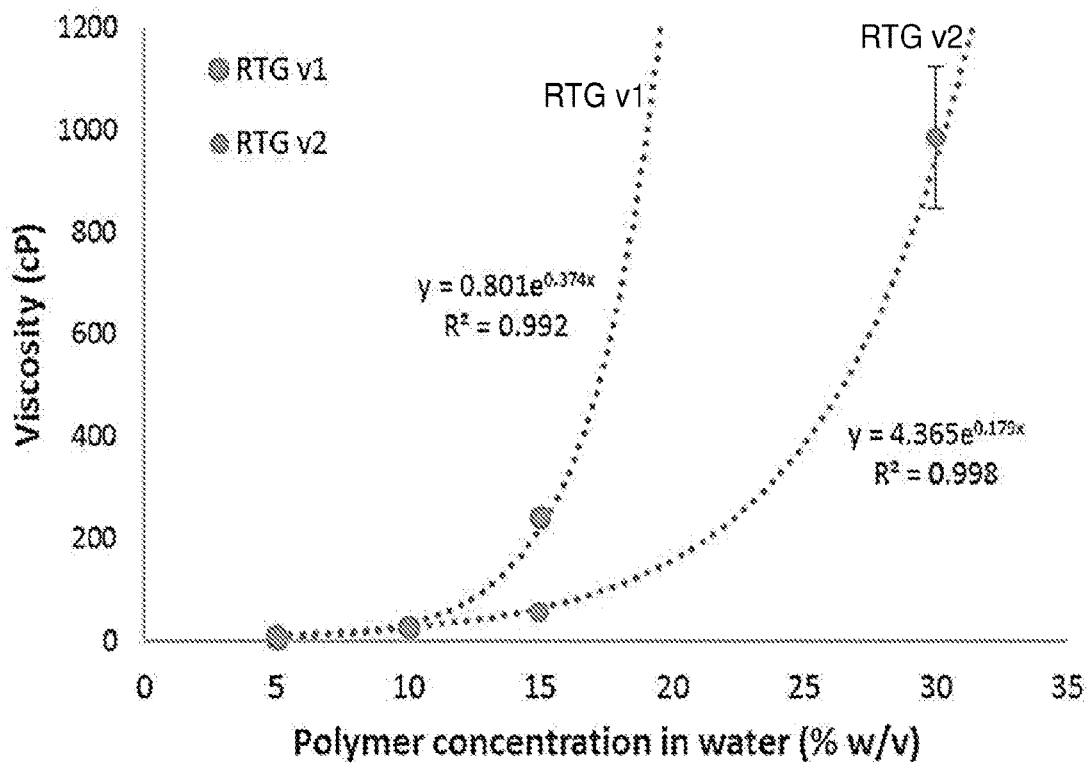
FIG. 18. RTG solution viscosity from 5-15% (w/v) for RTG v1 and v2 illustrating exponential increase in viscosity with increasing polymer concentration, as well as the effect of decreasing PNIPAm molecular weight.
Figure 19:
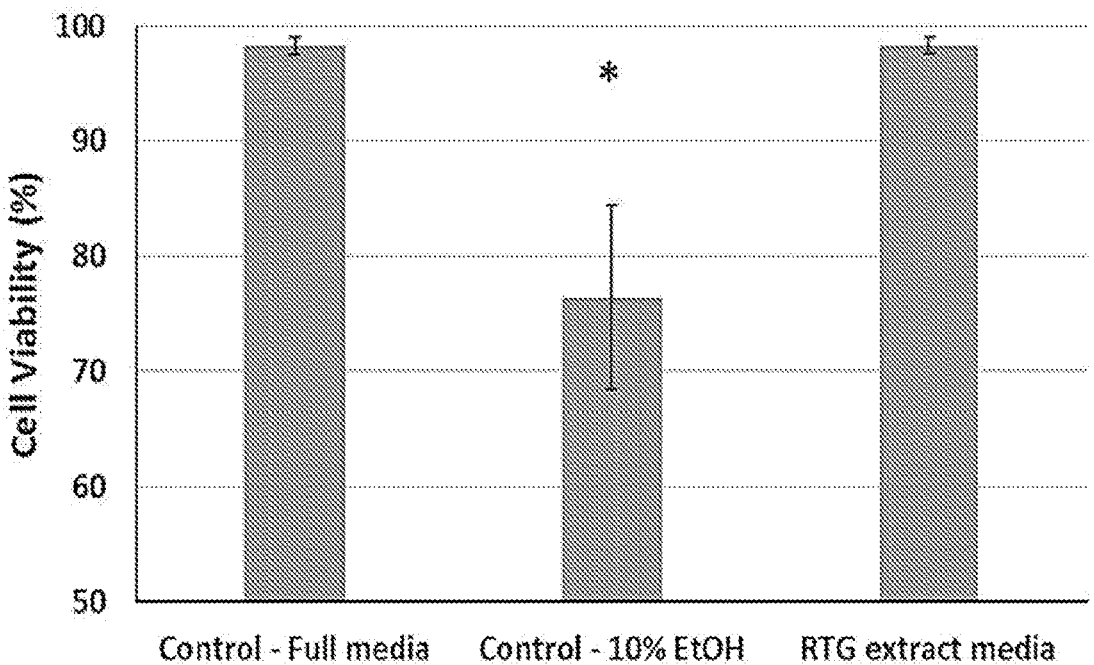
FIG. 19. HUVEC viability plot comparing RTG extract media with control media. * indicates statistically significant difference ($p<0.05$). No significant difference was observed in the cell viability between the full media and RTG extract media.

GPC was used to determine the molecular weight of the new version, in an embodiment, (RTG v2) of PNIPAm and that was compared to the original version (RTG v1). The molecular weight of RTG v1 was 131 kDa, while the molecular weight of RTG v2 was 91 kDa. The solution viscosity results are depicted in FIG. 18. Both versions showed an exponential increase in viscosity with polymer concentration, however, the incorporation of lower molecular weight PNIPAm in RTG v2 delayed the inflection point of the concentration-dependent viscosity profile. As a result, more than a 4-fold reduction in viscosity was observed at the 15% loading level for RTG v2. As a proof of concept, RTG v2 was also able to be loaded at 30% (w/v). This concentration may be useful in applications that use larger diameter catheters or needles for injections over short distances, for example. The reduced shrinkage (illustrated in the section on quantification of RTG solution viscosity, gel transition temperature shrinkage and compressive modulus) at this concentration make this an attractive alternative worthy of further investigation.

Assessment of RTG Cytotoxicity Using Live/Dead Cell Viability Assay:

Cytotoxic assessment of the RTG extract using a live/dead cell viability assay showed no significant decrease in cell viability compared to full EBM-2 media, for this example embodiment. The average cell viability was 98.2±0.7, 76.4±8.0 and 98.3±0.7 for full media, 10% EtOH added to media and RTG extract media, respectively. 10% EtOH was added as a positive control to confirm that dead cells could be detected and that the calcein and ethidium concentrations used in the assay were appropriate.

Figure 20:
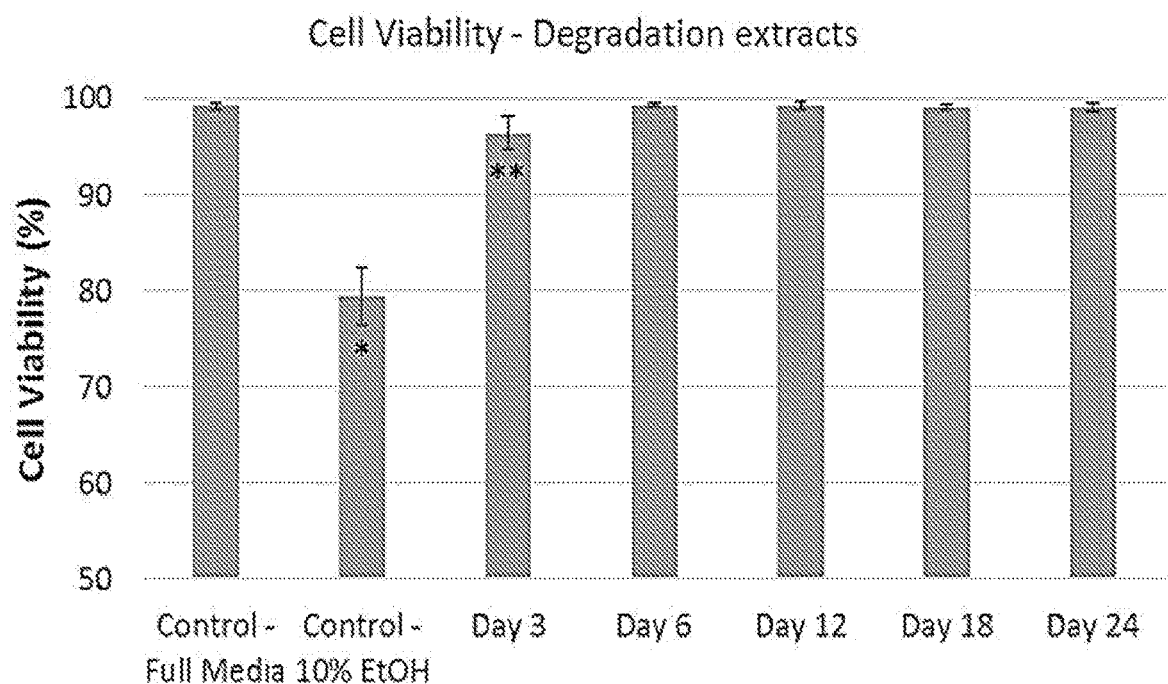
FIG. 20. HUVEC viability plot from live/dead assay tested on hydrolytic degradation extract material degraded for either 3, 6, 12, 18, or 24 days. The degradation extract material recovered, reconstituted, re-gelled and added to 5 mL of HUVEC media and incubated for 24 hours. The extract media was added to plated HUVECs and incubated for an additional 24 hours prior to running the live/dead assay. * and ** denote statistically significant differences ($p<0.05$).
Figure 21:
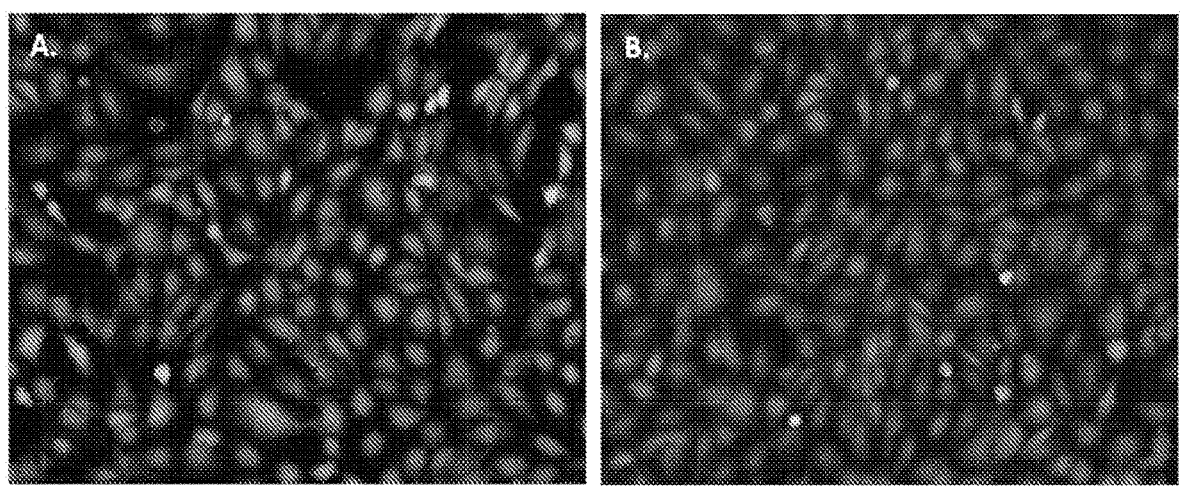
FIG. 21. Sample images from HUVEC live/dead cell viability assay showing A. RTG degradation day 3 extract, and B. unmodified control with full EBM-2 media. Images were taken at 100× magnification.

Hydrolytic degradation of the RTG was studied over the course of 24 days (described in detail in the section on hydrolytic and oxidative degradation results), and the degradation extracts were also assessed using the live/dead cell viability assay. Tests were conducted on samples that had been degraded for 3, 6, 12, 18, and 24 days. According to FIG. 20, days 6, 12, 18 and 24 all had cell viability percentages above 99% and were not statistically different from the untreated control media (99.2±0.4%). The exception was the day 3 extract which had an average cell viability of 96.4±1.7% and was significantly different from the control. Further tests would need to be conducted to determine the cause of this difference.

Figure 22:
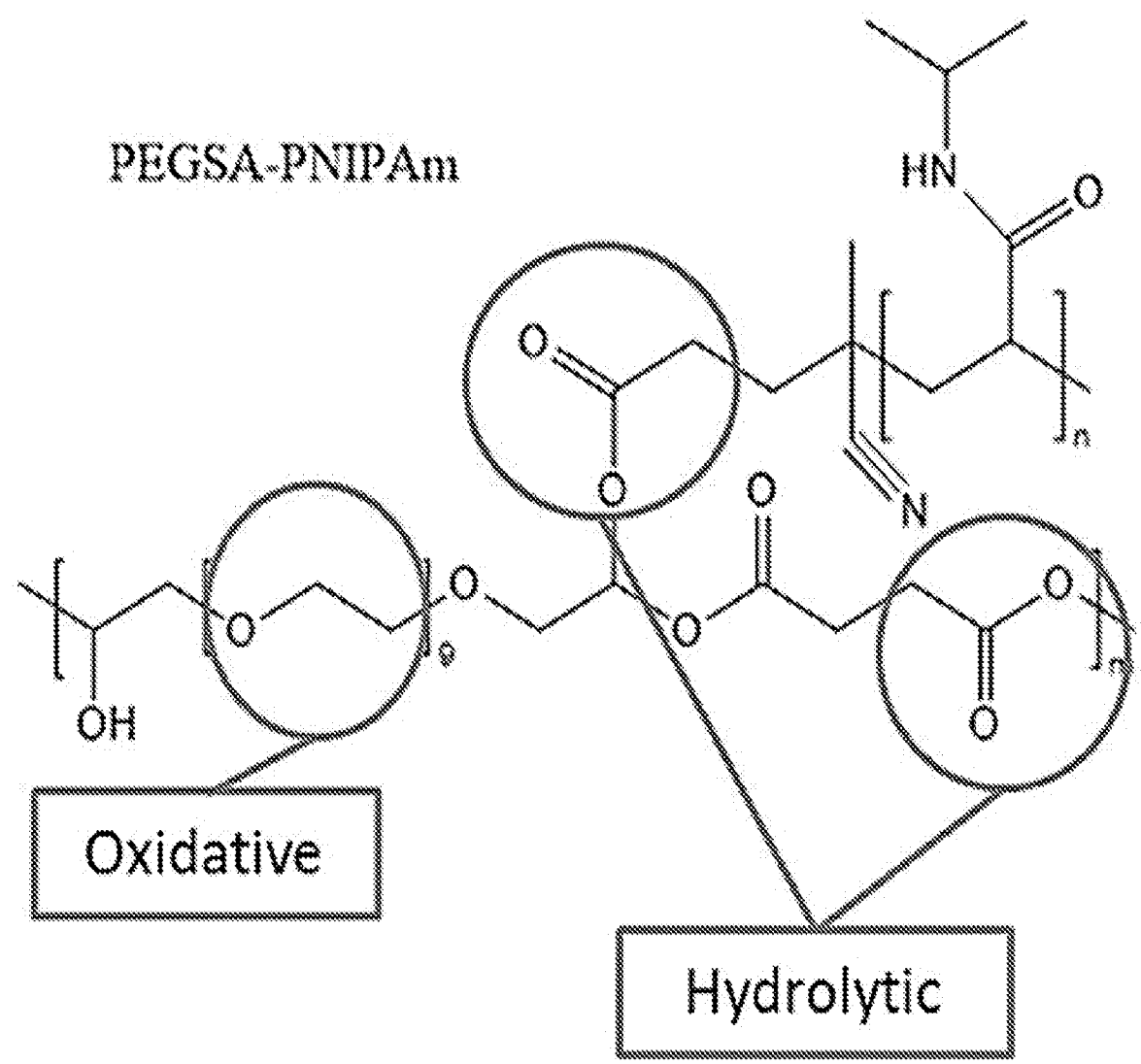
FIG. 22. Chemical groups in PEGSA-PNIPAm susceptible to degradation.
Figure 23:
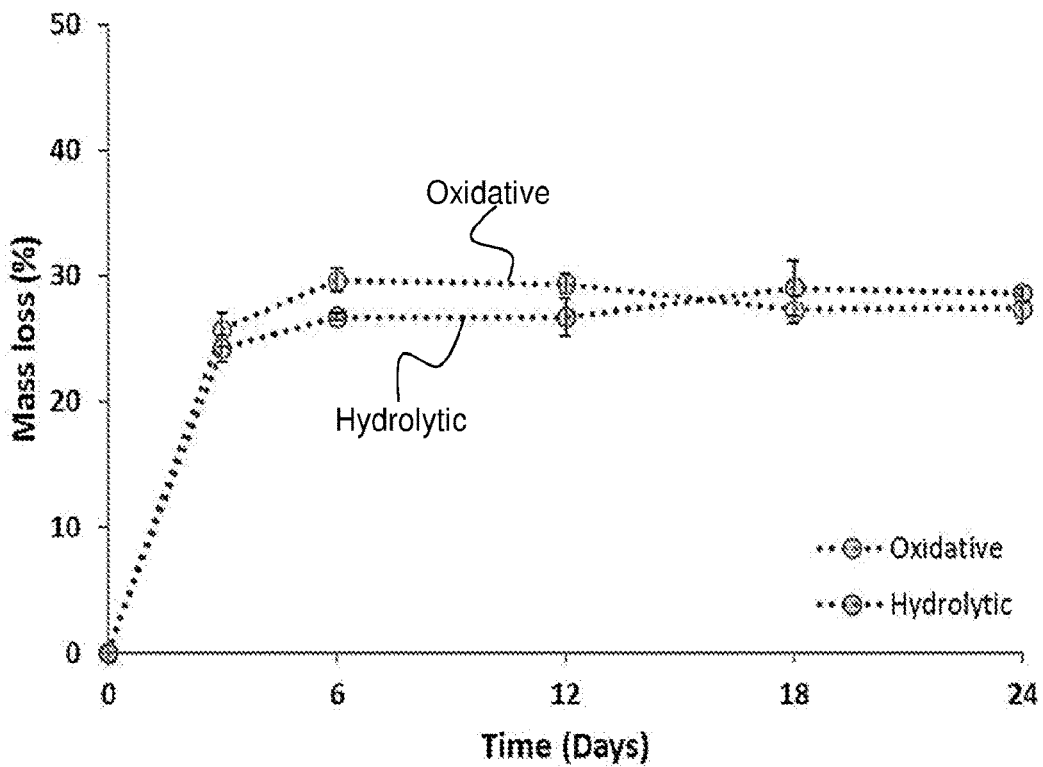
FIG. 23. Hydrolytic and oxidative degradation of RTG, measured after 3, 6, 12, 18 and 24 days. The data represents an average of three measurements at each time point.

Hydrolytic and Oxidative Degradation Results:

Preliminary assessment of long-term stability of the RTG was based on hydrolytic and oxidative degradation results. Enzymatic degradation was not examined for this study, but has been studied in similar RTG systems [9], [64]. The mechanisms of hydrolytic and oxidative degradation of polymers are shown in Table 2. FIG. 22 highlights the ester and ether groups within PEGSA-PNIPAm that are potentially susceptible to degradative processes.

TABLE 2

Hydrolytic and oxidative degradation mechanisms [65]:

HYDROLYTIC
Mechanism: Water molecules react with and cleave polymer chains, releasing small molecules

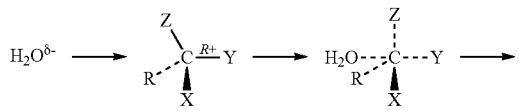

TABLE 2-continued

Hydrolytic and oxidative degradation mechanisms [65]:

$$HO-\underset{X}{\overset{Z}{\underset{|}{C}}}\cdots R + HY$$

Susceptible chemical groups: Acid anhydrides, esters

Figure 24:
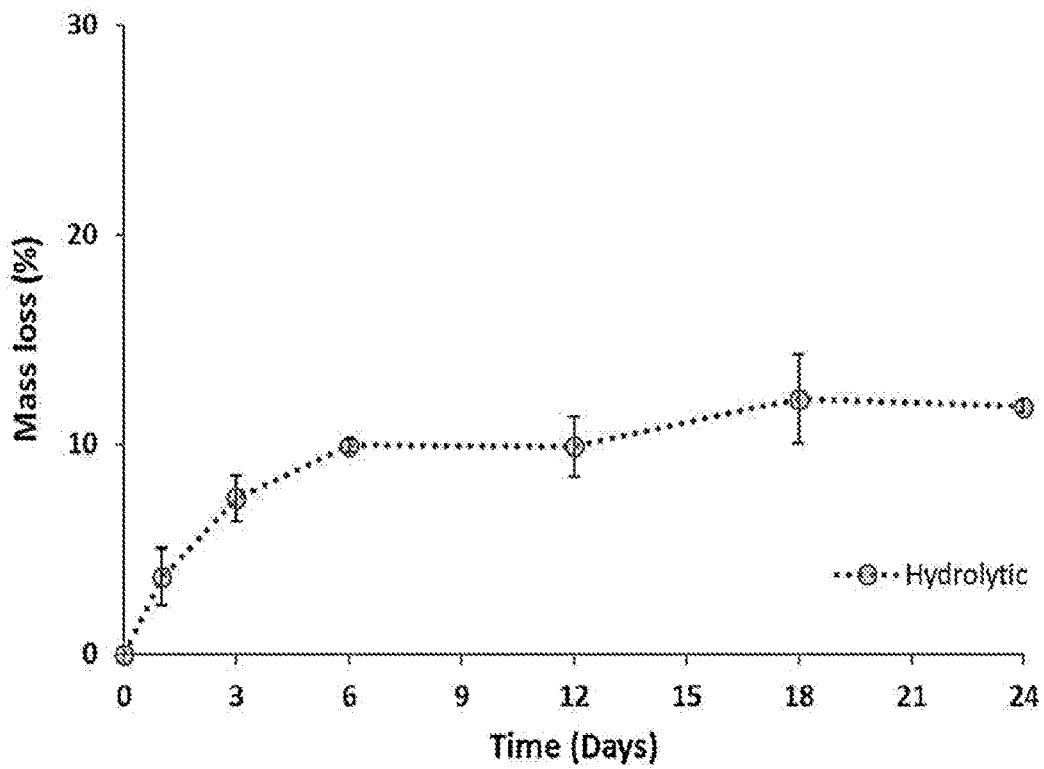
FIG. 24. Corrected hydrolytic degradation plot after initial debris removal, measured at 1, 3, 6, 12, 18 and 24 days. The data represents an average of three measurements at each time point.
Figure 25:
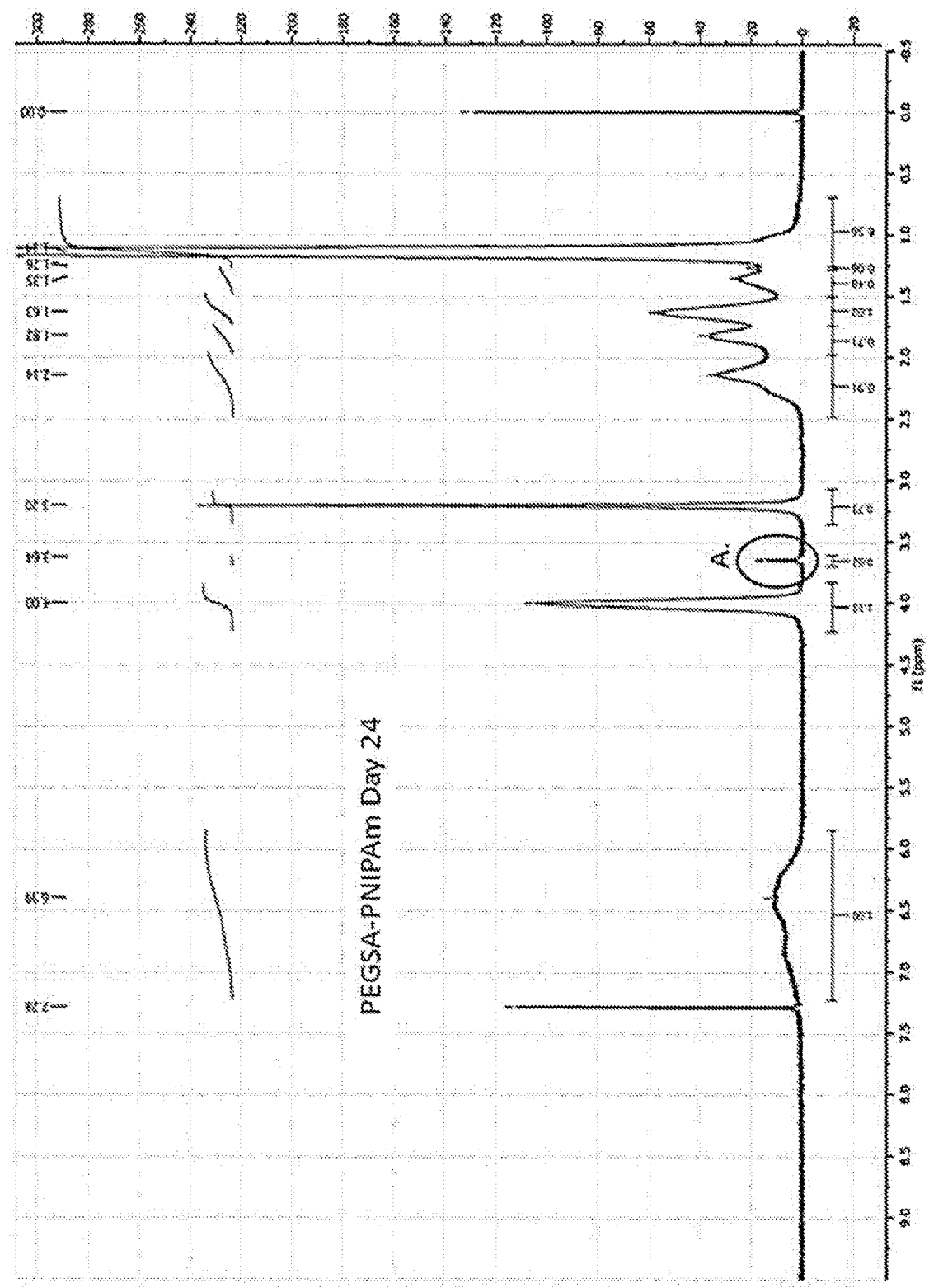
FIG. 25. NMR spectrum of PEGSA-PNIPAm after 24 days of hydrolytic degradation. A. Peak at 3.64 ppm corresponding to PEGSA methylene protons is present, although significantly reduced compared to the initial spectra (FIG. 12) which shows the presence of methylene protons from polyethylene glycol (a) at 2.67 ppm and succinic acid (b) at 3.64 ppm.
Figure 26:
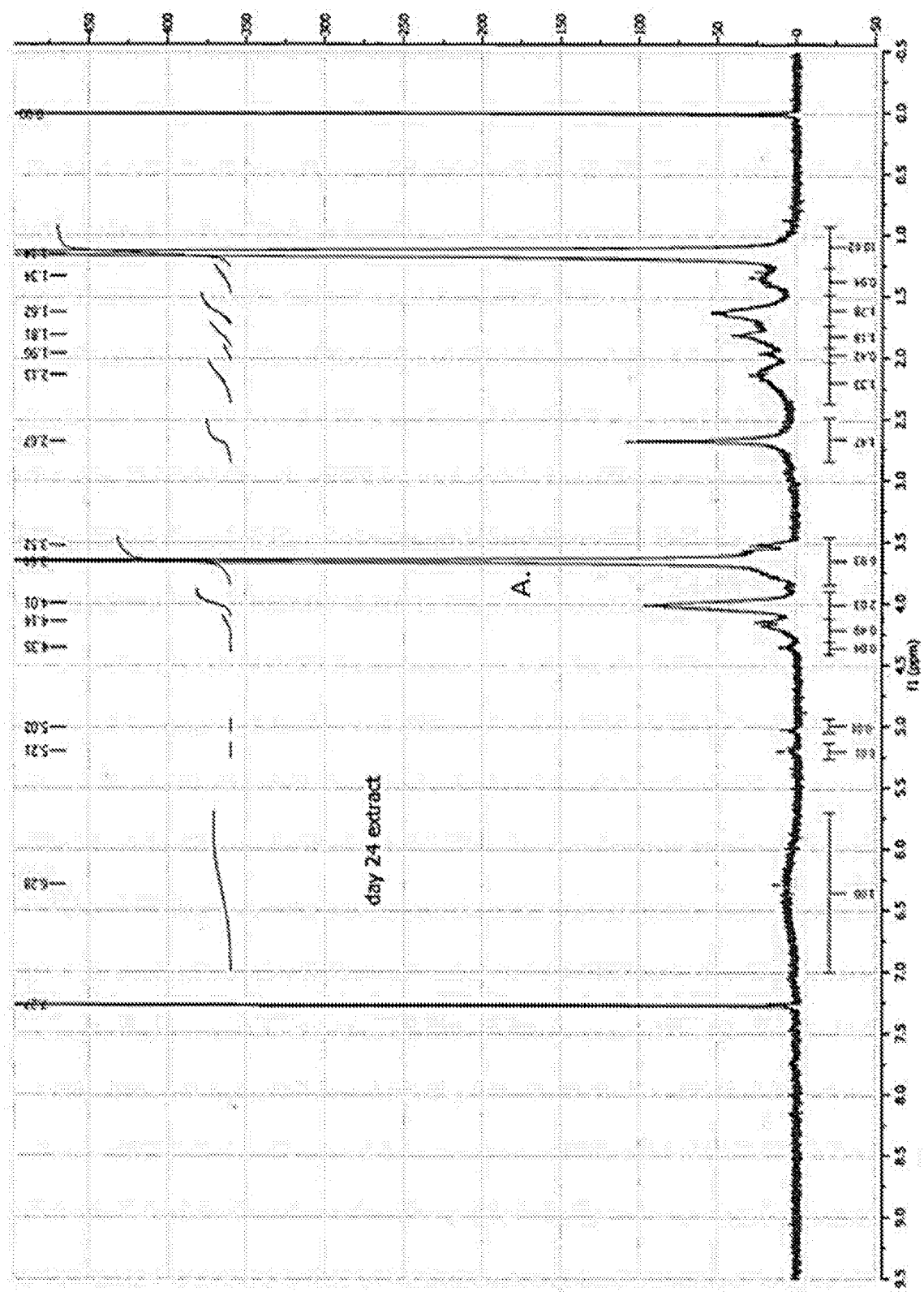
FIG. 26. NMR spectrum of PEGSA-PNIPAm extract after 24 days of hydrolytic degradation. A. Peak at 3.64 ppm corresponding to PEGSA methylene protons is strong, indicating higher quantities of PEGSA components. Some PNIPAm is also present (4.01 ppm).

OXIDATIVE
Mechanism: Peroxides produced by inflammatory cells can be oxidized by metal ions (Fe2+, Co2+), creating reactive oxygen species (•OH) which can cause degradation
$Co^{++} + H_2O_2 \rightarrow Co^{+++} + HO^- + HO•$
Susceptible chemical groups: Amines, ethers, urethanes The initial hydrolytic degradation tests resulted in a 28.6±0.3% mass loss after 24 days, for this example embodiment. Similarly, initial oxidative degradation resulted in a 27.4±1.1% mass loss after 24 days in a 0.1 M CoCl2/H2O2 solution. The majority of mass loss occurred within the first three days in both hydrolytic and oxidative degradation tests. Prior to the three day mark in the shaking incubator, the solution in the hydrolytic samples appeared cloudy and visible fragments of polymer debris was visible in both hydrolytic and oxidative samples. As a result, a second set of tests were performed where the samples were gelled and placed in the shaking incubator for 15 min, at which point three samples were removed, debris was washed out, and the samples were dried. Subsequent samples were then removed at one and three days and mass loss was measured relative to the initial "debris-removed" samples to obtain corrected mass loss measurements, shown in FIG. 24.

Figure 27:
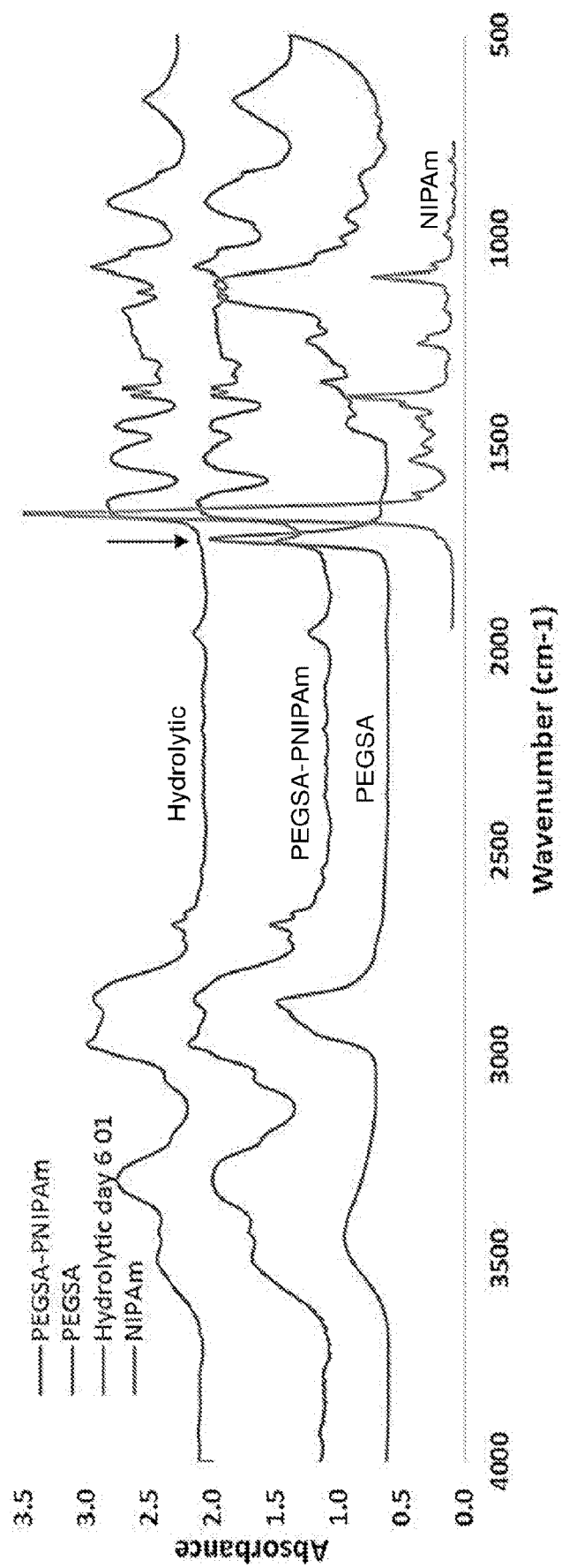
FIG. 27. FTIR spectra of PEGSA-PNIPAm after 6 days of hydrolytic degradation (green). The arrow indicates the peak corresponding to PEGSA esters is significantly reduced at this time point.

Although the amount of mass loss via hydrolytic and oxidative degradation have been quantified, it is equally important from an FDA biocompatibility standpoint, to understand what the degradation products are and how the biocompatibility profile of the degraded material may differ from that of the starting material. NMR and FTIR are useful in beginning to answer those questions. NMR showed a reduction in PEGSA in the bulk material over days 3, 6, 12, 18 and 24. The spectra showed a relative reduction in the intensity of the peak at 3.64 ppm, corresponding to methylene protons on PEGSA. Furthermore, there was a high concentration of PEGSA compounds, but a low concentration of PNIPAm components in the 24 day extract material. The FTIR spectra also indicate a reduction PEGSA in the sample (FIG. 27). It seems likely that at least a portion of the PEGSA backbone was being degraded over time, and probably first at the surface of the RTG. The most likely location for degradation would be the ester in the backbone of the PEGSA molecule, as opposed to the more sterically hindered ester joining the PNIPAm to the PEGSA. However, the overall appearance of the RTG sample did not change in physical appearance apart from the first hour when the shrinkage occurred. As long as the temperature remained at 37° C., the PNIPAm remained physically gelled.

Limitations of the Study:

Quantifying the amount of oxidative degradation may present technical challenges in some instances because some of the samples had a residual blue color remaining at the end of testing, even after thorough washing. This observation is consistent with the possible presence of leftover $CoCl_2$ salts, which may impact the final sample weight. The results indicate similar levels of oxidative degradation compared to hydrolytic degradation; however, since the protocol calls for a 20% $H_2O_2$ mixture with water, it is possible that some hydrolytic degradation still occurs in samples being tested for oxidative degradation.

An important consideration is debris/small fragments of RTG in the solutions. Example situations include the material slightly adhering to the glass surface of the vial during gelation, but glass vials were selected over plastic conical tubes because the material is even more adherent to plastic. Furthermore, the cylindrical disk geometry is not particularly physiologically relevant. It would have been more optimal to use a gelled sample extruded from a catheter, but getting consistent initial weights this way would have been very difficult. In performing in vitro testing of the material delivered from a catheter, there did not appear to be a significant amount of debris or fragmentation, as long as the material was not extruded too rapidly.

Figure 28:
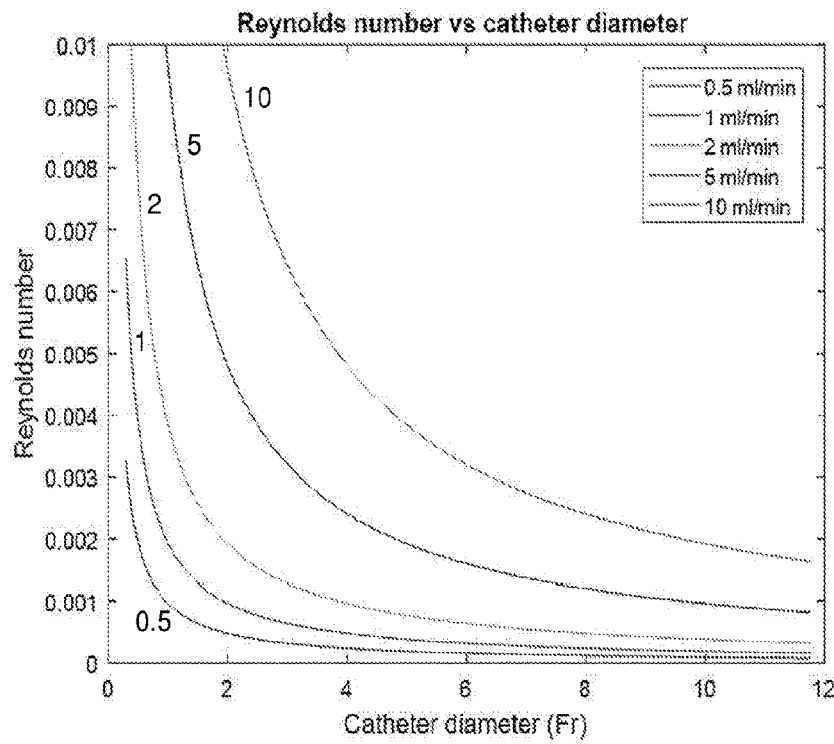
FIG. 28. Reynolds number as a function of catheter size for RTG injection rates varying from 0.5 to 10 ml/min. Re<<2000 indicates laminar flow.

Analytical Model Results:

The results from the analytical models are helpful in predicting how the material will perform in vivo. Reynolds number calculations were performed to confirm that the RTG was within the laminar flow regime at the required delivery flow rates and that Poiseuille's Law could be applied. The plot in FIG. 28 indicated the flows were laminar at a variety of flows and catheter diameters.

$$Re = \frac{\rho u D}{\mu}$$

Figure 29:
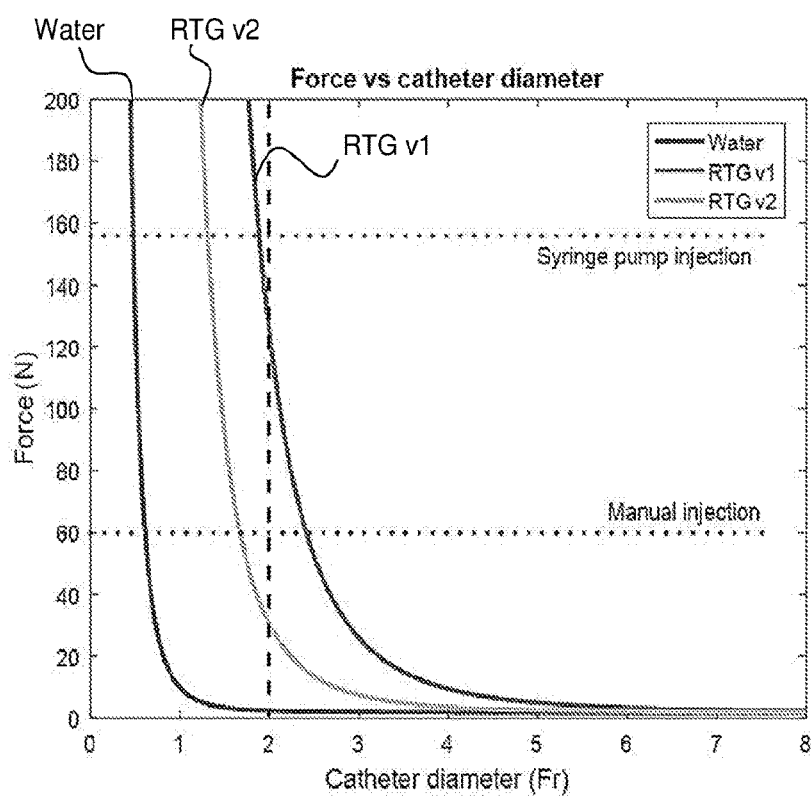
FIG. 29. Syringe injection force plotted versus catheter diameter for water, RTG v1 and RTG v2 at an injection rate of 1 ml/min. The vertical black dashed line denotes a 2 F microcatheter. The model indicates that the lower viscosity RTG v2 will be injectable by hand, while the higher viscosity RTG v1 will require mechanical assistance to inject.

FIG. 29 illustrates the injection forces required to deploy either water, or two different viscosity RTGs (15% polymer concentration) from a 1 ml syringe at a flowrate of 1 ml/min through a 150 cm catheter, in an embodiment. The average viscosities as reported in the section on quantification of RTG solution viscosity, gel transition temperature, shrinkage and compressive modulus were used in the model. The horizontal dotted lines indicate the maximum syringe pump injection force and the average thumb force if injecting manually [66]. The model shows that using the lower viscosity RTG v2, the injection force is approximately 30 N for a 2 F microcatheter; easily accomplished manually. For the higher viscosity RTG v1, an injection force of more than 120 N would be required, which would approach the limit of a standard syringe pump.

Figure 30:
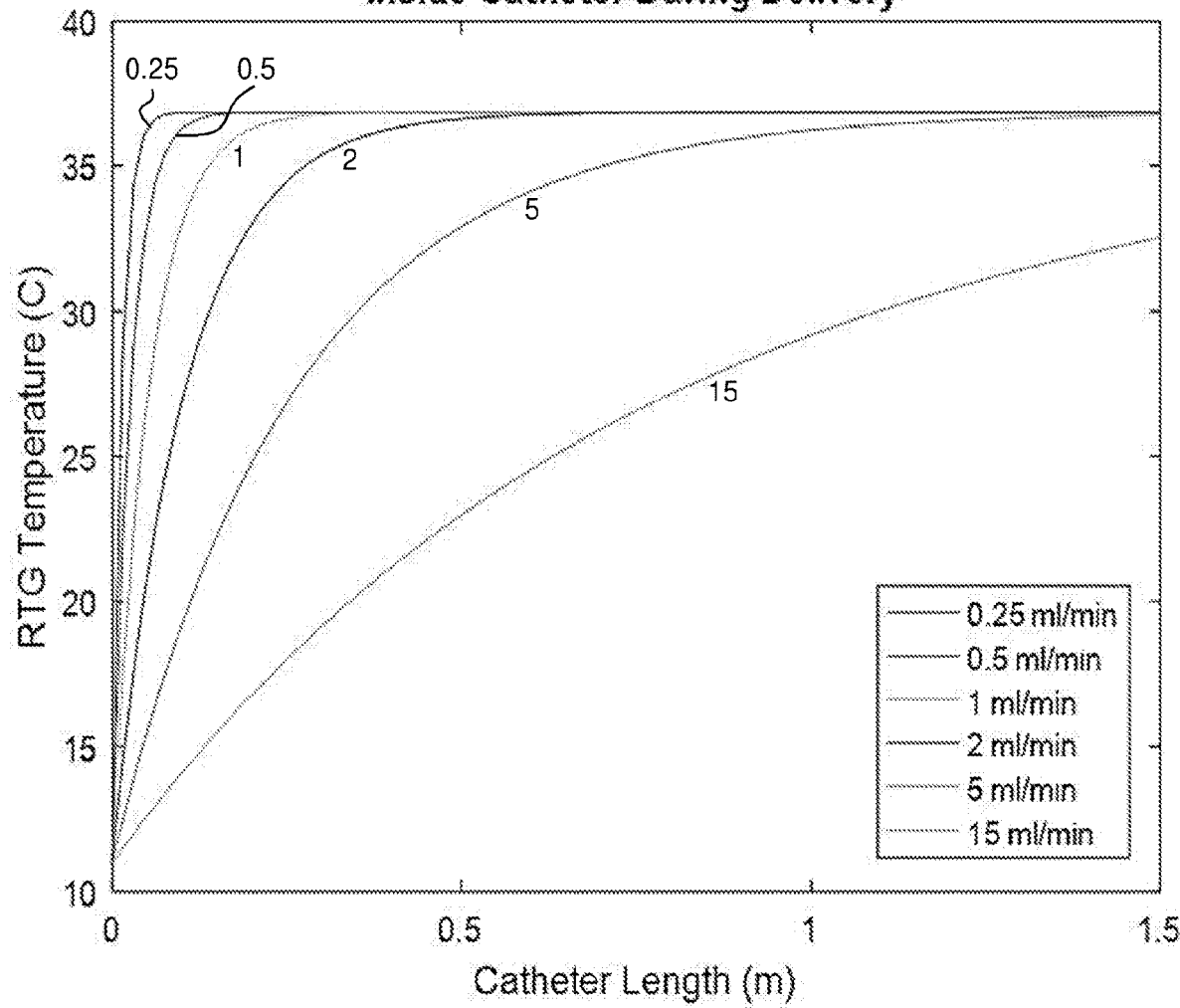
FIG. 30. RTG solution temperature as a function of catheter length shown for varying injection flowrates.

The heat transfer model results are shown below in FIG. 30. The plot displays the average temperature of the RTG versus catheter length for relevant injection rates of 0.25, 0.5, 1, 2, 5 and 15 ml/min. The model indicates that at a starting RTG temperature of 11° C., for all flowrates except 15 ml/min, the RTG will reach gelation temperature before it reaches the end of the catheter. For the situation of a parallel-flow heat exchanger model, the RTG temperature profiles are similar, but the final temperatures are reduced slightly in the higher flowrate situations (>2 ml/min). Although the results do not necessarily project RTG flow will cease in these scenarios, the injection force is likely to increase significantly. The results of this model suggest that using a cooling outer sheath catheter would be useful to delay the onset of RTG gelation.

Figure 31:
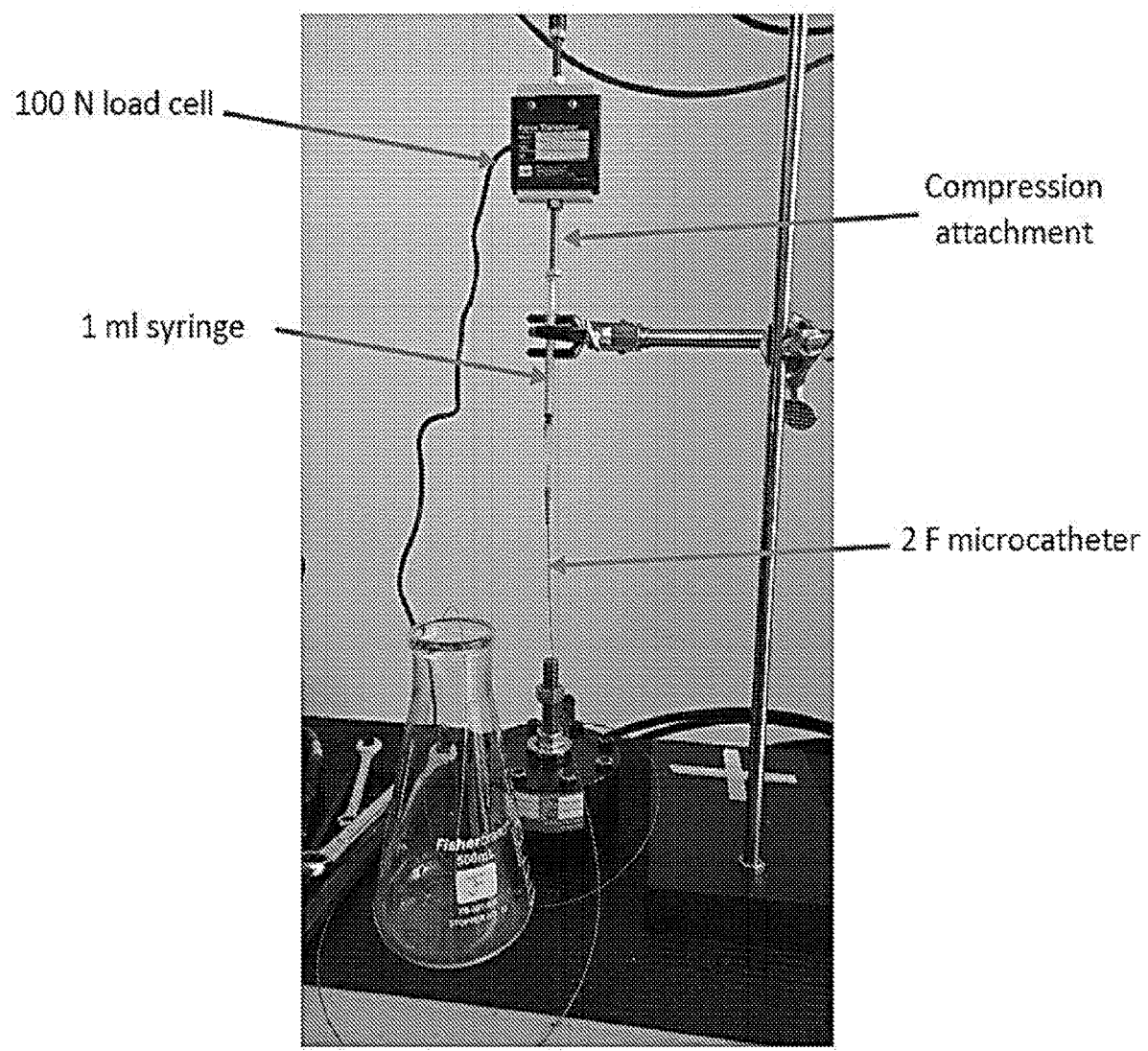
FIG. 31. Test apparatus for measurement of force required to inject RTG through a 2 F microcatheter using a 1 ml syringe.
Figure 32:
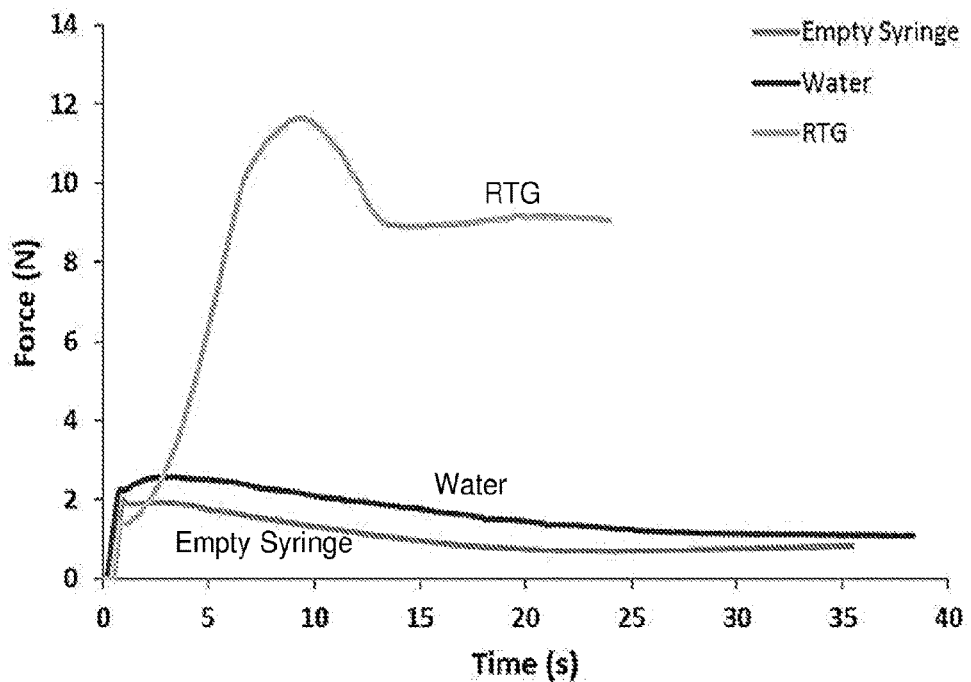
FIG. 32. Representative plots of extrusion force versus time for the empty syringe, water, and RTG.

Validation of Pressure Drop and Heat Transfer Through Catheter:

The catheter pressure drop model was validated by measuring the syringe injection force using a mechanical testing system with a compression fixture connected to a 100 N load cell (FIG. 31). A 1 ml syringe was mounted vertically and connected to an ev3 Echelon 14 2 F microcatheter. The actuator was lowered at a rate of 57 mm/min, which corresponded to a 1 ml/min injection rate from the syringe. The force was recorded and plotted versus time. The test was run using either an empty syringe, water, or RTG. All materials were tested in triplicate.

The heat transfer model was validated by injecting cold water through an 8 F catheter (2.4 mm ID) submerged in a 37° C. water bath and measuring the outlet temperature using a digital k-type thermocouple with a wire probe. The distal 250 mm of the catheter was submerged in the water bath and the catheter ID was approximately 2.4 mm. Cold water with an average starting temperature of 11.0±0.5° C. was injected through the catheter at a flow rate of 15 ml/min. The cold water outlet temperature at the distal end of the catheter was 24.5±0.3° C.

The gelation point of the RTG was visually assessed while injecting though transparent polyimide tubing at a rate of 1 ml/min. The solution inside the tubing became opaque after approximately 20 cm from the point where the tubing entered the 37° C. water bath; however it still continued to move through the remainder of the tube, forming a gelled coil upon exit.

Comparison of Models with Experimental Results:

The injection force required for delivery as determined by the analytical model compares reasonably well with the experimental results. With water as the injection fluid, the average measured peak force for a 2 F catheter at a flow rate of 1 ml/min was 2.6±0.3 N, compared to 2.3 N as calculated by the model. Interestingly, the for the RTG injection force, the experimental results were significantly lower than the theoretical value; 11.2±0.4 N for the experimentally measured force versus 30.7 N calculated by the model. One possible explanation for this difference may be due to surface treatment on the inner wall of the catheter reducing the coefficient of friction between the RTG solution and the catheter wall. Many catheters are treated with a hydrophilic coating designed to create a lubricated surface between the catheter and the surroundings [67]. This would have the effect of reducing the measured syringe injection force.

Figure 33:
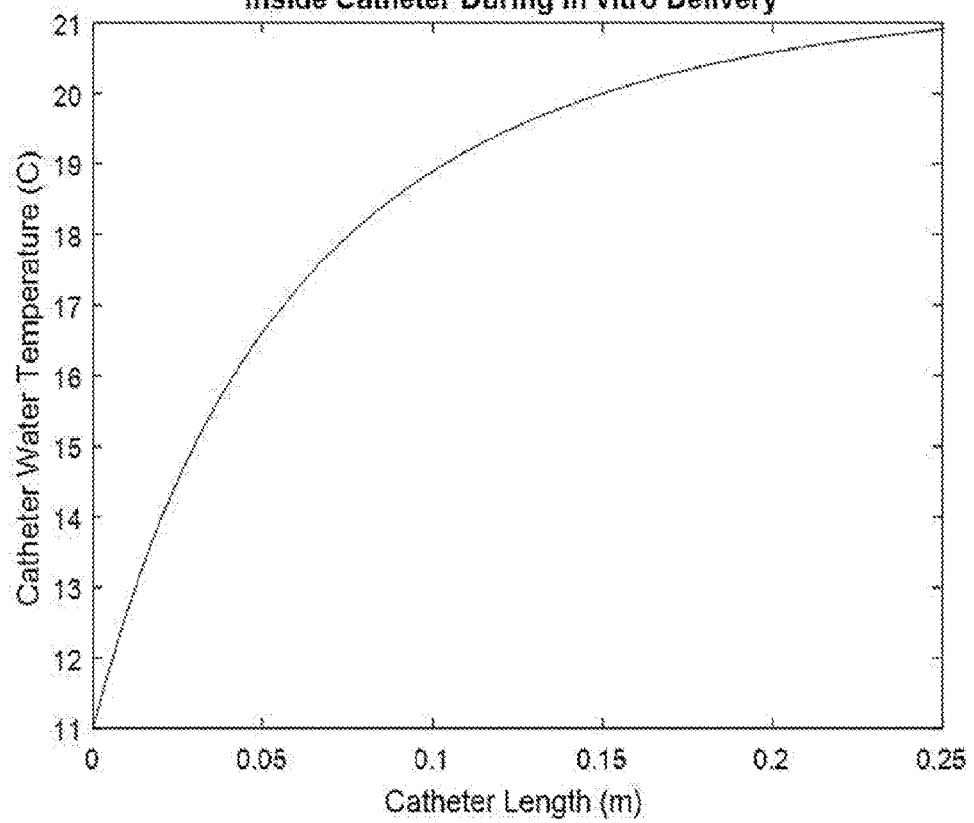
FIG. 33. Water temperature inside the catheter as a function of catheter length.

FIG. 33 shows the output temperature from the tip of the catheter according to the analytical heat transfer model. The profile describes the outlet temperature of water moving through an 8 F catheter at 15 ml/min with an inlet temperature of 11° C. The model assumed the surrounding water bath was at 37° C. and was moving at 6 ml/min counter to the water flow inside the catheter. The model indicated a water outlet temperature of approximately 21° C. at a distance of 0.25 m away from the catheter entrance point into the water bath. This temperature agreed reasonably well with the experimentally measured cold water outlet temperature of 24.5±0.3° C.

Figure 34:
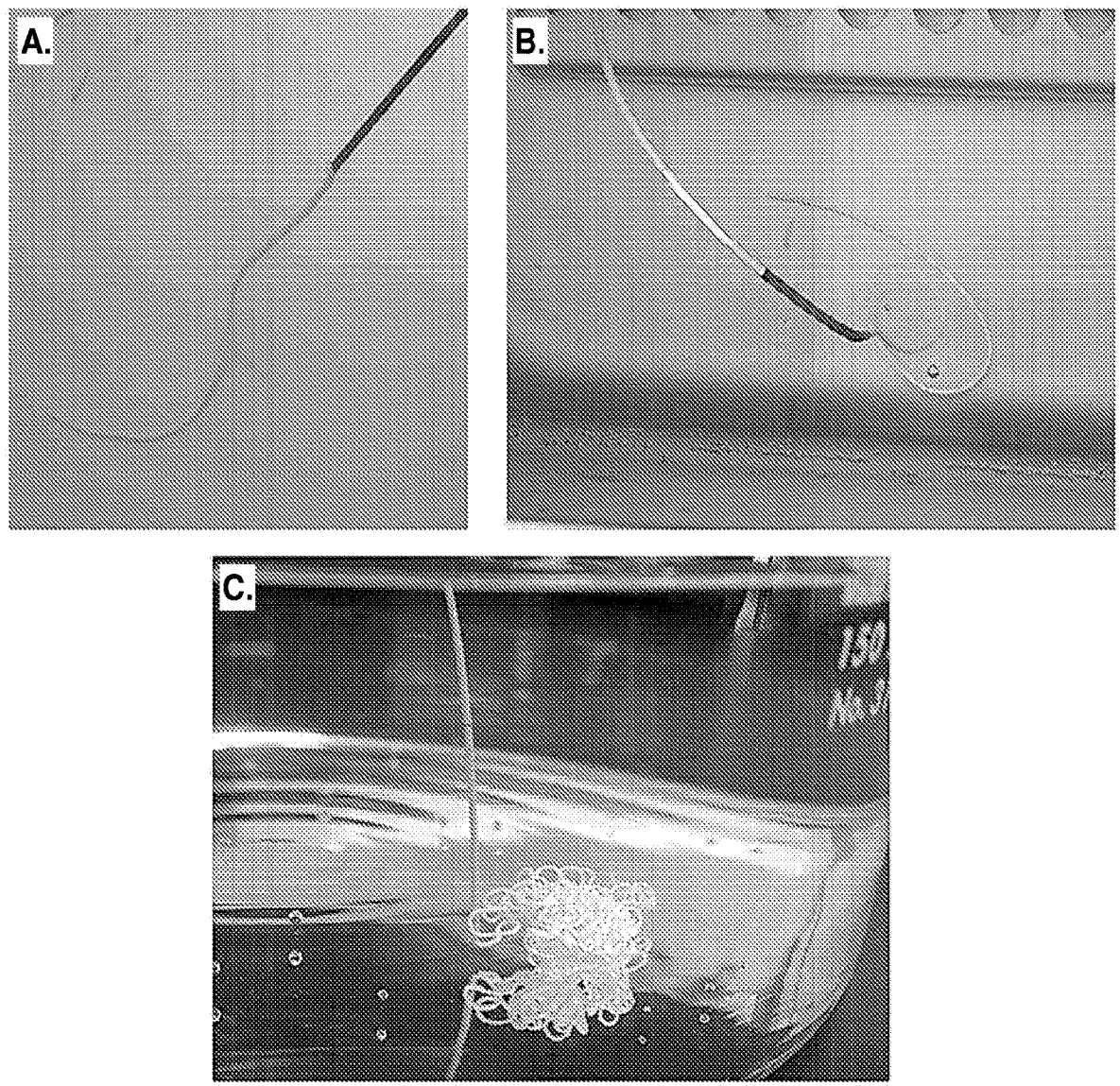
FIG. 34. RTG delivery through progressively smaller catheters: A. 6 F, B. 5 Fr and C. 1.9 Fr microcatheter. Approximately 5-10 cm of the distal end of each catheter was placed in a water bath at 37° C. prior to, and during injection.

In Vitro Testing:

Optimization of RTG for Microcatheter Delivery:

Reducing the molecular weight of PNIPAm enabled microcatheter delivery. Using the in vitro benchtop setup, a 15% (w/v) concentration of RTG v2 in phosphate-buffered saline was successfully delivered through 6, 5 and 1.9 Fr catheters, in this example embodiment. Pictured in FIG. 34, RTG injection through the 1.9 Fr microcatheter formed a solid, coiled gel upon contact with a 37° C. water bath (155 cm catheter length, 1 mL injection syringe, 1 mL/min flow rate). Higher viscosity RTG v1 was injectable by hand only through the 5 and 6 Fr catheters, in an embodiment. Both the diameter of the catheter and the orientation of the catheter tip appeared to influence the RTG delivery conformation. The 6 F catheter was straight-tipped, and the RTG was deployed as a long, relatively straight noodle. The 5 F catheter was a guide catheter with an angled tip, and this caused the RTG to flow out in a helical pattern. The microcatheter exhibited slight oscillatory behavior during delivery, which allowed the RTG to extrude in a random coil pattern.

Simulating Delivery Under Physiological Pressures, Through Tortuous Vasculature and Assessing Space-filling Capabilities:

The RTG was tested in a number of in vitro scenarios in order to better estimate occlusion potential and to determine the best methods for use. The RTG can be delivered continuously through a microcatheter where the majority of the length of the catheter is exposed to 37° C. If flow was halted for more than approximately 10 seconds, the material gelled completely within the catheter and injection could not be resumed. When the volume of RTG to be delivered was sufficient, the coil could be broken by either aspirating the syringe quickly, or moving the catheter tip along the side wall of the vessel to break off the segment. In some cases, the RTG could be aspirated and re-extruded in back-and-forth manner.

Figure 35:
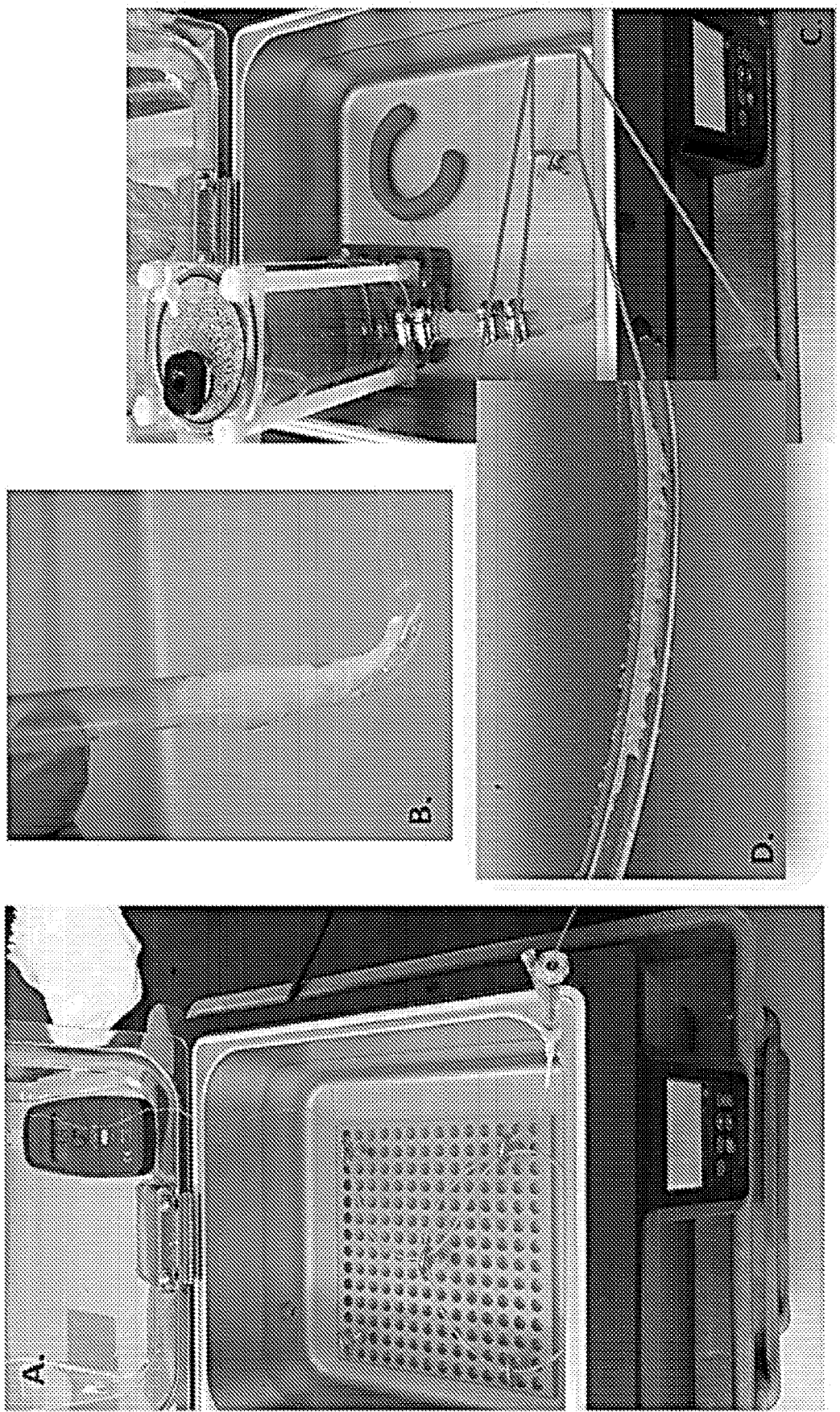
FIG. 35. Benchtop setup to test RTG in vitro performance. A. Simulated tortuous vasculature using a microcatheter with outer sheath catheter to cool the RTG. B. Space-filling capabilities of the RTG was tested on a modified Pasteur pipette. The RTG was first injected through a 5 F catheter to fill the majority of the space and so the material would not flow past the curved region of the pipette. This was followed by microcatheter RTG injection to help fill smaller void spaces left behind by the shrinking of the first fill. C. Simulated delivery under physiological pressure was accomplished using silicone tubing connected to a water reservoir filled creating the equivalent of 10 mmHg pressure. D. RTG injected into a 2 mm diameter section of tubing using the 2 F microcatheter.

A reservoir filled with 37° C. water was filled to a height of approximately 13.5 cm, or equivalent to 10 mmHg and connected to 2 mm diameter silicone tubing to simulate RTG delivery under physiological pressures and flowrates (FIG. 35, C). A three-way adapter was connected to the end of the tubing which allowed a 2 F microcatheter to be inserted into the tubing either with no flow or full flow. If the RTG was filled with no flow present, the RTG filled a section of the tube similar to FIG. 35, D. Once the flow was turned on, the RTG held in position for a maximum of 5 minutes before slipping or migrating out of the tube. However, during some tests, the material was immediately carried out of the tube when flow was initiated. When the RTG was injected into the tube with the direction of flow, the material formed a long string and was carried downstream and out of the end of the tube. When the RTG was injected opposite to the flow direction, the gel formed a tight coil, slightly pushing the catheter in the retrograde direction. No reflux around the catheter was observed in this situation and the RTG held in place for about 2 minutes before migration occurred, in an embodiment.

An 8 F catheter (used as a sheath) was threaded through eye-bolts connected to a metal plate in the water bath to simulate tortuous vasculature (FIG. 35, A.). A 2 F microcatheter was threaded through a rotating hemostatic valve (tuohy borst adapter) on the proximal end of the sheath catheter. Cold water (5-10° C.) was flushed through the sheath catheter at 15 ml/min. The RTG was manually injectable through the tortuous pathway and formed either a coiled or helical gel in the water bath. The RTG was injectable continuously either with or without the cooling sheath catheter. When used, the sheath catheter maintained an outlet temperature between 25° C. and 32° C. at the distal end of the 8 F catheter. If the distal end of the sheath was too close to the distal end of the microcatheter, the RTG gelation was delayed and a milky, white cloud of material was dispensed rather than a rigid coil, in an embodiment. Aligning the microcatheter at least 5 cm downstream of the distal end of the sheath avoided this problem, in an embodiment.

Additional space-filling tests were conducted by filling a modified Pasteur pipette with the RTG (FIG. 35, B.). RTG was injected through a 5 F catheter to fill the majority of the space and to prevent material from moving past the curvature in the pipette. This was followed by a secondary filling with the microcatheter to fill in void space and areas between the walls and the initial fill. The RTG conformed to the non-uniform structure of the pipette and filled the space well without flowing beyond the curved region at the bottom; however water did leak slowly through the pipette, likely due to small areas of void space and the RTG shrinking over time, in an embodiment.

Assessment of RTG as a Potential Embolic Agent:

In this study, a practical approach was taken not only to optimize the RTG, in an embodiment, for delivery through a microcatheter but also to begin to develop a biocompatibility profile of the material based on FDA guidelines. Successful microcatheter delivery can expand the clinical applications of this experimental embolic material. Lowering the concentration of polymer in the system, altering polymer microstructure or reducing the molecular weight of the polymer are all valid approaches to reducing the solution viscosity [68]. The disadvantage to reducing polymer concentration is the potential for a simultaneous reduction in mechanical integrity of the RTG. Modifying the polymer microstructure (from linear or branched polymer to spherical micro- or nanoparticles) could reduce viscosity and increase shear-thinning capability of the material, but would involve significantly altering the chemical synthesis [68]. Reducing polymer molecular weight resulted in more than a four-fold reduction in both the viscosity and the required injection force from RTG v1 to RTG v2, in an embodiment. This enabled successful delivery of the RTG solution through a 1.9 Fr microcatheter. The injections were performed by hand, without aid of a syringe pump or power injector.

Gelation time and temperature are additional critical aspects of the material. If gelation occurs too rapidly, injection may become difficult and catheter entrapment could occur. Alternatively, if the material exhibits delayed gelation, embolization could occur downstream of the intended target vessel area. For RTG v2, gelation occurred within two seconds of making contact with the 37° C. water bath. Furthermore, a LCST of 35° C. ensures complete gelation should occur at body temperature and the material will remain gelled within most closed vascular spaces.

Cell viability assay and degradation assessments indicated that although the material experienced a limited mass loss over time, the extracted material was non-cytotoxic to the HUVEC line. Although the probability of mass loss or fragmentation from the bulk RTG causing a downstream embolism should be studied with in vivo testing, it was observed that at injection rates of less than 2 ml/min, the gel remained cohesive and intact upon in vitro delivery from the catheter and no fragmentation was observed.

Example challenges are initial volumetric shrinkage, premature gelation inside the catheter when injection is interrupted, and determining the optimal gel conformation that will yield the best occlusive results.

Figure 36:
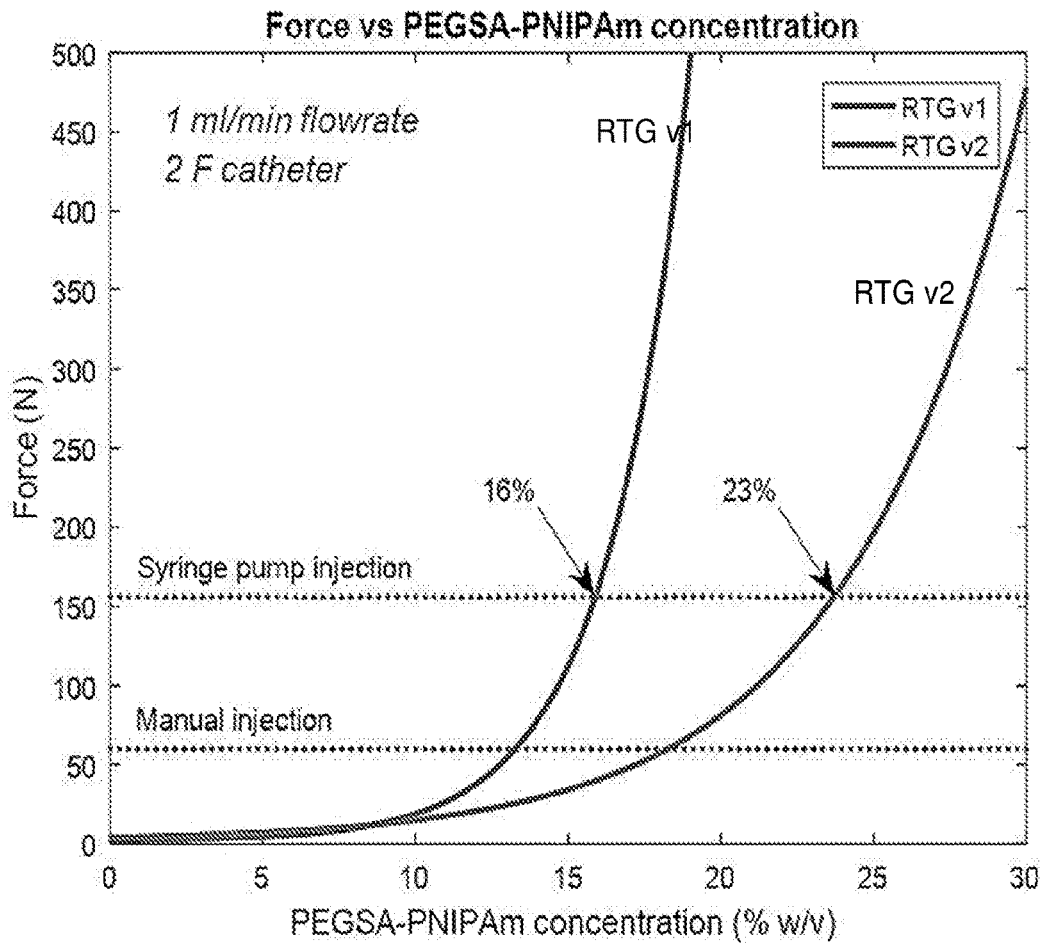
FIG. 36. Injection force versus polymer concentration for the two versions of RTG.

To address the shrinkage challenge, the results from the analytical model can be used to help predict if using a higher polymer concentration could be both beneficial and practical. As is evident from the shrinkage measurements, doubling the polymer concentration from 15% to 30% reduced the maximum shrinkage by a factor of eight, in an embodiment. Combining results from pressure drop model and measured viscosity results, the maximum concentration can be determined which can still be extruded from a 2 F microcatheter, either manually or via mechanical assistance (FIG. 36). Utilizing the lower viscosity version of the RTG it may be possible to feasibly inject a 23% RTG solution and this would potentially lower the shrinkage by more than 50%. It would also be worth exploring the possibility of synthesizing lower molecular weight PNIPAm as a means to controlling the shrinkage. Additionally, increasing the PEG molecular weight may have an effect of increasing hydrophilicity and reducing shrinkage during gelation.

Figure 37:
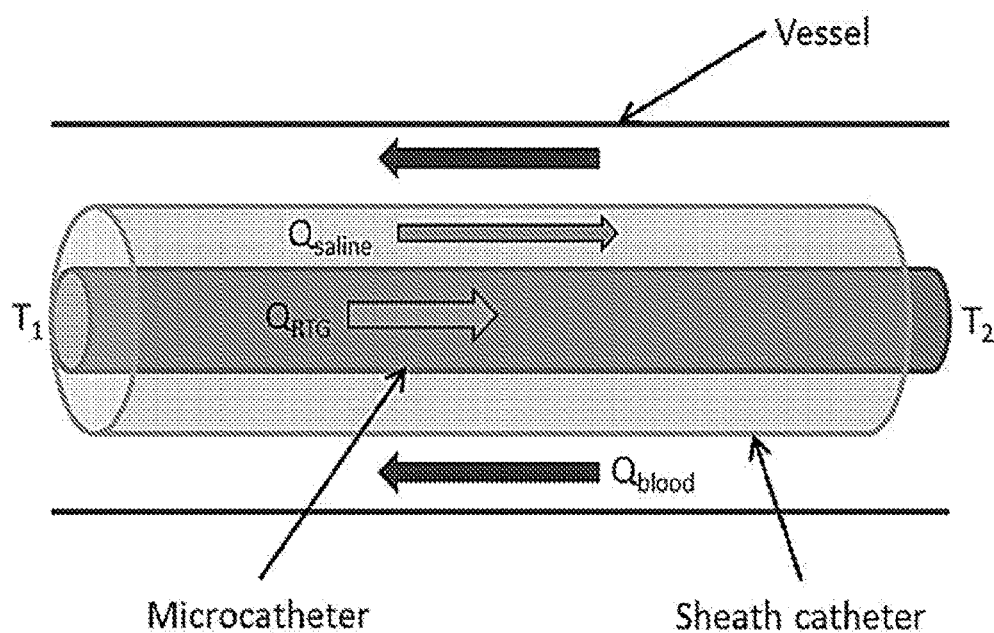
FIG. 37. Diagram of insulating sheath catheter used to limit temperature rise of RTG inside microcatheter.

Premature gelation in the catheter can be partially alleviated using an outer sheath catheter to serve as an insulating device. To assess this option, the heat transfer model was adapted to include an 8 F sheath catheter running cold saline at a flow rate of 15 ml/min, designed to act as an insulating barrier between the RTG inside the microcatheter and the blood (FIG. 37).

Figure 38:
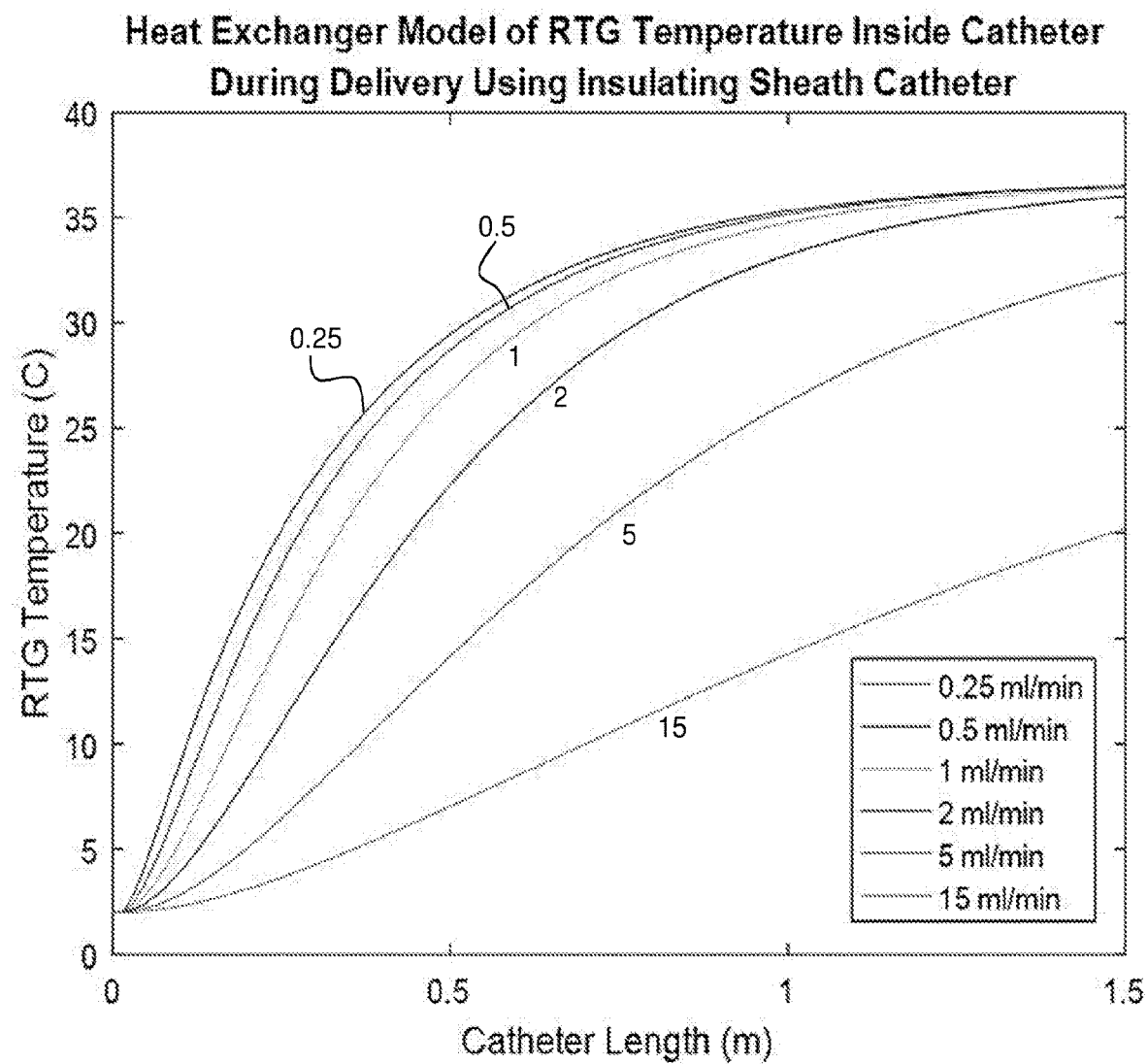
FIG. 38. Heat transfer model incorporating a sheath catheter running cold saline to cool the RTG inside the microcatheter. The model assumes a 2 F microcatheter, 8 F sheath catheter, 2° C. initial RTG temperature, 2° C. initial saline temperature, 15 ml/min saline injection rate flowing parallel to the RTG, and counter-flow venous blood flow at 125 ml/min.

The model results showing the RTG temperature versus catheter length are shown in FIG. 38. Convective heat transfer occurs from the blood to the cold saline inside the sheath catheter, and subsequently from the saline to the cold RTG as the saline starts to warm. Compared to the initial heat transfer model results (FIG. 30), incorporating the sheath catheter delays the temperature rise of the RTG as it is flowing through the microcatheter. For example, in FIG. 30 (no sheath catheter present) with an RTG flowrate of 1 ml/min, the model indicates the RTG will reach 35° C. after approximately 0.3 m inside the catheter. Utilizing the model with the cooling sheath catheter, the RTG at the same flow rate should reach 35° C. after 1.05 m. In vitro testing of RTG delivery both with and without the sheath catheter present was conducted in a 37° C. water bath. In both situations, the RTG was in the gel state as it was evacuated from the catheter, indicating that the RTG was at or above the gel temperature of 35° C. With the sheath catheter present, sustained delivery of the entire syringe volume was possible when the full catheter length was in the water bath. Without the sheath catheter, only partial RTG delivery was possible before the injection force exceeded the maximum syringe pump injection force and flow ceased.

Lastly, in vivo animal model testing is important for determining gel conformation. Feedback from the surgeons is important to determining what changes can be made to the material, the catheter or the operational procedure. Using different catheter tips (split, bent, multiple end holes, etc.) is also important for performance.

Example Clinical Instructions for Use:

DESCRIPTION

In an embodiment, the PEGSA-PNIPAm reverse thermal gel is a sterile solution of polymer dissolved in phosphate-buffered saline (15% w/v). In an embodiment, the material is liquid at room temperature and forms a semi-solid gel upon reaching body temperature. In an embodiment, the material is intended for slow, controlled injection through a standard catheter or microcatheter. In an embodiment, the material is intended for use in embolization procedures by physicians experienced in vascular surgery.

Example Precautions:

In an embodiment, care must be taken to ensure that the polymer solution is not heated to 35° C. prior to use. If this occurs, place solution in a refrigerator (2-8° C.) until re-dissolved.

To prevent dilution and small polymer particle release into blood stream after embolization procedure, do not flush delivery catheter with water or saline prior to removal from target vessel location.

Rapid injection into the vessel may cause fragmentation or dilution of the RTG. In an embodiment, it is recommended not to exceed 1 ml/min during injection.

Example Preparation for Use:

If using this product with a microcatheter, a sheath catheter with continuous cold saline flush is recommended to keep the product cool during delivery. Connect the sheath to the microcatheter using a rotating hemostatic valve (Tuohy-Borst type adapter). Inspect all components and assemble following the recommended procedure of the rotating hemostatic valve manufacturer.

Example Instructions for Use:
1. Fill syringe with appropriate amount of polymer solution.
2. Fill second syringe (min 50 mL) with cold sterile water or saline (4° C.).
3. Prepare the patient and introduce the catheter into the vascular system according to the manufacturer's recommended guidelines.
4. Connect the syringe containing sterile water or saline to the side valve.
5. Flush and fill the microcatheter with normal saline.
6. Fill a 1 mL syringe with the desired amount of polymer solution.
7. Under angiographic guidance, inject the polymer solution into the vessel. Continuous injection of the solution is recommended to avoid gelation inside the catheter. If injection stops or becomes difficult to deliver, stop and remove the catheter. Replace with an new catheter if the procedure is incomplete. Notes: If contrast is not pre-mixed into the polymer solution, it is recommended to inject pre- and post-delivery to localize the RTG. Syringe pumps or power injectors can be used to inject polymer solution if necessary.
8. Overfill the vessel or aneurysm space by up to 50% to account for any shrinking of the material that may occur. The material will compress and conform to the target volume.
9. When delivery is complete, aspirate slightly to halt flow and detach RTG from catheter. Remove catheter from vessel.

How Supplied:

In an embodiment, the sterilized polymer saline solution is supplied in sealed glass vial. Intended for one-time use. Prior to use, shake vial gently by hand or using a vortex mixer on low speed. Avoid introduction of air bubbles that may occur from vigorous shaking. Store in 4° C. refrigerator prior to use. Avoid extended exposure to light and heat.

Conclusions:

SUMMARY

The results of this study, including characterization, analytical modeling and in vitro testing indicated that the PEGSA-PNIPAm RTG, representing example embodiments of the reverse thermal gels described herein, are a viable alternative to current liquid embolic agents on the market. A significant advantage of this material over other prospective embolics is that it can be successfully delivered through a 2 F microcatheter. Characterization tests were systematically designed to comply with FDA biocompatibility guidelines.

Animal studies may be designed to further assess the in vivo occlusion performance of the RTG. Additionally, a bench top test protocol is useful for assessing the RTG embolization potential using a segment of grafted human great saphenous vein.

Additional RTG Applications:

Application areas for certain embodiments of the reverse thermal gels described herein, in addition to repair of type II endoleaks, include treatment of cerebral AVMs, AV fistulas, venous malformations including varicose veins, nucleus pulposus restoration and cosmetic applications. Neurovascular conditions affect tens of thousands of people annually and the ability to deliver a biocompatible, aqueous-dispersed RTG through a microcatheter to brain aneurysms or AVMs would provide a substantial improvement over current materials and would potentially improve patient outcomes. Varicose vein treatment requires specialized equipment and approval for laser ablation, and as a result requires a considerable upfront investment. In addition, the tumescent solution required for ablation creates substantial discomfort for the patient. Occlusion using RTGs could prove to be a cost effective option for the physicians and may enable a more comfortable procedure for the patient. Other nonvascular applications have potential as well, such as nucleus pulposus repair via direct RTG injection through the vertebral disc space. Space-filling cosmetic applications could be of interest, as the RTG could be needle injected and would not have to be kept cool in order to traverse long distances through the vasculature.

Manufacturability and Scale-Up:

Either in-house manufacturing or partnering with a GMP-capable local biomaterial manufacturer would be a viable option for scale-up of PEGSA-PNIPAm. A larger commercial manufacturer would likely be too costly to produce the relatively limited quantities that would be needed initially. For this study, the material was successfully scaled up from less than a 2 g batch size to more than a 10 g batch size (a 10 g batch of bulk polymer yields 66.7 ml of RTG solution at the 15% concentration), with no noticeable differences in gelation temperature or physical properties, in an embodiment. Potential bottlenecks would include large organic solvent quantities required for precipitation of the polymer and downtime while dialyzing the polymer. The price point is also an important consideration and could have application dependent implications. For example, if a procedure uses only a small quantity of the RTG, selling the material on a price per gram basis could be problematic from a revenue standpoint.

REFERENCES CORRESPONDING TO EXAMPLE 1

[1] S. Vaidya, K. R. Tozer, and J. Chen, "An overview of embolic agents," Semin. Intervent. Radiol., vol. 25, no. 3, pp. 204-215, 2008.
[2] G. Cianchi, G. Zagli, and A. Peris, "Desaturation during Onyx embolization," no. December, pp. 385-386, 2008.
[3] T. G. Vrachliotis, M. E. Falagas, D. Radiology, H. D. Hospital, and R. Cross, "Infections After Endovascular Coil Embolization," pp. 805-806, 2007.
[4] H. Zhao, C. Zheng, G. Feng, Y. Zhao, H. Liang, H. Wu, G. Zhou, B. Liang, Y. Wang, and X. Xia, "Temperature-Sensitive poly(N-Isopropylacrylamide-Co-Butyl Methylacrylate) Nanogel as an Embolic Agent: Distribution, Durability of Vascular Occlusion, and Inflammatory Reactions in the Renal Artery of Rabbits," 2013.
[5] K. C. Kent, "Abdominal Aortic Aneurysms," pp. 2101-2108, 2014.
[6] A. G. Schreyer, "Transarterial Embolization of Type II Endoleaks after EVAR: The Role of Ethylene Vinyl Alcohol Copolymer (Onyx)," pp. 1288-1295, 2013.
[7] A. Poursaid, M. Martin, E. Huo, and H. Ghandehari, "Polymeric materials for embolic and chemoembolic applications," J. Control. Release, 2016.
[8] B. Pena, R. Shandas, and D. Park, "A heparin-mimicking reverse thermal gel for controlled delivery of positively charged proteins," J. Biomed. Mater. Res. Part A, vol. 103, no. 6, pp. 2102-2108, 2015.
[9] D. Park, W. Wu, and Y. Wang, "A functionalizable reverse thermal gel based on a polyurethane/PEG block copolymer," Biomaterials, vol. 32, no. 3, pp. 777-786, 2011.

[10] A. Poursaid, M. M. Jensen, E. Huo, and H. Ghandehari, "Polymeric materials for embolic and chemoembolic applications," *J. Control. Release*, 2016.

[11] F. Criado, "The EVAR Landscape in 2011," Endovasc. today, pp. 40-58, 2011.

[12] S. Aggarwal, A. Qamar, V. Sharma, and A. Sharma, "Abdominal aortic aneurysm: A comprehensive review," *Exp. Clin. Cardiol.*, vol. 16, no. 1, pp. 11-15, 2011.

[13] "Cerebral Aneurysms Fact Sheet," NINDS, 2013. [Online]. Available: http://www.ninds.nih.gov/disorders/cerebral_aneurysm/detail_cerebral_aneurysms. htm.

[14] D. Sudheendra, "Abdominal aortic aneurysm." [Online]. Available: https://www.nlm.nih.gov/medlineplus/ency/article/000162.htm.

[15] N. Sakalihasan, R. Limet, and O. D. Defawe, "Abdominal aortic aneurysm," 2005.

[16] R. L. Pande and J. A. Beckman, "Abdominal Aortic Aneurysm: Populations at Risk and How to Screen EPIDEMIOLOGY: THE SCOPE OF THE PROBLEM," 2008.

[17] S. H. Johnsen, S. H. Forsdahl, K. Singh, and B. K. Jacobsen, "Atherosclerosis in Abdominal Aortic Aneurysms: A Causal Event or a Process Running in Parallel? The Tromsø Study," 2016.

[18] C. E. Mora, C. D. Marcus, C. M. Barbe, F. B. Ecarnot, A. L. Long, F. Medicine, M. C. Merieux, and C. Bernard, "Maximum Diameter of Native Abdominal Aortic Aneurysm Measured by Angio-Computed Tomography Reproducibility and Lack of Consensus Impacts on Clinical Decisions," vol. 3, no. 2, pp. 47-55, 2015.

[19] L. L. Hench, *New Materials and Technologies for Healthcare*. 2011.

[20] B. Jackson and J. Carpenter, "Devices Used for Endovascular Aneurysm Repair: Past, Present, and Future," *Semin. Intervent. Radiol.*, vol. 26, no. 1, 2009.

[21] D. H. Knipe and F. Gaillard, "Endoleak (types)." [Online]. Available: http://radiopaedia.org/articles/endoleak-types.

[22] T. Nevala, F. Biancari, H. Manninen, P.-S. Aho, P. Matsi, K. Mäkinen, W.-D. Roth, K. Ylönen, M. Lepäntalo, and J. Perälä, "Type II endoleak after endovascular repair of abdominal aortic aneurysm: effectiveness of embolization.," *Cardiovasc. Intervent. Radiol.*, vol. 33, no. 2, pp. 278-84, 2010.

[23] M. M. MD, "Management of Endoleaks after EVAR," *American Society of Vascular Surgery*, 2013.

[24] B. Engelmann and S. Massberg, "Thrombosis as an intravascular effector of innate immunity," *Nat. Rev. Immunol.*, vol. 13, no. 1, pp. 34-45, 2013.

[25] K. Massis, W. G. Carson III, A. Rozas, V. Patel, and B. Zwiebel, "Treatment of Type II Endoleaks With Ethylene-Vinyl-Alcohol Copolymer (Onyx)," *Endovasc. Tech.*, vol. 46, no. 3, pp. 251-257, 2015.

[26] R. A. Baum, J. P. Carpenter, M. A. Golden, O. C. Velazquez, T. W. I. Clark, S. W. Stavropoulous, C. Cope, and M. Fairman, "Treatment of type 2 endoleaks after endovascular repair of abdominal aortic aneurysms: Comparison of transarterial and translumbar techniques," pp. 23-29, 2001.

[27] C. Gianturco, J. H. Anderson, and S. Wallace, "Mechanical devices for arterial occlusion," *Am. J. Roentgenol.*, vol. 28, no. 3, pp. 428-435, 1975.

[28] D. F. Kallmes and N. H. Fujiwara, "New Expandable Hydrogel-Platinum Coil Hybrid Device for Aneurysm Embolization," no. October, pp. 1580-1588, 2002.

[29] J. S. Pollak and R. I. White, "The Use of Cyanoacrylate Adhesives in Peripheral Embolization ADHESIVES IN THE UNITED," pp. 907-913, 2001.

[30] S. W. Stavropoulos, "Embolization of type 2 endoleaks after endovascular repair of abdominal aortic aneurysms with use of cyanoacrylate with or without coils," *J. Vasc. Interv. Radiol.*, vol. 16, no. 6, 2005.

[31] B. H. Lee, C. Leon, R. McLemore, J. V. Macias, and B. L. Vernon, "Synthesis and Characterization of Thermo-Sensitive Radio-Opaque Poly(N-Isopropylacrylamide-co-PEG-2-Iodobenzoate)," *J. Biomater. Sci. Polym.* Ed., vol. 22, no. 17, pp. 2357-2367, 2011.

[32] K. M. Eberhardt, M. Sadeghi-Azandaryani, S. Worlicek, T. Koeppel, M. F. Reiser, and M. Treitl, "Treatment of type I endoleaks using transcatheter embolization with onyx.," *J. Endovasc. Ther.*, vol. 21, no. 1, pp. 162-71, 2014.

[33] C. Jiang, J. Zhang, and Y. Li, "Complications Related to Percutaneous Transarterial Embolization of Intracranial Dural Arteriovenous Fistulas in 40 Patients," 2009.

[34] I. Tawil, A. P. Carlson, and C. L. Taylor, "Case Report Acute Respiratory Distress Syndrome after Onyx Embolization of Arteriovenous Malformation," vol. 2011, pp. 1-6, 2011.

[35] H. S. Engineering, A. State, and N. Sciences, "In vivo embolization of lateral wall aneurysms in canines using the liquid-to-solid gelling PPODA-QT polymer system: 6-month pilot study," vol. 119, no. July, pp. 228-238, 2013.

[36] A. Momeni, E. M. Valliant, E. P. Brennan-Pierce, J. J. S. Shankar, R. Abraham, P. Colp, and M. J. Filiaggi, "Developing an in situ forming polyphosphate coacervate as a new liquid embolic agent: From experimental design to pilot animal study," *Acta Biomater.*, vol. 32, pp. 286-297, 2016.

[37] L. Qin, L. Mei, Z. Shan, Y. Huang, X. Pan, G. Li, Y. Gu, and C. Wu, "Phytantriol based liquid crystal provide sustained release of anticancer drug as a novel embolic agent.," *Drug Dev. Ind. Pharm.*, vol. 9045, no. November, pp. 1-10, 2015.

[38] N. Koçer, H. Hanimoğlu, Ş. Batur, S. G. Kandemirli, O. Kizilkiliç, Z. Sanus, B. Öz, C. Işlak, and M. Y. Kaynar, "Preliminary experience with precipitating hydrophobic injectable liquid in brain arteriovenous malformations," *Diagnostic Interv. Radiol.*, vol. 22, no. 2, pp. 184-189, 2016.

[39] T. A. Becker and D. R. Kipke, "Flow properties of liquid calcium alginate polymer injected through medical microcatheters for endovascular embolization," *J. Biomed. Mater. Res.*, vol. 61, no. 4, pp. 533-540, 2002.

[40] T. A. Becker, M. C. Preul, W. D. Bichard, D. R. Kipke, and C. G. McDougall, "Preliminary investigation of calcium alginate gel as a biocompatible material for endovascular aneurysm embolization in vivo," *Neurosurgery*, vol. 60, no. 6, pp. 1119-1127, 2007.

[41] D. Bockler, A. Holden, M. Thompson, P. Hayes, D. Krievins, J. P. P. M. De Vries, and M. M. P. J. Reijnen, "Multicenter Nellix EndoVascular Aneurysm Sealing system experience in aneurysm sac sealing," *J. Vasc. Surg.*, vol. 62, no. 2, pp. 290-298, 2015.

[42] R. K. Avery, H. Albadawi, M. Akbari, Y. S. Zhang, M. J. Duggan, D. V Sahani, B. D. Olsen, A. Khademhosseini, and R. Oklu, "An injectable shear-thinning biomaterial for endovascular embolization," *Sci. Transl. Med.*, vol. 8, no. 365, p. 365ra156 LP-365ra156, 2016.

[43] A. K. Gaharwar, R. K. Avery, A. Assmann, A. Paul, G. H. Mckinley, A. Khademhosseini, and B. D. Olsen, "Shear-Thinning Nanocomposite Hydrogels for the Treatment of Hemorrhage," no. 10, pp. 9833-9842, 2014.

[44] B. Jeong, S. W. Kim, and Y. H. Bae, "Thermosensitive sol-gel reversible hydrogels," *Adv. Drug Deliv. Rev.*, vol. 64, no. SUPPL., pp. 154-162, 2012.

[45] Y. Zhang, S. Furyk, D. E. Bergbreiter, and P. S. Cremer, "Specific ion effects on the water solubility of macromolecules: PNIPAM and the Hofmeister series," *J. Am. Chem. Soc.*, vol. 127, no. 41, pp. 14505-14510, 2005.

[46] X. Zhang, D. Wu, and C. C. Chu, "Synthesis and characterization of partially biodegradable, temperature and pH sensitive Dex-MA/PNIPAAm hydrogels," *Biomaterials*, vol. 25, no. 19, pp. 4719-4730, 2004.

[47] M. Ogura, H. Tokuda, S. Imabayashi, and M. Watanabe, "Preparation and Solution Behavior of a Thermoresponsive Diblock Copolymer of Poly (ethyl glycidyl ether) and Poly (ethylene oxide)," *Work*, no. 30, pp. 9429-9434, 2007.

[48] K. N. Plunkett, X. Zhu, J. S. Moore, and D. E. Leckband, "PNIPAM chain collapse depends on the molecular weight and grafting density," *Langmuir*, vol. 22, no. 9, pp. 4259-4266, 2006.

[49] D. S. Lee, M. S. Shim, S. W. Kim, H. Lee, I. Park, and T. Chang, "Novel Thermoreversible Gelation of Biodegradable PLGA-block-PEO-block-PLGA Triblock Copolymers in Aqueous Solution," no. CI, pp. 587-592, 2001.

[50] H. J. Oh, M. K. Joo, Y. S. Sohn, and B. Jeong, "Secondary Structure Effect of Polypeptide on Reverse Thermal Gelation and Degradation of L/DL-Poly (alanine)-Poloxamer-L/DL-Poly (alanine) Copolymers," pp. 8204-8209, 2008.

[51] Q. Peng, X. Sun, T. Gong, C. Y. Wu, T. Zhang, J. Tan, and Z. R. Zhang, "Injectable and biodegradable thermosensitive hydrogels loaded with PHBHHx nanoparticles for the sustained and controlled release of insulin," *Acta Biomater.*, vol. 9, no. 2, pp. 5063-5069, 2013.

[52] B. Vernon and A. Martinez, "Gel strength and solution viscosity of temperature-sensitive, in-situ-gelling polymers for endovascular embolization," *J. Biomater. Sci. Polym. Ed.*, vol. 16, no. 9, pp. 1153-1166, 2005.

[53] "Use of International Standard ISO 10993-1, 'Biological evaluation of medical devices—Part 1: Evaluation and testing within a risk management process' Guidance for Industry and Food and," 2016.

[54] R. A. Shenoi, B. F. L. Lai, M. Imran Ul-Haq, D. E. Brooks, and J. N. Kizhakkedathu, "Biodegradable polyglycerols with randomly distributed ketal groups as multi-functional drug delivery systems," *Biomaterials*, vol. 34, no. 25, pp. 6068-6081, 2013.

[55] M. Constantin, M. Cristea, P. Ascenzi, and G. Fundueanu, "Lower critical solution temperature versus volume phase transition temperature in thermoresponsive drug delivery systems," *Express Polym. Lett.*, vol. 5, no. 10, pp. 839-848, 2011.

[56] F. Kreith, R. M. Manglik, and M. S. Bohn, *Principles of heat transfer*. Cengage learning, 2012.

[57] Q. Nguyen and N. Nguyen, "Incompressible Non-Newtonian Fluid Flows."

[58] B. Al-Shammari, T. Al-Fariss, F. Al-Sewailm, and R. Elleithy, "The effect of polymer concentration and temperature on the rheological behavior of metallocene linear low density polyethylene (mLLDPE) solutions," *J. King Saud Univ.—Eng. Sci.*, vol. 23, no. 1, pp. 9-14, 2011.

[59] C. Schatz, C. Pichot, T. Delair, C. Viton, and A. Domard, "Static light scattering studies on chitosan solutions: From macromolecular chains to colloidal dispersions," *Langmuir*, vol. 19, no. 23, pp. 9896-9903, 2003.

[60] U. Nobbmann, M. Connah, B. Fish, P. Varley, C. Gee, S. Mulot, J. Chen, L. Zhou, Y. Lu, F. Shen, J. Yi, and S. E. Harding, "Dynamic light scattering as a relative tool for assessing the molecular integrity and stability of monoclonal antibodies.," *Biotechnol. Genet. Eng. Rev.*, vol. 24, no. April 2015, pp. 117-128, 2007.

[61] S. Zhou, S. Fan, S. C. F. Au-yeung, and C. Wu, "Light-scattering studies of poly(N-isopropylacrylamide) in tetrahydrofuran and aqueous solution," *Polymer (Guildf).*, vol. 36, no. 7, pp. 1341-1346, 1995.

[62] M. Nawaz, M. K. Baloch, and W. Rehman, "Investigating the compatibility of polymers in common solvent," *J. Chil. Chem. Soc.*, vol. 55, no. 1, pp. 90-93, 2010.

[63] I. Teraoka, *Polymer Solutions: An introduction to physical properties*, vol. 3. 2002.

[64] Y. Shachaf, M. Gonen-Wadmany, and D. Seliktar, "The biocompatibility of Pluronic F127 fibrinogen-based hydrogels," *Biomaterials*, vol. 31, no. 10, pp. 2836-2847, 2010.

[65] S. Lyu and D. Untereker, "Degradability of Polymers for Implantable Biomedical Devices," pp. 4033-4065, 2009.

Figure 4:
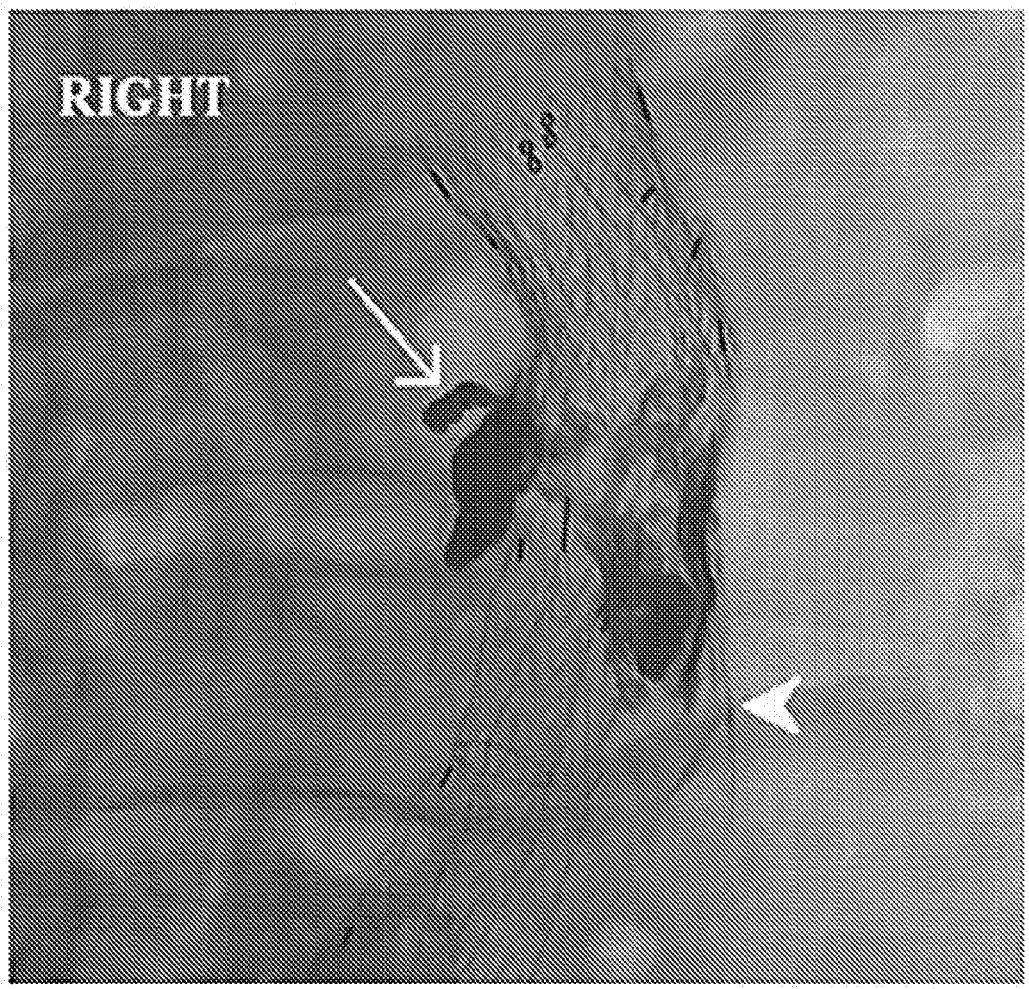
FIG. 4. Digital radiograph showing Onyx embolization of a type II endoleak. Image courtesy of Massis, et al. [25].

[66] "Human Performance Capabilities." [Online]. Available: https://msis.jsc.nasa.gov/sections/section04.htm#FIG. 4.9.3-4.

[67] J. Simon and H. Thompson, "Hydrophilic Coatings: Considerations for Product Development," *Surf. Treat. Coatings*, 2011.

[68] Y. Zhao, C. Zheng, Q. Wang, J. Fang, G. Zhou, and H. Zhao, "Permanent and Peripheral Embolization: Temperature-Sensitive p (N-Isopropylacrylamide-co-butyl Methylacrylate) Nanogel as a Novel Blood-Vessel-Embolic Material in the Interventional Therapy of Liver Tumors," pp. 2035-2042, 2011.

[69] M. A. Schubert, M. J. Wiggins, J. M. Anderson, and A. Hiltner, "Role of oxygen in biodegradation of poly (etherurethane urea) elastomers," vol. 34, no. 2, pp. 519-530, 1997.

[70] M. A. Schubert, M. J. Wiggins, M. P. Schaefeq, A. Hiltner, and J. M. Anderson, "Oxidative biodegradation mechanisms of biaxially strained poly (etherurethane urea) elastomers," vol. 29, pp. 337-347, 1995.

[71] E. M. Christenson, J. M. Anderson, and A. Hiltner, "Oxidative mechanisms of poly(carbonate urethane) and poly(ether urethane) biodegradation: in vivo and in vitro correlations.," *J. Biomed. Mater. Res. A*, vol. 70, no. 2, pp. 245-55, 2004.

Example 2: PEGSA-PNIPAm Synthesis Protocol

Materials:

| ACRONYM | FULL NAME | MW (G/MOL) |
| --- | --- | --- |
| ACVA | 4,4'-Azobis(4-cyanovaleric acid) | — |
| DCC | Dicyclohexylcarbodiimide | 206.33 |
| DCM | Dichloromethane | — |
| DMAP | 4-(Dimethylamino)pyridine | 122.17 |
| DMF | Dimethylformamide | — |
| NIPAM | N-isopropylacrylamide | 113.16 |
| PEGDGE | poly(ethylene glycol) diglycidyl ether) | 526 |
| PEGSA | Poly(ethylene glycol) succinic acid | 618 |
| PNIPAM | Poly(n-isopropylacrylamide) | 10000 |
| SA | Succinic acid | 118.09 |
| THF | Tetrahydrofuran | — |
| TPP | triphenylphosphine | 262 |

PEGSA synthesis, in an embodiment:

The following calculations are based on 2 g of PEGDGE monomer. Use a 1.2 molar excess of SA and 10 mol % TPP catalyst.

$$2 \text{ g} * \frac{1 \text{ mol PEGDGE}}{526 \text{ g}} * \frac{1.2 \text{ mol } SA}{1 \text{ mol PEGDGE}} * \frac{118.09 \text{ g}}{1 \text{ mol } SA} = 0.54 \text{ g } SA$$

$$2 \text{ g} * \frac{1 \text{ mol PEGDGE}}{526 \text{ g}} * \frac{0.1 \text{ mol } TPP}{1 \text{ mol PEGDGE}} * \frac{262 \text{ g}}{1 \text{ mol } TPP} = 0.10 \text{ g } TPP$$

1. Set a hot plate with oil bath to 120° C. and 150 RPM stir speed.
2. In a clean, dry 100 ml round bottom flask add a 1"×⅜" stir bar. Then add the PEGDGE, purge with nitrogen and cap with a rubber septum stopper.
3. Weigh out the SA using a weigh boat or weighing paper and add to the flask. Purge with nitrogen.
4. Weigh out the TPP using a weigh boat or weighing paper and add to the flask. Purge with nitrogen.
5. Add the flask to the oil bath and react for 24 hours under nitrogen (using manifold or nitrogen balloon attached to an 18 G needle through the septum stopper).
6. Reduce stirring speed to 70 RPM and react for additional 24 hours.
7. After 48 total hours, remove flask from hot plate and let cool.
8. After the flask has cooled, add approximately 10 ml DCM to dissolve the PEGSA (add more DCM if the material does not readily dissolve within 5 min).
9. In a 250 ml Erlenmeyer flask add 100 ml diethyl ether (10x relative to DCM amount). Place on a stir plate. Remove the stir bar from the PEGSA round bottom flask and add it to the Erlenmeyer.
10. Precipitate the PEGSA solution dropwise into the ether flask, while stirring. The PEGSA will precipitate out of solution and collect on the bottom of the flask, while any unreacted PEGDGE and TPP will remain in solution. SA is not soluble in ether, but will be removed later during dialysis.
11. Pour off the supernatant and repeat the precipitation twice more.
12. After the final precipitation, pour off the supernatant and re-dissolve the PEGSA in 5-10 ml DCM.
13. Record the empty weight of a scintillation vial, then add the PEGSA solution.
14. Rotovap to remove the DCM. Start by pulling low vacuum until the solution starts to bubble, then gradually increase the vacuum as necessary until little to no bubbles are present. Use dry ice or a mixture of ice and ethanol in the rotovap trap.
15. Cover the vial in foil and store in a cool dry area.

PNIPAm synthesis, in an embodiment

The following protocol is for a 5 g batch of PNIPAm
1. Set a hot plate with oil bath to 70° C. and 200 RPM stir speed.
2. In a clean, dry 250 ml round bottom flask add a 1"×⅜" stir bar.
3. Using a weigh boat, measure out 5 g NIPAm, and add to flask.
4. Add 15 ml DMF to the flask. This is a 3:1 solvent to monomer ratio. This amount can be adjusted up or down to obtain higher or lower molecular weight PNIPAm.
5. Stir mixture on stir plate until NIPAm is dissolved.
6. Weigh out 50 mg of ACVA (1 wt % relative to NIPAm) and add to flask. This component is the thermal initiator and also adds carboxylic acid functionality to the PNIPAm.
7. Cap with a rubber septum stopper and bubble with nitrogen for 20-30 min. Use a nitrogen balloon attached to a needle long enough to extend into the solution. Add a second needle in the septum stopper to vent. Bubble slowly by gradually releasing pressure on the neck of the balloon. The balloon will have to be refilled multiple times during this process.
8. Add the flask to the oil bath and react for 3 hours under nitrogen (using manifold or nitrogen balloon attached to an 18 G needle through the septum stopper). Running the reaction for a longer time will increase the molecular weight of the PNIPAm.
9. After 3 hours, remove the reaction from the heat and let cool.
10. Heat 600 ml milli-Q water to 60° C.
11. Add 200 ml milli-Q water (10x relative to DMF amount) directly to PNIPAm flask to precipitate while stirring. Let stir for 2-3 min then pour off supernatant.
12. Pour off the supernatant and repeat the precipitation twice more.
13. After the final precipitation, pour off the supernatant and add approximately 100 ml cool milli-Q water to the flask and place in the refrigerator overnight until the PNIPAm is fully dissolved. Stir occasionally to help speed up the process.
14. Once the PNIPAm is dissolved, add the solution to 12-14 kDa MWCO dialysis tubing.
15. Place the filled dialysis tubing in a beaker with approximately 1000 ml milli-Q water, stirring at 60 RPM for two days, changing the water in the beaker after one day.
16. After two days of dialysis, transfer the solution in the tubing to a beaker and divide evenly into 50 ml conical tubes. Record the empty weight of the tubes prior to adding the solution. Do not exceed 35 ml in each tube, or the tubes may crack in the freezer.
17. Place the tubes in a −80° C. for several hours until completely frozen.
18. Once frozen, place the tubes in the lyophilizer to dry the polymer. Record the final weight of the tubes and calculate the total amount of polymer synthesized.

PEGSA-PNIPAm conjugation, in an embodiment:

Activation of PNIPAm: The following calculations are for a 25% PNIPAm conjugation to PEGSA, and assuming a 0.5 g starting amount of PEGSA and a PNIPAm molecular weight of 10,000 g/mol.

$$0.5 \text{ g } PEGSA * \frac{1 \text{ mol } PEGSA}{618 \text{ g}} * \frac{2 \text{ mol OH groups}}{1 \text{ mol } PEGSA} *$$
$$0.25 \text{ conjugation} * \frac{10000 \text{ g}}{1 \text{ mol } PNIPAm} = 4.05 \text{ g } PNIPAm$$

$$0.5 \text{ g } PEGSA * \frac{1 \text{ mol } PEGSA}{618 \text{ g}} * \frac{2 \text{ mol OH groups}}{1 \text{ mol } PEGSA} *$$
$$0.25 \text{ conjugation} * \frac{206.33 \text{ g}}{1 \text{ mol } DCC} = 0.0835 \text{ g } DCC$$

$$0.5 \text{ g } PEGSA * \frac{1 \text{ mol } PEGSA}{618 \text{ g}} * \frac{2 \text{ mol OH groups}}{1 \text{ mol } PEGSA} *$$
$$0.25 \text{ conjugation} * \frac{122.17 \text{ g}}{1 \text{ mol } DMAP} = 0.0492 \text{ g } DMAP$$

1. Set a hot plate with oil bath to 55° C. and 200 RPM stir speed.
2. In a clean, dry 250 ml round bottom flask add a 1"×⅜" stir bar.
3. Weigh out PNIPAm and add directly to round bottom flask. PNIPAm is very light and sticks to everything, so carefully do this in the fume hood and use forceps to add the PNIPAm to the flask. A funnel may also be helpful.
4. Add 15-30 ml THF, cap flask with septum stopper and stir until PNIPAm is completely dissolved. Add more THF if necessary.
5. In the fume hood, weigh out DCC using a small weighing boat. Add to round bottom flask.
6. In the fume hood, weigh out DMAP using a small weighing boat. Add to round bottom flask.
7. Add the flask to the oil bath and react for 24 hours under nitrogen (using manifold or nitrogen balloon attached to an 18 G needle through the septum stopper).

Addition of PEGSA to activated PNIPAm, in an embodiment:
1. In a scintillation vial, weigh out PEGSA (0.5 g).
2. Add approximately 5 ml THF along with a small stir bar and place on stir plate until dissolved.
3. Using a needle and syringe, add the PEGSA solution to the activated PNIPAm solution dropwise, adding about 1 ml every 5-10 min.
4. Continue to react the PEGSA-PNIPAm solution on heat for an additional 24 hours (55° C. and 200 RPM).
5. Remove from heat and let the solution cool.
6. In a 500 ml round-bottom flask, add approximately 300 ml ether.
7. Transfer the cooled PEGSA-PNIPAm solution to a separatory funnel and precipitate dropwise into the ether, while stirring. Let this sit for about 30 min after precipitating.
8. Pour off the supernatant. Then place the flask on the rotovap to remove the remainder of the ether and THF. Use dry ice or a mixture of ice and ethanol in the rotovap trap.
9. Dissolve the PEGSA-PNIPAm polymer in 50 ml milli-Q water and place in the refrigerator overnight or until dissolved, stirring occasionally. The solution may have a cloudy appearance, but all of the solid precipitate should be completely dispersed.
10. Once the material is dissolved, add the solution to 12-14 kDa MWCO dialysis tubing.
11. Place the filled dialysis tubing in a beaker with approximately 1000 ml milli-Q water. The solution in the tubing may initially turn a milky white, but this will disappear with time. Continue stirring at 60 RPM for two days, changing the water in the beaker after one day.
12. After two days of dialysis, transfer the solution in the tubing to a beaker and divide evenly into 50 ml conical tubes. Record the empty weight of the tubes prior to adding the solution. Do not exceed 35 ml in each tube, or the tubes may crack in the freezer.
13. Place the tubes in a −80° C. for several hours until completely frozen.
14. Once frozen, place the tubes in the lyophilizer to dry the polymer. Record the final weight of the tubes and calculate the total amount of polymer synthesized.
15. At this point, the PEGSA-PNIPAm is ready to use. Disperse the dry polymer in milli-Q water or PBS at the desired concentration. If filtration is required, dissolve the dry polymer in excess water (enough so that viscosity will not be an issue when going through the filter). In the biosafety hood, using a vacuum filtration setup with a 0.2 μm pore size, filter the entirety of the solution and transfer to sterile 50 ml conical tubes. Repeat steps 13 and 14 to re-dry the polymer.

Example 3: Oxidative and Hydrolytic Degradation Protocol

Scope:
This testing protocol, in an embodiment, provides a standard method for accelerated evaluation of the oxidative and hydrolytic stability of polymer materials intended for implantation into the body. The materials being evaluated are placed in various solutions under elevated temperature. Samples are pulled from the solutions at set time points and the physical and chemical properties are measured. For each sample, mass is measured, and FTIR is used to evaluate any chemical changes. Results from this method are used as a tool to evaluate the long term stability of polymeric implants. Data from these tests are relevant and appropriate for use in engineering design.

Equipment:
The following equipment is required for this method:
Precision balance (0.0001 g precision); FTIR; Lyophilizer; Shaking incubator; Glass screw cap vials Materials
20% hydrogen peroxide ($H_2O_2$) in 0.1 M cobalt chloride ($CoCl_2$) solutions in air tight containers will be used to mimic in-vivo environment. Note: mix $H_2O_2$ and $CoCl_2$ in hood as the mixture will create fumes and generate heat. Acidic, orange colored solution, turns blue/purple when dry (will be able to see if there is still some in dried polymer).
Milli-Q water will be used to study hydrolytic degradation of the polymer.
Hydrogen peroxide solution, 30 wt. % in $H_2O$, ACS reagent (Aldrich)
Cobalt(II) chloride, 97% (Aldrich)
Milli-Q water
RTG (15% polymer in water)

Test Specimens:
1 mL samples of 15% RTG solution will be added to 15 mL glass scintillation vials and gelled prior to testing.

Procedure:
Preliminary Tests
1. Weigh empty 15 mL conical tube on a precision balance and record the value to the nearest 0.0001 g.
2. Tare the balance and add 0.15 g of dry polymer and record value to the nearest 0.0001 g.
3. Add 850 uL of milli-Q water to the vial using a micropipette (amount required to make 15% polymer solution). Mix until dissolved.
Note: RTG solution should contain water and not PBS so that when lyophilized, salts are not left behind which would add to the weight of the polymer.
4. Freeze and lyophilize to remove water.
5. Measure weight of the tube after lyophilization and record the value to the nearest 0.0001 g. Subtract from original tube weight. Compare this value to the amount of dry polymer added in step 2.
6. Repeat steps 1-5 for 3 RTG samples.

Hydrolytic and Oxidative Degradation
1. Prepare 30 mL 15% RTG solution. Use the provided spreadsheet to record actual weight of PEGSA-PNIPAm and milliQ water added. Refrigerate and stir intermittently on vortex until PEGSA-PNIPAm is dissolved.
2. Place empty scintillation vial on precision balance and tare.

3. Add approximately 1 g of RTG solution using a Pasteur pipette and record value to the nearest 0.0001 g.
4. Repeat steps 2-3 for all specimens.
5. Place all specimens in 37° C. shaking incubator for 5-10 min, or until complete gel formation is observed (no shaking).
6. Add 10 mL of pre-warmed (37° C.) 20% hydrogen peroxide in 0.1M cobalt chloride solution ($H_2O_2/CoCl_2$, oxidative group), or pre-warmed (37° C.) milli-Q water (hydrolytic group) to each of the vials and return to shaking incubator (shaking on at 60 RPM). The specimens are maintained at isothermal conditions until removed for evaluation.
a. Note: for the vials containing $H_2O_2/CoCl_2$, cap with clear plastic cap with hole in top to prevent pressure buildup.
b. Note: The $H_2O_2/CoCl_2$ system has demonstrated utility for an accelerated test that reproduces the in vivo oxidation of polymers for evaluating long term biostability [69]-[71].
7. At each time point, 3 vials from each test group containing specimens to be evaluated are removed from the incubator (e.g. 3 RTG in $H_2O_2/CoCl_2$, 3 RTG in milli-Q water).
8. For each of the specimen vials, carefully pour or pipette off the liquid solution from each vial, leaving only the gelled polymer.
9. Add 10 mL of pre-warmed milli-Q water (37° C.) to each vial to wash the polymer and remove any salts left behind by the $H_2O_2/CoCl_2$ solution. Let each specimen soak for 5-10 min. Repeat the wash 3 times for each specimen.
10. After the last wash is complete, cap the vials and place in −80° C. freezer for at least 2 hours.
11. Once frozen, lyophilize to remove any remaining water (at least 24 hours).
12. Measure weight of the vial after lyophilization and record the value to the nearest 0.0001 g. Subtract from original vial weight. Compare this value to the initial amount of dry polymer added based on a 15% mixture.
13. Mass loss (3 per group per time point) is determined using the equation: $W_1/W_0*100\%$, where $W_0$ is the initial RTG weight and $W_1$ is the remaining RTG weight.
14. For FTIR analysis (1 per group per time point), re-dissolve dry RTG in approx. 1 mL of THF and take mid-IR spectra using KBr salt plates. Save spectra and look for evidence of chemical changes indicative of degradation.
15. Repeat steps for 7-14 for each time point.

Example 4: Live/Dead Cell Viability Protocol

Passage and plate cells (HUVECs):
1. Grow cells in T75 flask.
2. Once confluent, passage into new T75 and 12-well plate:
a. Remove old media
b. PBS wash (10 mL)
c. Add trypsin (1.5 mL), incubate 10 min
d. Add 8-10 mL fresh media
e. Transfer 2.5 mL cell media from original T75 to new T75, add 7.5 mL fresh media, incubate
f. Add 500 uL cell media from original T75 to each well, add additional 500 uL fresh media, incubate 24 hrs
3. From 12 well plate (after 24 hr incubation):
a. Remove old media
b. PBS wash (500 uL) each well
c. Add new media according to groups (if cells are close to confluent):
Groups (using 12 well plate):
Neg. control: 2 wells, full media (1000 ul)
Pos. control: 2 wells, media+10% EtOH (agitated cells) (900 ul+100 ul EtOH)
Neg Control: 2 wells media+PBS (500+500 ul) (if necessary)
Experimental: Remaining wells
d. Incubate 24 hrs
e. Run live/dead
  Live/dead protocol:
1. In 12 well plate: remove old media, 500 uL PBS wash each well
2. Add 3.87 mL PBS into component A (Use a plastic vial with a lid)
3. Put 290 uL of solution into each well
4. Incubate 25 minutes
5. Add 130 uL PBS into component B
6. Put 10 microliters of solution into each well and let sit on bench for 5-10 minutes
7. Image using fluorescent microscope (at least 3 images per well; randomize order, or go well 1-12, 12-1, 1-12, etc.)
  Imaging Protocol
1. Open Zeiss software
2. Turn on microscope (left side)
3. Turn on lamp (black unit in back of microscope) and let warmup
4. In software, go to acquisition tab, choose Bioengineering default
5. Turn off DAPI channel
6. Choose the magnification level (5, 10 or 20x works best)
7. Turn the dial to GFP (on microscope, near focusing knob)
8. Select EGFP channel
9. Click on "Live"
10. Turn on light (lever on left side)
11. Focus image
12. Click "Set Exposure" for GFP, or adjust manually
13. Click mRFP1.2
14. Turn dial to mRFP
15. Set exposure or adjust manually
16. Click "Snap" and follow onscreen instructions
17. Repeat process for all wells.

APPENDIX 1

Comparison of Upcoming Liquid Embolics

| Material | Type | Advantages | Disadvantages | Polymerization Safety Profile |
|---|---|---|---|---|
| PEGSA-PNIPAm | Reverse thermal gel | Biocompatible Aqueous solution No shaking/mixing Required prior to injection, in an embodiment Radiopaque and/or biomolecule conjugation | If gelation occurs prior to distal tip of catheter, delivery/extrusion is difficult, in an embodiment | Pre-polymerized material No free monomer or small molecules are introduced to the vessel, in an embodiment Additional toxicity testing beneficial |

APPENDIX 1-continued

Comparison of Upcoming Liquid Embolics

| Material | Type | Advantages | Disadvantages | Polymerization Safety Profile |
|---|---|---|---|---|
| N-butyl cyanoacrylate (NBCA) | In-situ | Injectable Rapid polymerization | Can be brittle Catheter entrapment Unpredictable flow Rapid polymerization | FDA approved Polymerization releases formaldehyde Can cause vessel wall inflammation/granulomas Is full conversion achieved? |
| Sapheon Venaseal | In situ (NBCA) | Additives used to slow polymerization Low cytotoxicity PMA approved by FDA in 2015 | Proprietary formulation Varicose vein treatment | See NBCA From FDA: Product should not be used in patients with hypersensitivity to adhesive, blood clots, acute whole-body infection |
| PPODA-QT | In situ | Non-degradable Non-adhesive | Toxicity of initiating solution 10 min polymerization | High pH initiating system can be cytotoxic, but pre-mixing can reduce toxicity Conversion percentage, safety of starting monomers needs further study |
| Coacervates | In situ | Divalent cations provide radiopacity and initiate polymerization Low cytotoxicity Vessel occlusion achieved in animal model | Dual lumen catheter required for entire catheter length - not optimal for small vessels Gel was not cohesive during injection | Starting polyphosphate material is pre-synthesized Toxicity of soluble Ba needs to be addressed through long-term degradation study Will embolic migrate due to non-cohesiveness? Small molecule release |
| Liquid crystal - Phytantriol | In situ | 30 days sustained in vitro drug release Injectable through 0.035" ID catheter | 40 s gelation time Non-aqueous solvents required (DMSO or NMP) | Liquid crystal precursor is used along with solvent - could be an issue with longer gelation time How to confirm full conversion? |
| Onyx | Precipitation polymerization | Non-adhesive Complete occlusion More controlled flow vs. NBCA | DMSO toxicity DMSO compatible catheter needed Reflux High cost Can adhere to catheter Mixing of contrast agent required | FDA approval Pre-polymerized "Outside-in" solidification as DMSO is resorbed |
| PHIL | Precipitation polymerization | Non-adhesive Contrast attached to polymer Less reflux, faster polymerization, less CT artifacts vs Onyx | DMSO toxicity More brittle, more vascular inflammation vs Onyx | Polymerization time similar to Onyx Long-term safety studies are needed |
| Calcium alginate | Precipitation polymerization | Biocompatible Non-adhesive Water soluble | Aneurysm recurrence rates are unknown Efflux from aneurysm cavity | Fast polymerization, immediate and stable gel formation Starting materials and gel are non-cytotoxic, alginate does not react with natural calcium in blood |
| Eudragit | Precipitation polymerization | Low viscosity No catheter adhesion | Slow injection required Ethanol dispersing solvent Vascular inflammation | Copolymer has been used in pill coatings - degradation products are safe Concern for high EtOH concentrations in blood if injected too rapidly |

APPENDIX 1-continued

Comparison of Upcoming Liquid Embolics

| Material | Type | Advantages | Disadvantages | Polymerization Safety Profile |
|---|---|---|---|---|
| PNIPAm-co-butyl methacrylate nanogel | Temperature sensitive hydrogel | Injectable through 2.7 F catheter No recanalization No catheter adhesion Biocompatible | Mild inflammatory response Precise injection rate required | Pre-polymerized material If injected too rapidly, gel will not form until further downstream Non-degradable Need to determine source of inflammatory response |
| PNIPAm-co-acrylic acid | Temperature sensitive hydrogel | Injectable through 0.03" catheter Lower MW polymer solutions were less viscous | Did not test cytotoxicity No animal model testing | Proof of concept study Safety profile of material needs to be developed |
| PNIPAm-co-PEG acrylate | Temperature sensitive hydrogel | Physical and chemical gelation possible Favorable biocompatibility | Chemically similar to our RTG Low transition temperature (27-28° C.) | Chemical gelation process needs more study - how much residual thiol compound is left after chemical gelation? Better cytotoxicity tests needed |
| PNIPAm-co-PEG-iodobenzoate | Temperature sensitive hydrogel | Covalently attached radio-opaque component In vitro biocompalibility | Chemically similar to our RTG Higher radio-opaque concentration reduces gel transition temperature No indication of viscosity | Pre-polymerized material Any long-term degradation products? |
| PNIPAm-co-DBA-co acrylic acid | Temperature sensitive hydrogel | Complete degradation after 20 days Low cytotoxicity of gel and degradation products | No mention of viscosity or handling properties If material degrades, does recanalization occur? | Pre-polymerized material No adjacent tissue damage observed after complete degradation |

Example 5: Reverse Thermal Gel Embolization of Human Saphenous Vein In-Vitro

OBJECTIVE: Test Reverse Thermal Gel (RTG) occlusion of human saphenous vein (SV) under simulated body conditions ex-vivo.

ABSTRACT: A 15 wt % solution of RTG in Phosphate Buffered Saline was perfused into a SV within environmental conditions made to simulate conditions within the human body. An explanted human saphenous vein was immersed in a circulating water bath held at 37° C. The Vein was mounted on a custom adjustable rig, as described below. 5Fr and 1.8Fr catheters were used to deploy the RTG material into the SV lumen and the procedure was recorded both inside and outside the vessel using a borescope and camera. The RTG solution was shown to effectively deploy within the vessel and occlude the vessel under physiological venous pressure.

Materials:
Artery:

Human SV was dissected into a short, straight segment, approximately 3 inches in length. The vein was tied the test rig cannula using silk thread and the rig was adjusted to straighten the vein segment.

Figure 39:
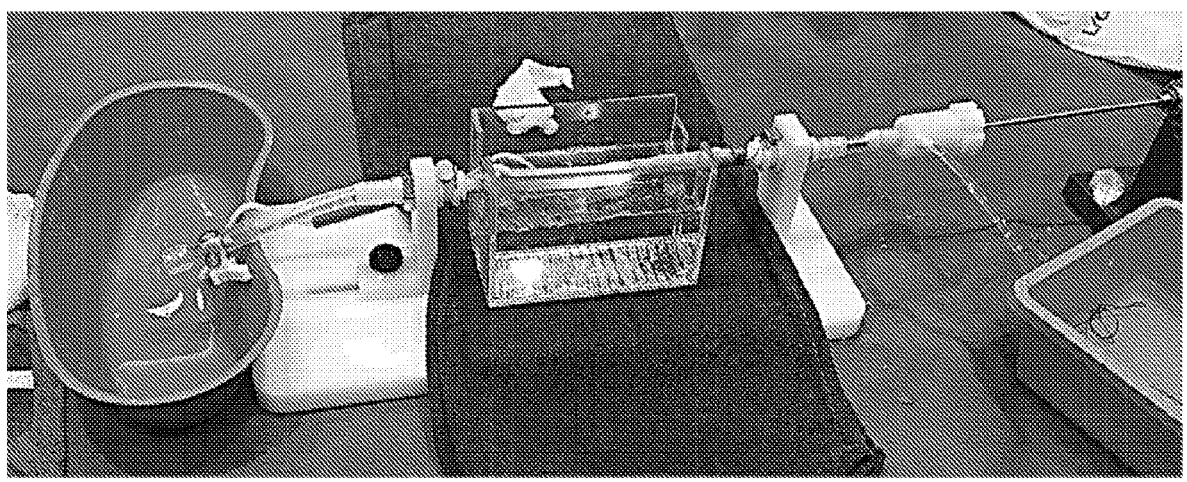
FIG. 39. Photograph of a medical artery test setup.

Test Rig:

A custom artery holder and imaging system was used during this experiment, FIG. 39. The test rig allows for mounting vein or artery segments onto cannula and adjusting the distance between the cannula to straighten and/or strain the mounted vessel. The rig also allows for mounting a borescope into the vessel lumen and attaching various tubing and adapters to provide plumbing to the vessel lumen.

Water Bath:

A water bath was used to maintain the water environment, surrounding the mounted tissue and test rig, at 37° C. This was achieved using an immersion heater accurate to within ±0.1° C., FIG. 40.

Pressure System:

In-vivo venous pressures were maintained during the experiment by suspending a fluid reservoir with a lab clamp. The reservoir was plumbed to the SV lumen using ⅛"-ID vinyl tubing. The vinyl tubing ~2 ft in length, was submerged within the heated water bath to warm the water to body temperature before it reached the SV. Pressure head was not measured at the vessel, but rather was imparted by vertical distance between the elevated reservoir and the vessel midline, 4-5 inches $H_2O$. Pressure loss due to flow within the tubing was neglected.

Imaging:

A flexible borescope was inserted into the SV lumen at the distal end of the test rig. The borescope diameter was small enough to allow for water to flow through the annular space between the scope and the vessel lumen. This allowed for continuous flow of warm "blood" during RTG deployment, if required.

Figure 40:
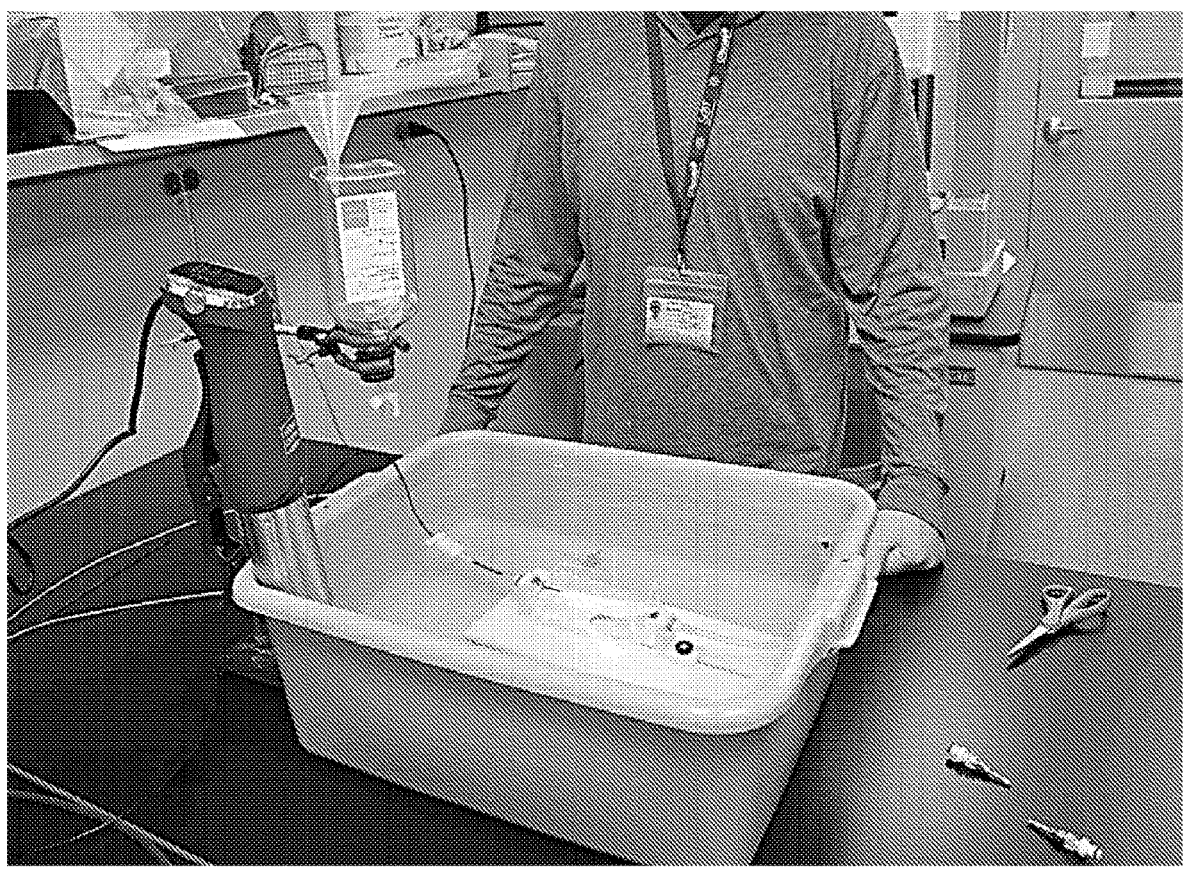
FIG. 40. Photograph of an assembled testing system.

Experimental Setup:

The experimental setup is shown in FIG. 40. Here, the immersion heater is shown in the front left corner. The pressure reservoir is shown at the left, behind the heater. The artery and test rig is submerged within the water bath. The hemostasis valve, used to insert the venous cannula and inject cold saline can be seen at the right hand side of the water bath near the bin handle. The cannula used to attach the SV to the rig are shown on the table to the right of the water bath. The borescope is the black wire shown passing from the test rig to the left side of the water bath.

Reverse Thermal Gel:

The RTG used during this experiment was of the standard chemical composition and was dissolved in Phosphate Buffered Saline at a weight/volume concentration of 15%. The RTG solution was prepared the day before the experiment to allow the RTG to fully dissolve and for the solution to be refrigerated at 4° C. overnight. RTG solution was stored in an ice water bath before use.

Experimental Procedure/Results:

Human SV was mounted to the test rig as described above in the material section. The test rig was submerged in the water bath at 37° C. The borescope was plumbed to the outlet, distal, end of the mounted vessel through a Y-connection to allow video capture in tandem with "blood" flow provided by the pressure reservoir. The upstream, proximal, end of the SV was plumbed to a T-connection that was attached to the pressure reservoir to provide "blood" flow. The straightaway of the T-connection was plumbed to a hemostasis valve which allowed for an intravenous catheter (5-french) to be placed within vessel lumen. The hemostasis valve allowed for flushing the catheter and vessel lumen with cold saline prior to RTG deployment, or clearing RTG from the catheter using cold saline after deployment. RTG was deployed by hand, through the catheter, using a 3 mL or 1 mL syringe.

The procedure for RTG embolization followed a separate protocol depending if the RTG was to be deployed from the catheter terminus as a gel "noodle" or as a un-gelled liquid. RTG behavior is documented in a video taken by the borescope within the vessel lumen.

For the liquid gel plug, the 5-french catheter was pre-cooled using a large volume of cold saline (~10 mL, held in ice bath prior to use), followed immediately by cold RTG (held in ice bath prior to use). The "blood" flow provided by the pressure reservoir was interrupted during deployment so that the liquid gel was not washed out of the vessel. The bolus of cold saline was sufficient to cool the vessel lumen to the point that the RTG exited the catheter in a liquid state. RTG filled the vessel lumen and gelled when deployment was stopped, creating a plug within the vessel that could not be dislodged by the pressure head provided by the "blood", 1:05 in Viemo video linked above. A subsequent RTG plug was shown to be dislodged and potentially removed by a cold saline flush after RTG plug was gelled within the vessel lumen, 5:10 in video. Dissection of the vessel and inspection of the RTG plug is shown at 9:30 in the video. The RTG plug fully occluded the vessel and had the consistency of a pencil eraser upon inspection. However, as the RTG was allowed to cool to room temperature, the plug eventually returned to the liquid state.

For the gel noodle deployed using a 5-french catheter, a small volume of cold saline (~2 mL, held in ice bath prior to use) was injected to pre-cool the catheter, followed immediately by cold RTG (held in ice bath prior to use). For the gel noodle deployed using a 1.9-french catheter, the smaller was threaded through a larger 5-french catheter that could be cooled using cold saline injected within the annular space between the two catheters, 2 min-10 s time point in Viemo video. The bolus of cold saline was not of a large enough volume to cool the vein lumen and the "blood" flow was maintained so that the vessel was warm during RTG deployment. This resulted in the RTG being extruded from the catheter tip as a gelled noodle which space filled the vessel lumen. This gel noodle would pile up on itself and form a plug, thus occluding the vessel. Initial deployment of RTG resulted in a thin noodle which readily piled up on itself within the vessel lumen, 2:21 in Viemo video. After a short time, RTG deployment was paused to allow the RTG to warm up within the catheter, and then deployment was continued. This resulted in a much larger diameter gel noodle which did not pile up on itself within the vessel lumen, 2:34 in Viemo video. Further pausing in RTG deployment resulted in the micro-catheter becoming plugged by gelled RTG. The RTG plug was aspirated back into the 5Fr catheter using suction after removing the 1.9 French catheter to show RTG retrieval/replacement, 4:31 in Viemo video. The RTG plug was ejected and aspirated several times as shown in the video.

Deploying of RTG in a beaker of warm water is shown at the 9:09 time point in the video.

Discussion

RTG was shown to effectively occlude an explanted SV within an ex-vivo test apparatus mimicking in-vivo conditions. The RTG material was shown to be deployable in several configurations depending on the procedure used, thin self-piling noodle, thick straight noodle and space filling liquid. The space filling liquid proved to be the most effective at occluding the blood vessel in this experiment. However, the attempt at occluding the vessel with the gelled noodle was ended by allowing the RTG to fully gel within the microcatheter because RTG injection was paused during deployment for an interval long enough to allow the RTG to fully gel. Other systems are contemplated for ex-vivo RTG embolization.

Statements Regarding Incorporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Every formulation or combination of components described or exemplified herein can be used to practice the invention, unless otherwise stated.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A reversible thermal gel polymer formulation, comprising:
   (a) reversible thermal gel polymers, wherein each of the polymers independently comprise:
      a first polymer block comprising first repeating units, wherein each of the first repeating units of the first polymer block independently comprise a hydrophilic group; and
      a second polymer block comprising second repeating units, wherein each of the second repeating units of the second polymer block independently comprise a thermosensitive group; wherein:
      the first polymer block and the second polymer block are directly or indirectly covalently linked;

wherein:
each of the polymers is independently is characterized by the formula (FX4):

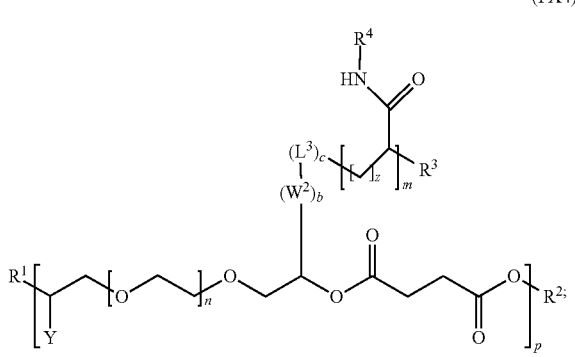

(FX4)

Y is selected from the group consisting of —OH, a radiopaque group, and a targeting ligand;

$L^3$, if present, is selected from the group consisting of a single bond, —$(CH_2)_q$—, —$(HCCH)_q$—, —$(CH_2CH_2X)_q$—, —$(CHXH)_q$—, —X—, —$NR^5$—, —CX—, —CXX—, —XCX—, —XCX$(CH_2)_q$CXX—, —$CXNR^5$—, —$NR^5CX$—, —$XCXNR^5$—, —$NR^5CXX$—, —CX$(CH_2)_qCR^5CN$—, —$(CH_2)_qX(CH_2)_r$—, —$(CH_2)_qXX(CH_2)_r$—, —$(CH_2)_qNR^5(CH_2)_r$—, —$(CH_2)_qCX(CH_2)_r$—, —$(CH_2)_qCXX(CH_2)_r$—, —$(CH_2)_qCXNR^5(CH_2)_r$—, —$(CH_2)_qNR^5CX(CH_2)_r$—, —$(CH_2)_qXCXNR^5(CH_2)_r$—, and —$(CH_2)_qNR^5CXNR^6(CH_2)_r$—;

X is O or S;

$W^2$, if present, is selected from the group consisting of a single bond, —$(CH_2)_q$—, —$(HCCH)_q$—, —$(CH_2CH_2X)_q$—, —$(CHXH)_q$—, —X—, —CXX—, —XCX—, —CX—, —XCX$(CH_2)_qCXX$—, and —$NR_{11}$—;

$W^2$, if present, is selected from the group consisting of a single bond, —$(CH_2)_q$—, —$(HCCH)_q$—, —$(CH_2CH_2X)_q$—, —$(CHXH)_q$—, —X—, —CXX—, —XCX, —CX—, —XCX$(CH_2)_qCXX$—, and —$NR^{11}$—;

each of $R^1$, $R^2$, $R^3$, and $R^4$ is independently selected from the group consisting of hydrogen, halide, and $C_1$-$C_5$ alkyl;

each of a, b and c is independently 0 or 1;

each of q and r is an integer independently selected from the range of 1 to 10:

z is an integer selected from the range of 0 to 4;

m is an integer selected from the range of 1 to 10,000;

n is an integer selected from the range of 1 to 1,000;

p is an integer selected from the range of 1 to 1,000; and each of $R^5$, $R^6$ and $R^{11}$ is independently selected from the group consisting of hydrogen, $C_1$-$C_{10}$ alkyl, $C_5$-$C_{10}$ aryl, and $C_5$-$C_{10}$ heteroaryl;

and (b) a solvent;

wherein said reversible thermal gel polymers are dissolved in said solvent and have a concentration in the solvent selected from the range of 2% to 50% w/v; and wherein the polymer formulation is characterized by a viscosity less than or equal to 1,500 cP.

2. The polymer formulation of claim 1, wherein the polymers in the formulation have a weight-averaged molecular weight selected from the range of 10,000 to 500,000 kDa.

3. The polymer formulation of claim 1, wherein the polymers in the formulation are characterized by a polydispersity index less than or equal to 4.0.

4. The polymer formulation of claim 1, wherein the polymer formulation is characterized by a low critical solution temperature selected from the range of 32° C. to 37° C.

5. The polymer formulation of claim 1, wherein the polymer formulation, when in solid form, is characterized by a compressive strength selected from the range of 300 kPa to 10 MPa.

6. The polymer formulation of claim 1, wherein the polymer formulation, when in solid form, is characterized by a tensile strain-to-failure selected from the range of 150% to 200%.

7. The polymer formulation of claim 1, wherein the solvent is water, saline, or phosphate-buffered saline.

8. The polymer formulation of claim 1, wherein the polymer formulation further comprises at least one contrasting agent.

9. The polymer formulation of claim 1, wherein the polymer formulation further comprises thrombin.

10. The polymer formulation of claim 1, wherein the polymer formulation further comprises collagen.

11. The polymer formulation of claim 1, wherein the polymer formulation further comprises a co-solvent.

12. The polymer formulation of claim 1, wherein the polymer formulation is characterized by a viscosity selected from the range of 1 cP to 1,500 cP.

13. The polymer formulation of claim 1, wherein the concentration of the polymers in the solvent is greater than or equal to 15% w/v.

14. The polymer formulation of claim 1, wherein the polymer formulation is capable of being injected from a catheter that has a diameter selected from the range of 1 to 8 French.

15. The polymer formulation of claim 1, wherein the polymer formulation forms a gel, upon a change in temperature.

16. The polymer formulation of claim 15, wherein the gel comprises a pattern, the pattern comprising one or more of straight noodles, helixes, coils, microparticles, and nanoparticles.

17. The polymer formulation of claim 15, wherein the polymer formulation forms the gel in an in vivo medium.

18. The polymer formulation of claim 1, wherein each of the polymers independently is characterized by the formula (FX5):

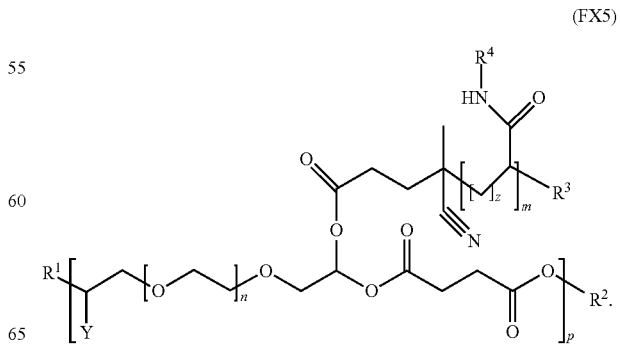

(FX5)

19. The polymer formulation of claim 1, wherein each of the polymers independently is characterized by the formula (FX6):
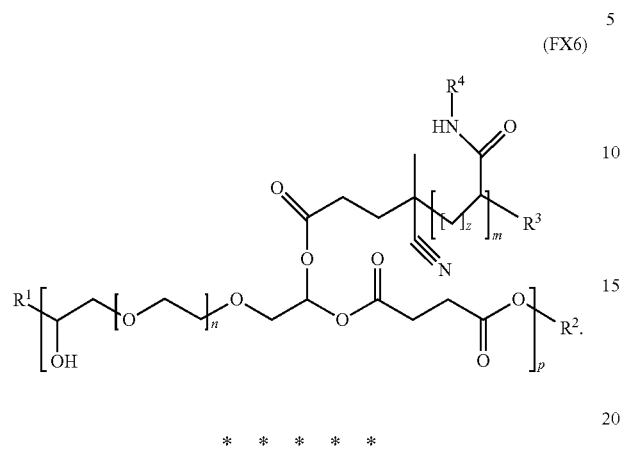
* * * * *

UNITED STATES PATENT AND TRADEMARK OFFICE
CERTIFICATE OF CORRECTION

PATENT NO. : 11,911,532 B2
APPLICATION NO. : 16/498595
DATED : February 27, 2024
INVENTOR(S) : Robin Shandas et al.

It is certified that error appears in the above-identified patent and that said Letters Patent is hereby corrected as shown below:

In the Claims

In Claim 1, Column 73, Line 37, delete "$W^2$, if present, is selected from the group consisting of a single bond, $-(CH_2)_q-$, $-(HCCH)_q-$, $-(CH_2CH_2X)_q-$, $-(CHXH)_q-$, $-X-$, $-CXX-$, $-XCX-$, $-CX-$, $-XCX(CH_2)_qCXX-$, and $-NR_{11}-$;".

In Claim 1, Column 73, Line 51, replace "each of a, b and c" with --each of b and c--.

Signed and Sealed this
Eighteenth Day of June, 2024

Katherine Kelly Vidal
*Director of the United States Patent and Trademark Office*